(12) United States Patent
Kostrzewski et al.

(10) Patent No.: US 12,082,886 B2
(45) Date of Patent: Sep. 10, 2024

(54) ROBOTIC SURGICAL SYSTEMS FOR PREPARING HOLES IN BONE TISSUE AND METHODS OF THEIR USE

(71) Applicant: KB MEDICAL, SA, Audubon, PA (US)

(72) Inventors: Szymon Kostrzewski, Lausanne (CH); Chetan Patel, Longwood, FL (US)

(73) Assignee: Globus Medical Inc., Audubon, PA (US)

( * ) Notice: Subject to any disclaimer, the term of this patent is extended or adjusted under 35 U.S.C. 154(b) by 49 days.

(21) Appl. No.: 17/534,670

(22) Filed: Nov. 24, 2021

(65) Prior Publication Data

US 2022/0079688 A1     Mar. 17, 2022

Related U.S. Application Data

(63) Continuation of application No. 15/946,179, filed on Apr. 5, 2018, now abandoned.
(Continued)

(51) Int. Cl.
| | |
|---|---|
| *A61B 17/16* | (2006.01) |
| *A61B 17/17* | (2006.01) |
| *A61B 34/00* | (2016.01) |
| *A61B 34/20* | (2016.01) |
| *A61B 34/30* | (2016.01) |

(Continued)

(52) U.S. Cl.
CPC .......... *A61B 34/20* (2016.02); *A61B 17/1615* (2013.01); *A61B 17/1626* (2013.01); *A61B 17/1703* (2013.01); *A61B 34/30* (2016.02); *A61B 34/76* (2016.02); *A61B 1/317* (2013.01); *A61B 2017/00022* (2013.01); *A61B 2017/00115* (2013.01); *A61B 17/1757* (2013.01); *A61B 34/10* (2016.02); *A61B 2034/105* (2016.02); *A61B 2034/107* (2016.02); *A61B 2034/2046* (2016.02); *A61B 2034/2055* (2016.02); *A61B 2034/2059* (2016.02); *A61B 34/70* (2016.02); *A61B 2090/064* (2016.02); *A61B 2090/3762* (2016.02)

(58) Field of Classification Search
CPC . A61B 17/1615; A61B 17/1631; A61B 34/10; A61B 34/20; A61B 34/30
See application file for complete search history.

(56) References Cited

U.S. PATENT DOCUMENTS

| | | |
|---|---|---|
| 4,150,293 A | 4/1979 | Franke |
| 5,246,010 A | 9/1993 | Gazzara et al. |
| (Continued) | | |

*Primary Examiner* — Si Ming Ku

(57) ABSTRACT

Described herein are systems and methods for use in preparing holes in bones. In certain embodiments, the trajectory followed in preparing a hole in a bone is optimized by adjusting characteristics of rotation of a drill bit (e.g., an anti-skiving drill bit). In certain embodiments, a change in material is determined once a hard outer layer of a bone has been drilled. Subsequently, characteristics of rotation of a drill bit are altered to allow natural features of a patient's anatomy to guide the drill bit. In this way, certain hard walls of certain bones can act to redirect a drill bit. The change in material may be determined, and/or characteristics of rotation altered, by a surgeon or a robotic surgical system (e.g., automatically). In certain embodiments, a robotic surgical system notifies a surgeon of a change in material to prompt the surgeon to alter the characteristics of rotation.

16 Claims, 56 Drawing Sheets

Related U.S. Application Data

(60) Provisional application No. 62/482,120, filed on Apr. 5, 2017.

(51) Int. Cl.

| | |
|---|---|
| A61B 1/317 | (2006.01) |
| A61B 17/00 | (2006.01) |
| A61B 34/10 | (2016.01) |
| A61B 90/00 | (2016.01) |

(56) References Cited

U.S. PATENT DOCUMENTS

| | | |
|---|---|---|
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,823,207 B1 | 11/2004 | Jensen et al. |
| 6,856,826 B2 | 2/2005 | Seeley et al. |
| 6,856,827 B2 | 2/2005 | Seeley et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,996,487 B2 | 2/2006 | Jutras et al. |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,167,738 B2 | 1/2007 | Schweikard et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,366,562 B2 | 4/2008 | Dukesherer et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,606,613 B2 | 10/2009 | Simon et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,751,865 B2 | 7/2010 | Jascob et al. |
| 7,760,849 B2 | 7/2010 | Zhang |
| 7,796,728 B2 | 9/2010 | Bergfjord |
| 7,813,838 B2 | 10/2010 | Sommer |
| 7,818,044 B2 | 10/2010 | Dukesherer et al. |
| 7,831,294 B2 | 11/2010 | Viswanathan |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,844,320 B2 | 11/2010 | Shahidi |
| 7,853,305 B2 | 12/2010 | Simon et al. |
| 7,853,313 B2 | 12/2010 | Thompson |
| D631,966 S | 2/2011 | Perloff et al. |
| 7,879,045 B2 | 2/2011 | Gielen et al. |
| 7,881,770 B2 | 2/2011 | Melkent et al. |
| RE42,194 E | 3/2011 | Foley et al. |
| RE42,226 E | 3/2011 | Foley et al. |
| 7,900,524 B2 | 3/2011 | Calloway et al. |
| 7,925,653 B2 | 4/2011 | Saptharishi |
| 7,940,999 B2 | 5/2011 | Liao et al. |

(56) References Cited

U.S. PATENT DOCUMENTS

| | | |
|---|---|---|
| 7,945,012 B2 | 5/2011 | Ye et al. |
| 7,945,021 B2 | 5/2011 | Shapiro et al. |
| 7,953,470 B2 | 5/2011 | Vetter et al. |
| 7,971,341 B2 | 7/2011 | Dukesherer et al. |
| 7,974,677 B2 | 7/2011 | Mire et al. |
| 7,974,681 B2 | 7/2011 | Wallace et al. |
| 7,983,733 B2 | 7/2011 | Viswanathan |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,052,688 B2 | 11/2011 | Wolf, II |
| 8,057,397 B2 | 11/2011 | Li et al. |
| 8,057,407 B2 | 11/2011 | Martinelli et al. |
| 8,062,375 B2 | 11/2011 | Glerum et al. |
| 8,086,299 B2 | 12/2011 | Adler et al. |
| 8,098,914 B2 | 1/2012 | Liao et al. |
| 8,100,950 B2 | 1/2012 | St. Clair et al. |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,121,249 B2 | 2/2012 | Wang et al. |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,208,708 B2 | 6/2012 | Homan et al. |
| 8,208,988 B2 | 6/2012 | Jenser |
| 8,224,024 B2 | 7/2012 | Foxlin et al. |
| 8,263,933 B2 | 7/2012 | Hartmann et al. |
| 8,239,001 B2 | 8/2012 | Verard et al. |
| 8,248,413 B2 | 8/2012 | Gattani et al. |
| 8,271,069 B2 | 9/2012 | Jascob et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,335,552 B2 | 12/2012 | Stiles |
| 8,335,557 B2 | 12/2012 | Maschke |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,379,791 B2 | 2/2013 | Forthmann et al. |
| 8,386,019 B2 | 2/2013 | Camus et al. |
| 8,394,099 B2 | 3/2013 | Patwardhan |
| 8,450,694 B2 | 5/2013 | Baviera et al. |
| RE44,305 E | 6/2013 | Foley et al. |
| 8,462,911 B2 | 6/2013 | Vesel et al. |
| 8,467,851 B2 | 6/2013 | Mire et al. |
| 8,467,852 B2 | 6/2013 | Csavoy et al. |
| RE44,392 E | 7/2013 | Hynes |
| 8,483,434 B2 | 7/2013 | Buehner et al. |
| 8,483,800 B2 | 7/2013 | Jensen et al. |
| 8,518,120 B2 | 8/2013 | Glerum et al. |
| 8,526,688 B2 | 9/2013 | Groszmann et al. |
| 8,526,700 B2 | 9/2013 | Isaacs |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,556,979 B2 | 10/2013 | Glerum et al. |
| 8,560,118 B2 | 10/2013 | Green et al. |
| 8,597,198 B2 | 12/2013 | Sanborn et al. |
| 8,600,478 B2 | 12/2013 | Verard et al. |
| 8,611,985 B2 | 12/2013 | Lavallee et al. |
| 8,630,389 B2 | 1/2014 | Kato |
| 8,634,897 B2 | 1/2014 | Simon et al. |
| 8,644,907 B2 | 2/2014 | Hartmann et al. |
| 8,657,809 B2 | 2/2014 | Schoepp |
| 8,660,635 B2 | 2/2014 | Simon et al. |
| 8,675,939 B2 | 3/2014 | Moctezuma de la Barrera |
| 8,678,647 B2 | 3/2014 | Gregerson et al. |
| 8,679,183 B2 | 3/2014 | Glerum et al. |
| 8,682,413 B2 | 3/2014 | Lloyd |
| 8,685,098 B2 | 4/2014 | Glerum et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,740,882 B2 | 6/2014 | Jun et al. |
| 8,781,186 B2 | 7/2014 | Clements et al. |
| 8,781,630 B2 | 7/2014 | Banks et al. |
| 8,787,520 B2 | 7/2014 | Baba |
| 8,792,704 B2 | 7/2014 | Isaacs |
| 8,798,231 B2 | 8/2014 | Notohara et al. |
| 8,812,077 B2 | 8/2014 | Dempsey |
| 8,814,793 B2 | 8/2014 | Brabrand |
| 8,818,105 B2 | 8/2014 | Myronenko et al. |
| 8,821,511 B2 | 9/2014 | Von Jako et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,022,131 B1* | 7/2018 | Burley .............. A61B 17/17 |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0143651 A1 | 6/2005 | Verard et al. |
| 2005/0171558 A1 | 8/2005 | Abovitz et al. |

(56) References Cited

U.S. PATENT DOCUMENTS

| | | |
|---|---|---|
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0038059 A1 | 2/2007 | Sheffer et al. |
| 2007/0073133 A1 | 3/2007 | Schoenefeld |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0144906 A1 | 6/2008 | Allred et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0228117 A1 | 9/2010 | Hartmann |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2011/0098553 A1 | 4/2011 | Robbins et al. |
| 2011/0137152 A1 | 6/2011 | Li |
| 2011/0230967 A1 | 9/2011 | O'Halloran et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2012/0035507 A1 | 2/2012 | George et al. |
| 2012/0051498 A1 | 3/2012 | Koishi |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0143084 A1 | 6/2012 | Shoham |
| 2012/0143195 A1* | 6/2012 | Sander ............... F16D 3/207 464/106 |
| 2012/0184839 A1 | 7/2012 | Woerlein |
| 2012/0226145 A1 | 9/2012 | Chang et al. |
| 2012/0235909 A1 | 9/2012 | Birkenbach et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0016889 A1 | 1/2013 | Myronenko et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0113791 A1 | 5/2013 | Isaacs et al. |
| 2013/0165937 A1 | 6/2013 | Patwardhan |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0272488 A1 | 10/2013 | Bailey et al. |
| 2013/0272489 A1 | 10/2013 | Dickman et al. |
| 2013/0281821 A1 | 10/2013 | Liu et al. |
| 2013/0303887 A1 | 11/2013 | Holsing et al. |
| 2013/0307955 A1 | 11/2013 | Deitz et al. |
| 2013/0331686 A1 | 12/2013 | Freysinger et al. |
| 2013/0342578 A1 | 12/2013 | Isaacs |
| 2013/0345757 A1 | 12/2013 | Stad |
| 2014/0012131 A1 | 1/2014 | Heruth et al. |
| 2014/0031664 A1 | 1/2014 | Kang et al. |
| 2014/0046132 A1 | 2/2014 | Hoeg et al. |
| 2014/0049629 A1 | 2/2014 | Siewerdsen et al. |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0121676 A1 | 5/2014 | Kostrzewski et al. |
| 2014/0135796 A1 | 5/2014 | Simon et al. |
| 2014/0148692 A1 | 5/2014 | Hartmann et al. |
| 2014/0171781 A1 | 6/2014 | Stiles |
| 2014/0171900 A1 | 6/2014 | Stiles |
| 2014/0187915 A1 | 7/2014 | Yaroshenko et al. |
| 2014/0130810 A1 | 8/2014 | Azizian et al. |
| 2014/0221819 A1 | 8/2014 | Sarment |
| 2014/0234804 A1 | 8/2014 | Huang et al. |
| 2014/0275985 A1 | 9/2014 | Walker et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0100066 A1* | 4/2015 | Kostrzewski .......... A61B 34/30 606/130 |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0113728 A1* | 4/2016 | Piron .................. A61B 34/30 606/130 |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |

* cited by examiner

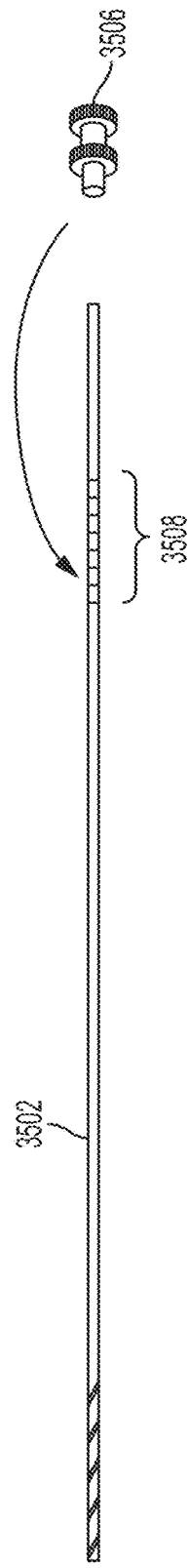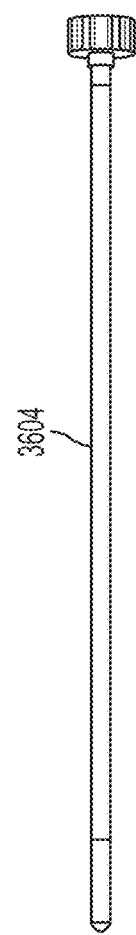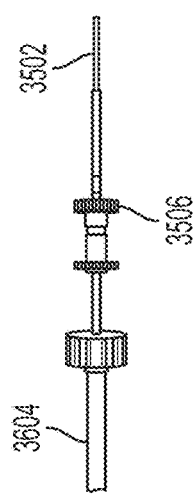
FIG. 35A
FIG. 35B
FIG. 35C

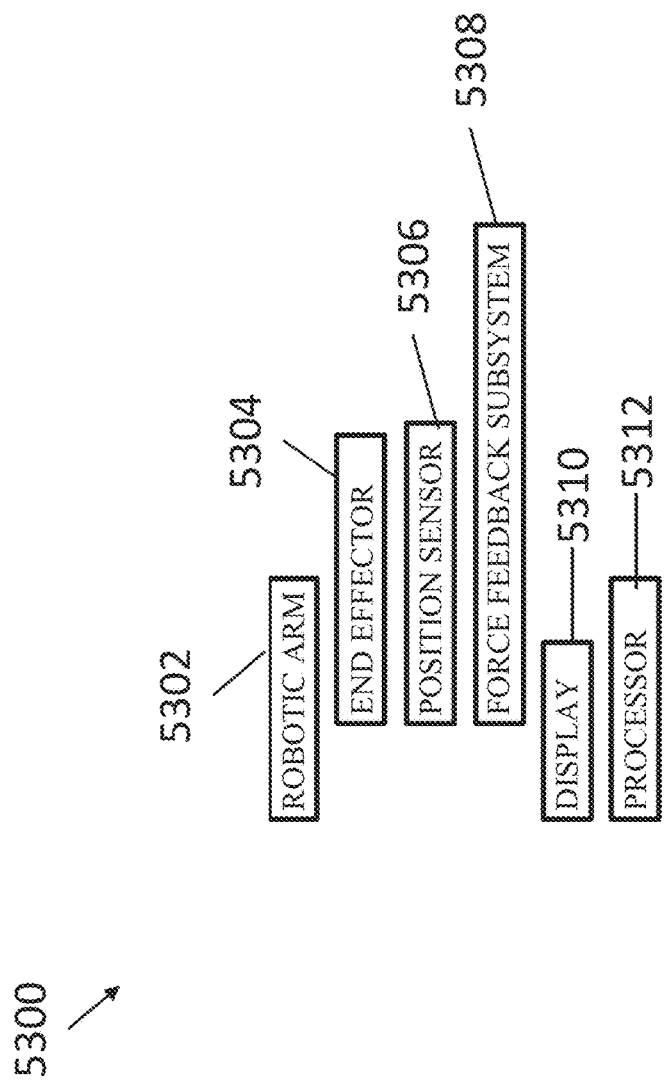

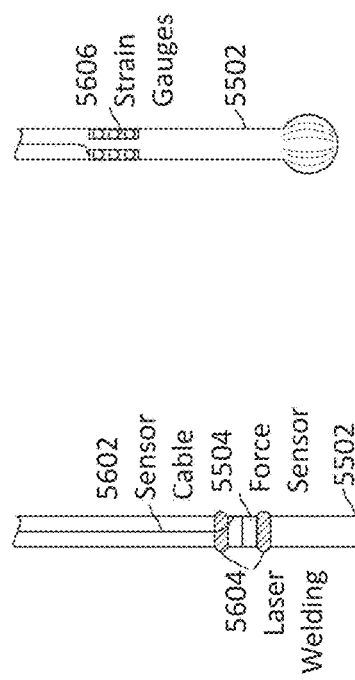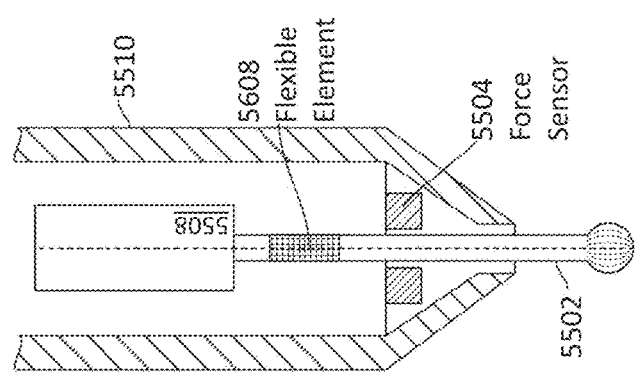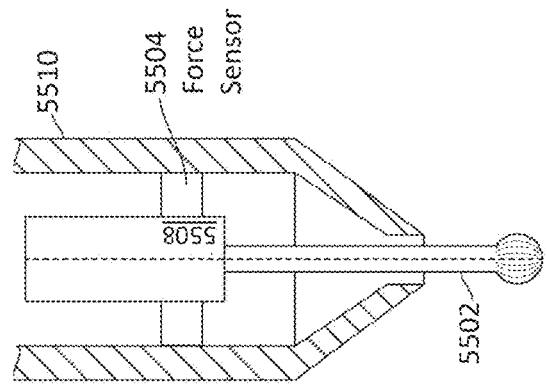

ROBOTIC SURGICAL SYSTEMS FOR PREPARING HOLES IN BONE TISSUE AND METHODS OF THEIR USE

CROSS REFERENCE TO RELATED APPLICATIONS

This is a continuation of U.S. application Ser. No. 15/946,179, filed Apr. 5, 2018. which claims priority to U.S. Provisional Application Ser. No. 62/482,120 filed on Apr. 5, 2017, all of which are incorporated in their entirety herein.

FIELD OF THE INVENTION

The present invention relates generally to robotic surgical systems and methods of use that guide and/or assist in preparation of holes in bone.

BACKGROUND

Spinal surgeries often require precision drilling and placement of screws or other implants in bone tissue. Catastrophic damage or death may result from improper drilling or maneuvering of the body during spinal surgery due to the proximity of the spinal cord and arteries. Further, accurate placement is typically necessary for a successful outcome. For example, spinal fusion is typically augmented by stabilizing the vertebrae with fixation devices, such as metallic screws, rods, and plates, to facilitate bone fusion. In spinal fusion, as well as other surgeries, the accuracy with which the screws are placed in the bone has a direct effect on the outcome of the procedure. The less motion there is between the two bones trying to heal, the higher the change the bones will successfully fuse. The use of fixation devices has increased the success rate of spinal fusion procedures considerably.

Such procedures rely strongly on the expertise of the surgeon, and there is significant variation in success rate among different surgeons. A number of navigational and verification approaches have been developed. However, screw misplacement is still a common problem in such surgical procedures, especially during minimally invasive procedures. Screws may be misaligned due to inaccurate (relative to a chosen trajectory) holes drilled prior to inserting the screw. Screws may additionally be misaligned due to a sub-optimally selected initial trajectory. Misaligned screws can cause significant harm to patients if the placement of screws breaches delicate areas. For example, a vertebral screw may damage a spinal cord, causing chronic pain, if the pedicle wall is breached.

The actual entry point of a drill bit into a bone can differ from the intended trajectory due to skidding of the drill bit when preparing a hole. Specifically, the angle of the tip of the drill may cause the drill bit to skid as the tip contacts the bone tissue, thereby causing the hole to be drilled along an incorrect trajectory. Typically, unless a bone drill is driven at 90 degrees to the bone surface there is a tendency for the drill bit to skid over the bone surface thereby placing the hole inappropriately.

A surgeon's initial planned trajectory may be sub-optimal based on limitations in the equipment used in preparing a hole or the surgical environment. Soft tissue around a surgical site may put pressure on surgical instruments that causes a deviated trajectory. Medical images and/or navigational systems used to perform procedures may be imprecise. For example, contrast in medical images may be insufficient to properly plan a safe trajectory. Patient anatomy may shift during a procedure without such shifts be accounted for in the planned trajectory. Sub-optimal trajectories may pose a risk (e.g., increased risk) of breaching into sensitive areas (e.g., nerves, spinal canal).

Thus, there is a need for systems and methods for preparing holes in a patient's bone while optimizing the trajectory of surgical instruments used in the preparation to minimize the risks of complications to the patient.

SUMMARY

Described herein are systems and methods for use in preparing holes in bones. In certain embodiments, the trajectory followed in preparing a hole in a bone is optimized by adjusting characteristics of rotation of the drill bit being used. Bones consist of a hard outer layer and a spongious interior. In certain embodiments, misalignment is avoided when drilling the hard outer layer by using an anti-skiving drill bit rotating at a high rotational speed. In certain embodiments, a change in material is determined once a hard outer layer has been drilled. Subsequently, characteristics of rotation of a drill bit are altered to allow natural features of a patient's anatomy to guide the drill bit to optimize its trajectory and reduce complications to the patient. In this way, certain hard boundary layers in certain bones can act to redirect a drill bit. The change in material may be determined and/or characteristics of rotation may be altered by a surgeon or a robotic surgical system (e.g., automatically). In certain embodiments, a robotic surgical system notifies a surgeon of a change in material (e.g., as a drill bit enters the spongious interior from the hard outer layer), which prompts the surgeon to alter characteristics of rotation for further drilling.

In certain embodiments, the disclosed technology is methods for use in preparing holes in bones. The methods comprise rotating a drill bit, determining a change in material at the tip of the drill bit, and altering and/or notifying a surgeon to alter characteristics of rotation of the drill bit. In certain embodiments, a surgeon determines that a change in material has occurred and/or manually alters the characteristics of rotation. A drill bit attached to a drill affixed to a robotic surgical system is rotated. In certain embodiments, the rotation of the drill bit is controlled by the robotic surgical system (e.g., based on input from a surgeon or based on preoperative planning). A change in material is determined at a terminal point of the drill bit, for example, based on haptic feedback measured by a force sensor. Upon determining a change in material, at least one of the following occurs: one or more characteristics of rotation are altered (e.g., automatically by the robotic surgical system) and a surgeon is notified to alter one or more characteristics of rotation.

A change in material may be determined based on one or more of a plurality of inputs. Haptic feedback (e.g., as measured by a force sensor) may be used to determine a change in material based on the change in mechanical response between the initial and subsequent material as recorded in the haptic feedback. In certain embodiments, haptic feedback is felt directly by a surgeon while manually operating a drill (e.g., wherein a change in resistance to further drilling is felt by the surgeon as the surgeon advances the drill bit). Haptic feedback may result from a change in density, elasticity, hardness, and/or porosity between materials. A position of the drill bit may be used to determine the change in material. The position may be in relation to a model of the patient's anatomy (e.g., derived from medical image data) registered to the robotic surgical system. The position may be in relation to a pre-planned trajectory (e.g., wherein the surgeon pre-selects the position where the change in material occurs).

Characteristics of rotation that may be changed once a change in material has been determined (e.g., once the spongious part of a bone has been entered) comprise rotational speed, rotational velocity, rotational direction (e.g., clockwise or counterclockwise), and rotational mode. Rotational modes may be an oscillatory mode where the drill bit oscillates over some arc or a unidirectional (e.g., clockwise or counterclockwise) rotation mode.

In certain embodiments, rotational speed is reduced (e.g., to 10-20 rpm) once a change in material has been determined. Slow rotational speed is sufficient to prepare holes through certain materials, such as the spongious interior of a bone, but insufficient to drill through others, such as the hard outer layer of the bone. Similarly, in certain embodiments, oscillatory rotations or counterclockwise rotations can drill through spongious interior but not hard outer layer of bone. In this way, in certain embodiments, a portion of a hard outer layer of a bone acts to redirect a drill bit and thus modify the trajectory of the bit while preparing a hole.

In one aspect, the present disclosure is direct to a method of drilling a hole in bone of a patient with a robotic arm of a robotic surgical system, the method comprising: determining (e.g., by a processor of the robotic surgical system) (e.g., automatically) a change in material (e.g., wherein the change in material is a change in one or more properties of a material) at a terminal point (e.g., tip) of a drill bit (e.g., an anti-skiving drill bit); and altering (e.g., automatically by the processor) one or more characteristics of rotation of the drill bit based, at least in part, on the change in material.

In certain embodiments, the one or more characteristics of rotation are selected from the group consisting of rotational speed, rotational velocity, rotational direction (e.g., clockwise or counterclockwise), and rotational mode (e.g., wherein the rotational mode is either an oscillatory rotation mode or a unidirectional rotation mode). In certain embodiments, the one or more characteristics of rotation are rotational speed (e.g., and wherein the altering step comprises decreasing the rotational speed (e.g., to between 10 and 20 rpm)).

In certain embodiments, the method comprises measuring (e.g., by the processor), prior to the determining step, haptic feedback (e.g., by a force sensor) (e.g., as felt by a surgeon); and the determining step comprises determining the change in material based, at least in part, on the haptic feedback (e.g., wherein the haptic feedback comprises measurements from a plurality of positions of the drill bit). In certain embodiments, the haptic feedback is measured by at least one force sensor and at least one of the at least one force sensors is attached to one of the end effector, the drill, and the robotic arm.

In certain embodiments, the determining step comprises: determining the change in material based, at least in part, on medical image data (e.g., a change in at least one of brightness, contrast and color between regions of one or more medical images). In certain embodiments, the method comprises determining the change in material based, at least in part, on a position of the terminal point of the drill bit (e.g., in relation to an anatomical model of the patient (e.g., derived from medical image data) (e.g., based on the position of the terminal point relative to regions of one or more medical images that differ in at least one of brightness, contrast, and color))(e.g., using a registration (e.g., wherein the registration comprises a mapping between a robot coordinate system and a medical image data coordinate system)).

In certain embodiments, the method comprises: moving (e.g., automatically) the drill bit along a pre-determined trajectory, wherein motion of the drill bit is constrained to along the pre-determined trajectory.

In certain embodiments, the method comprises: notifying (e.g., by the processor) (e.g., automatically) a surgeon, upon determination of the change in material, with a notification, wherein the notification comprises at least one member selected from the group consisting of: haptic feedback provided to the surgeon, a sound, a graphic (e.g., at least one of a pop-up image, icon, or text (e.g., by rendering on a display)), and a light signal. In certain embodiments, the notification prompts the surgeon to alter the one or more characteristics of rotation. In certain embodiments, the one or more characteristics of rotation are selected from the group consisting of rotational speed, rotational velocity, rotational direction (e.g., clockwise or counterclockwise), and rotational mode (e.g., wherein the rotational mode is either an oscillatory rotation mode or a unidirectional rotation mode). In certain embodiments, the change in material is a change from a hard outer layer of a bone to a spongious interior of the bone.

In one aspect, the present disclosure is directed to a method of notifying a surgeon of a change while drilling a bone of a patient with a robotic arm of a robotic surgical system, the method comprising: determining (e.g., by a processor of the robotic surgical system) (e.g., automatically) a change in material (e.g., wherein the change in material is a change in one or more properties of a material) at a terminal point (e.g., tip) of a drill bit (e.g., an anti-skiving drill bit); and notifying (e.g., by the processor) (e.g., automatically) the surgeon, upon determination of the change in material, with a notification, wherein the notification comprises at least one member selected from the group consisting of: haptic feedback provided to the surgeon, a sound, a graphic (e.g., at least one of a pop-up image, icon, or text (e.g., by rendering on a display)), and a light signal.

In certain embodiments, the notification prompts the surgeon to alter one or more characteristics of rotation. In certain embodiments, the one or more characteristics of rotation are selected from the group consisting of rotational speed, rotational velocity, rotational direction (e.g., clockwise or counterclockwise), and rotational mode (e.g., wherein the rotational mode is either an oscillatory rotation mode or a unidirectional rotation mode).

In certain embodiments, the method comprises altering (e.g., automatically) (e.g., by the processor) one or more characteristics of rotation of the drill bit based, at least in part, on the change in material. In certain embodiments, the one or more characteristics of rotation are selected from the group consisting of rotational speed, rotational velocity, rotational direction (e.g., clockwise or counterclockwise), and rotational mode (e.g., wherein the rotational mode is either an oscillatory rotation mode or a unidirectional rotation mode). In certain embodiments, the one or more characteristics of rotation are rotational speed (e.g., and wherein the altering step comprises decreasing the rotational speed (e.g., to between 10 and 20 rpm).

In certain embodiments, the method comprises measuring (e.g., by the processor), prior to the determining step, haptic feedback (e.g., by a force sensor) (e.g., as felt by a surgeon); and the determining step comprises determining the change in material based, at least in part, on the haptic feedback (e.g., wherein the haptic feedback comprises measurements from a plurality of positions of the drill bit). In certain embodiments, the haptic feedback is measured by at least one force sensor and at least one of the at least one force sensors is attached to one of the end effector, the drill, and the robotic arm.

In certain embodiments, moving (e.g., automatically) the drill bit along a predetermined trajectory, wherein motion of the drill bit is constrained to along the pre-determined trajectory.

In certain embodiments, the determining step comprises: determining the change in material based, at least in part, on medical image data (e.g., a change in at least one of brightness, contrast and color between regions of one or more medical images). In certain embodiments, the determining step comprises: determining the change in material based, at least in part, on a position of a terminal point of the drill bit (e.g., in relation to an anatomical model of the patient (e.g., derived from medical image data) (e.g., based on the position of the terminal point relative to regions of one or more medical images that differ in at least one of brightness, contrast, and color))(e.g., using a registration (e.g., wherein the registration comprises a mapping between a robot coordinate system and a medical image data coordinate system)). In certain embodiments, the change in material is a change from a hard outer layer of a bone to a spongious interior of the bone.

In certain embodiments, the method comprises: rotating (e.g., automatically based at least in part on one or more surgeon inputs to the robotic surgical system) the drill bit (e.g., at a speed exceed a threshold above which skiving is minimized for an anti-skiving drill bit), wherein the drill bit is attached (e.g., mounted) to a drill and the drill is attached (e.g., directly or indirectly) to an end effector of the robotic arm.

In one aspect, the present disclosure is directed to a robotic surgical system for drilling a hole in bone of a patient with a drill bit (e.g., an anti-skiving drill bit) attached to a drill attached to a robotic arm of the robotic surgical system, the system comprising: a robotic arm comprising an end effector; a processor; a non-transitory computer readable memory having instructions stored thereon, wherein the instructions, when executed by the processor, cause the processor to: determine, by the processor, (e.g., automatically) a change in material (e.g., wherein the change in material is a change in one or more properties of a material) at a terminal point (e.g., tip) of the drill bit; and alter, by the processor, (e.g., automatically) one or more characteristics of rotation of the drill bit based, at least in part, on the change in material.

In certain embodiments, the instructions, when executed by the processor, cause the processor to: automatically rotate (e.g., based at least in part on one or more surgeon inputs to the robotic surgical system) the drill bit (e.g., at a speed exceed a threshold above which skiving is minimized).

In certain embodiments, the one or more characteristics of rotation are selected from the group consisting of rotational speed, rotational velocity, rotational direction (e.g., clockwise or counterclockwise), and rotational mode (e.g., wherein the rotational mode is either an oscillatory rotation mode or a unidirectional rotation mode). In certain embodiments, the one or more characteristics of rotation are rotational speed (e.g., and wherein the instructions, when executed by the processor, cause the processor to decrease the rotational speed (e.g., to between 10 and 20 rpm).

In certain embodiments, the instructions, when executed by the processor, cause the processor to: measure, by the processor, prior to the determining step, haptic feedback (e.g., by a force sensor of the robotic surgical system); and determine, by the processor, the change in material based, at least in part, on the haptic feedback (e.g., wherein the haptic feedback comprises measurements from a plurality of positions of the drill bit). In certain embodiments, the robotic surgical system comprises at least one force sensor and the haptic feedback is measured by the at least one force sensor and at least one of the at least one force sensors is attached to one of the end effector, the drill, and the robotic arm.

In certain embodiments, the instructions, when executed by the processor, cause the processor to: move, by the processor, (e.g., automatically) the drill bit along a pre-determined trajectory, wherein motion of the drill bit is constrained to along the pre-determined trajectory.

In certain embodiments, the instructions, when executed by the processor, cause the processor to: determine, by the processor, the change in material based, at least in part, on medical image data (e.g., a change in at least one of brightness, contrast and color between regions of one or more medical images). In certain embodiments, the instructions, when executed by the processor, cause the processor to: determine, by the processor, the change in material based, at least in part, on a position of a terminal point of the drill bit (e.g., in relation to an anatomical model of the patient (e.g., derived from medical image data) (e.g., based on the position of the terminal point relative to regions of one or more medical images that differ in at least one of brightness, contrast, and color))(e.g., using a registration (e.g., wherein the registration comprises a mapping between a robot coordinate system and a medical image data coordinate system)).

In certain embodiments, the instructions, when executed by the processor, cause the processor to: notify, by the processor, a surgeon (e.g., automatically), upon determination of the change in material, with a notification, wherein the notification comprises at least one member selected from the group consisting of: haptic feedback provided to the surgeon, a sound, a graphic (e.g., at least one of a pop-up image, icon, or text (e.g., by rendering on a display)), and a light signal. In certain embodiments, the notification prompts the surgeon to alter the one or more characteristics of rotation. In certain embodiments, the one or more characteristics of rotation are selected from the group consisting of rotational speed, rotational velocity, rotational direction (e.g., clockwise or counterclockwise), and rotational mode (e.g., wherein the rotational mode is either an oscillatory rotation mode or a unidirectional rotation mode).

In certain embodiments, the change in material is a change from a hard outer layer of a bone to a spongious interior of the bone.

In one aspect, the present disclosure is directed to a robotic surgical system for notifying a surgeon of a change while drilling a bone of a patient with a robotic arm of the robotic surgical system, the robotic surgical system comprising: a robotic arm comprising an end effector; a processor; a non-transitory computer readable memory having instructions stored thereon, wherein the instructions, when executed by the processor, cause the processor to: determine, by the processor, (e.g., automatically) a change in material (e.g., wherein the change in material is a change in one or more properties of a material) at a terminal point (e.g., tip) of the drill bit; and notify, by the processor, (e.g., automatically) a surgeon, upon determination of the change in material, with a notification, wherein the notification comprises at least one member selected from the group consisting of: haptic feedback provided to the surgeon, a sound, a graphic (e.g., at least one of a pop-up image, icon, or text (e.g., by rendering on a display)), and a light signal.

In certain embodiments, the instructions, when executed by the processor, cause the processor to: automatically rotate (e.g., based at least in part on one or more surgeon inputs to the robotic surgical system) the drill bit (e.g., at a speed exceed a threshold above which skiving is minimized).

In certain embodiments, the notification prompts the surgeon to alter one or more characteristics of rotation. In certain embodiments, the one or more characteristics of rotation are selected from the group consisting of rotational speed, rotational velocity, rotational direction (e.g., clockwise or counterclockwise), and rotational mode (e.g., wherein the rotational mode is either an oscillatory rotation mode or a unidirectional rotation mode).

In certain embodiments, the instructions, when executed by the processor, cause the processor to: alter, by the processor, (e.g., automatically) one or more characteristics of rotation of the drill bit based, at least in part, on the change in material. In certain embodiments, the one or more characteristics of rotation are selected from the group consisting of rotational speed, rotational velocity, rotational direction (e.g., clockwise or counterclockwise), and rotational mode (e.g., wherein the rotational mode is either an oscillatory rotation mode or a unidirectional rotation mode). In certain embodiments, the one or more characteristics of rotation are rotational speed (e.g., and wherein instructions, when executed by the processor, cause the processor to decrease the rotational speed (e.g., to between 10 and 20 rpm).

In certain embodiments, the instructions, when executed by the processor, cause the processor to: measure, by the processor, prior to the determining step, haptic feedback (e.g., by a force sensor of the robotic surgical system); and determine, by the processor, the change in material based, at least in part, on the haptic feedback (e.g., wherein the haptic feedback comprises measurements from a plurality of positions of the drill bit). In certain embodiments, the robotic surgical system comprises at least one force sensor and the haptic feedback is measured by the at least one force sensor and at least one of the at least one force sensors is attached to one of the end effector, the drill, and the robotic arm.

In certain embodiments, the instructions, when executed by the processor, cause the processor to: move, by the processor, (e.g., automatically) the drill bit along a pre-determined trajectory, wherein motion of the drill bit is constrained to along the pre-determined trajectory.

In certain embodiments, the instructions, when executed by the processor, cause the processor to: determine, by the processor, the change in material based, at least in part, on medical image data (e.g., a change in at least one of brightness, contrast and color between regions of one or more medical images). In certain embodiments, the instructions, when executed by the processor, cause the processor to: determine, by the processor, the change in material based, at least in part, on a position of a terminal point of the drill bit (e.g., in relation to an anatomical model of the patient (e.g., derived from medical image data) (e.g., based on the position of the terminal point relative to regions of one or more medical images that differ in at least one of brightness, contrast, and color))(e.g., using a registration (e.g., wherein the registration comprises a mapping between a robot coordinate system and a medical image data coordinate system)).

In certain embodiments, the change in material is a change from a hard outer layer of a bone to a spongious interior of the bone.

BRIEF DESCRIPTION OF THE DRAWINGS

The foregoing and other objects, aspects, features, and advantages of the present disclosure will become more apparent and better understood by referring to the following description taken in conjunction with the accompanying drawings, in which:

FIG. 35A, FIG. 35B, and FIG. 35C illustrate anti-skive drill bits in accordance with embodiments of the disclosed technology;

FIG. 53 is an illustration of an example robotic surgical system, according to illustrative embodiments of the invention;

FIGS. 56A through 56D are illustrations of implementations of a force sensor integrated in a surgical drill, according to an illustrative embodiments of the invention.

Figure 1:
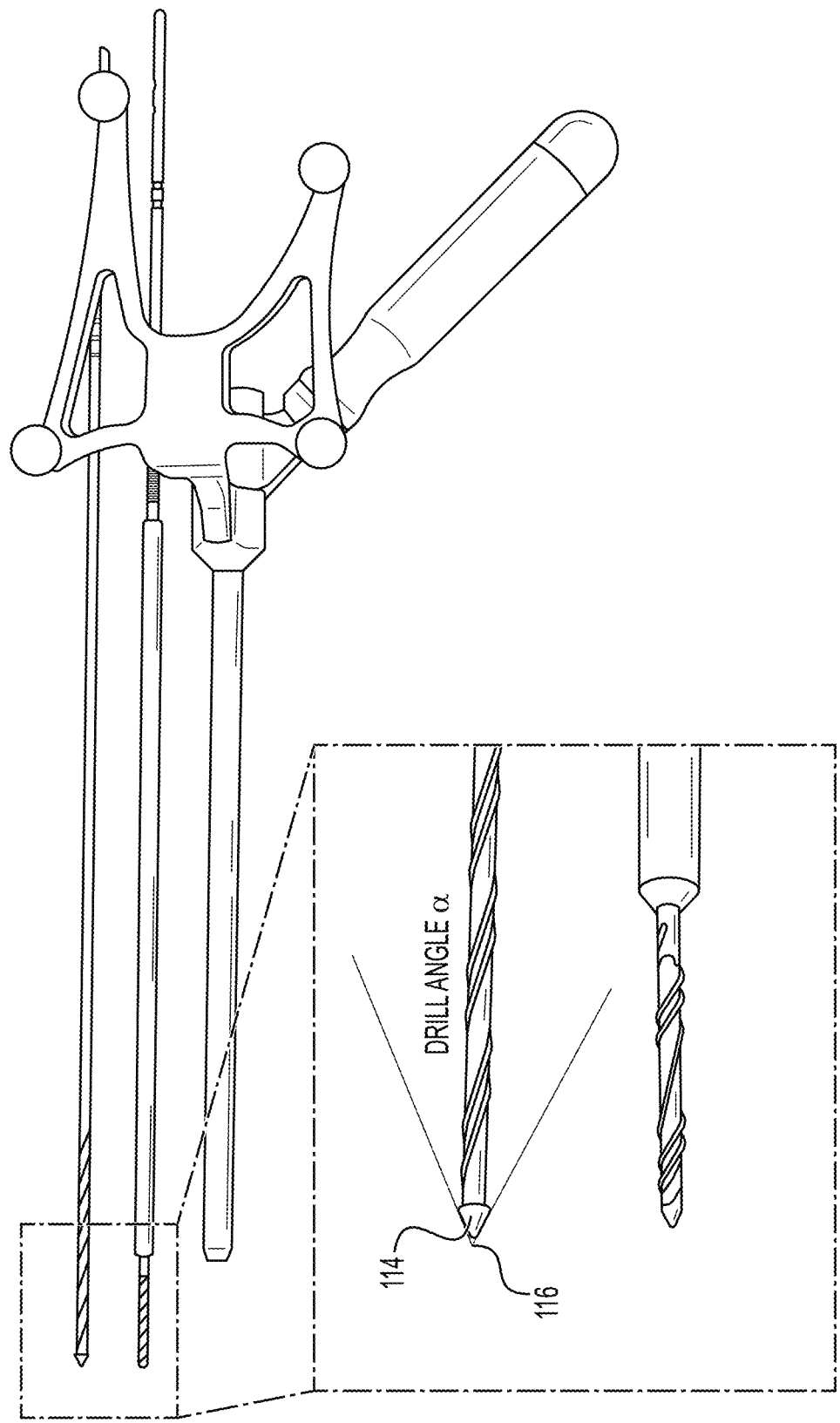
FIG. 1 is an illustration of example drill bits for preparing holes in bone tissue.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION OF THE DRAWINGS

Described herein are systems and methods for use in preparing holes in bone tissue. In certain types of surgeries it is necessary to prepare a precise hole in bone tissue (e.g. spinal surgeries and pedicle screw placement, intramedullary screw placement); however, in many instances, such as certain minimally invasive surgical procedures, pre- or intra-operatively selected trajectories present potential risks to the patient as they may cause drilling in highly undesired regions. The disclosed technology provides the ability to precisely prepare a hole in bone tissue by altering the rotational characteristics of a drill bit during drilling to avoid suboptimal drilling trajectories.

As used herein, the phrase "prepare a hole in bone tissue" encompasses milling, drilling, grinding, and/or cutting bone tissue and/or bone-like tissue. A "hole" encompasses any cavity, dent, or depression.

The methods described herein are suitable for use with a wide range of robotic surgical systems capable of preparing holes in bone tissue. In some embodiments, the robotic surgical system assists a surgeon while the surgeon manually controls hole preparation throughout the procedure (e.g., by manually manipulating a surgical drill attached to the surgical system including controlling rotational characteristics of the drilling using the drill itself). For example, a surgeon may manually control the insertion of a drill bit into a patient's bone or the rotation of the drill bit by providing input to the drill. In some embodiments, some or all steps of preparing a hole in a bone are handled automatically by the robotic surgical system being controlled by the surgeon. For example, a surgeon may manually control the rate of drilling by physically manipulating the position of the drill bit while the robotic surgical system controls (e.g., alters) characteristics of rotation of the drill bit. Robotic surgical systems may be capable of operation in a fixed trajectory or fixed position mode (e.g., to reduce or eliminate unwanted motion of surgical instruments) or may be freely manipulated by a surgeon. Description of exemplary robotic surgical systems and components for use with such systems is provided below.

Figure 51:
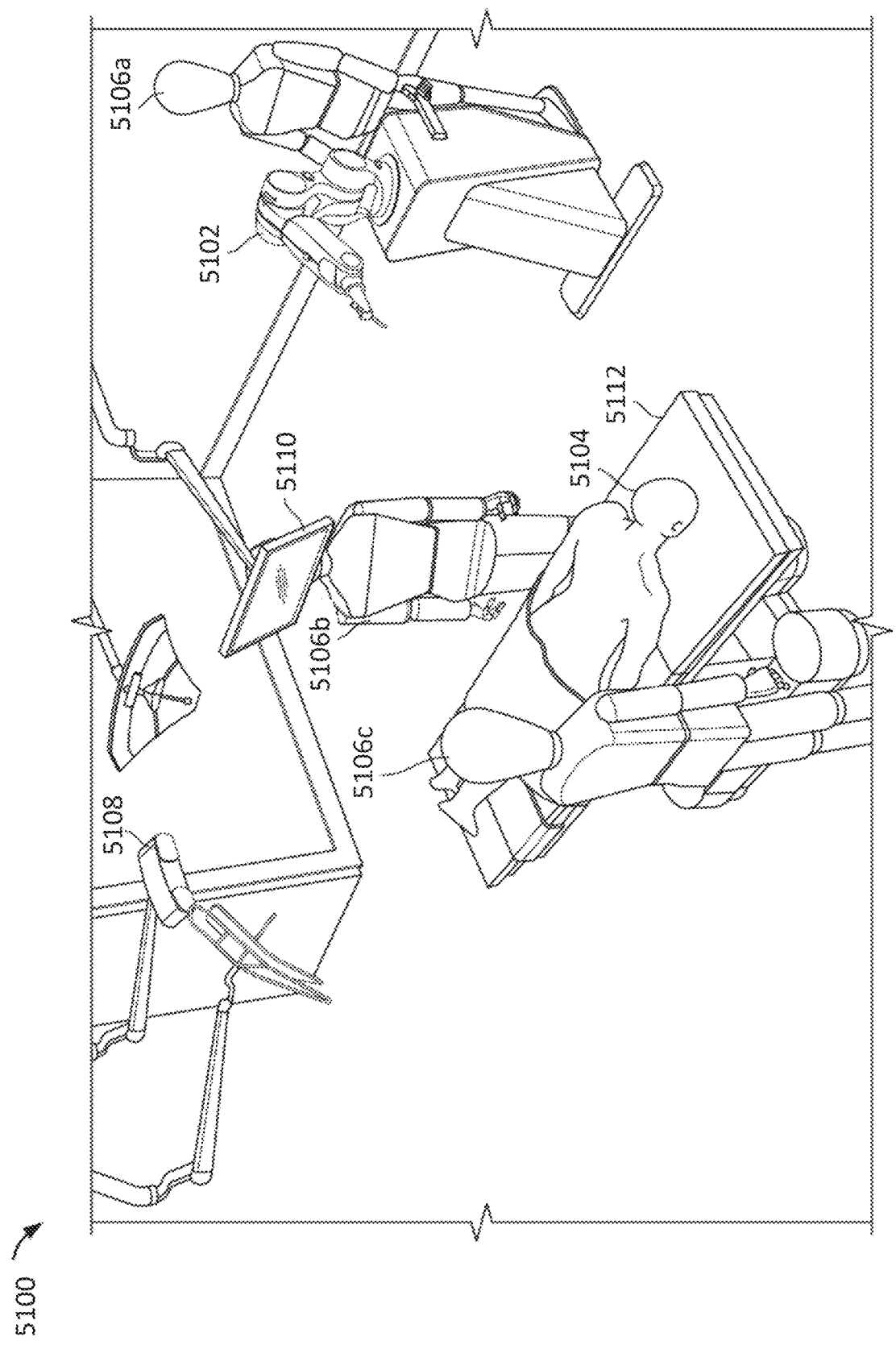
FIG. 51 is an illustration of a robotic surgical system in an operating room, according to illustrative embodiments of the invention.

FIG. 51 illustrates an example robotic surgical system in an operating room 5100 (e.g., for use in method disclosed herein). In some implementations, one or more surgeons, surgical assistants, surgical technologists and/or other technicians, (5106a-c) perform an operation on a patient 5104 using a robotic-assisted surgical system. In the operating room the surgeon may be guided by the robotic system to accurately execute an operation. This may be achieved by robotic guidance of the surgical tools, including ensuring the proper trajectory of the tool (e.g., drill or screw). In some implementations, the surgeon defines the trajectory intra-operatively with little or no pre-operative planning. The system allows a surgeon to physically manipulate the tool holder to safely achieve proper alignment of the tool for performing crucial steps of the surgical procedure. Operation of the robot arm by the surgeon (or other operator) in force control mode permits movement of the tool in a measured, even manner that disregards accidental, minor movements of the surgeon. The surgeon moves the tool holder to achieve proper trajectory of the tool (e.g., a drill or screw) prior to operation or insertion of the tool into the patient. Once the robotic arm is in the desired position, the arm is fixed to maintain the desired trajectory. The tool holder serves as a stable, secure guide through which a tool may be moved through or slid at an accurate angle. Thus, the disclosed technology provides the surgeon with reliable instruments and techniques to successfully perform his/her surgery.

In some embodiments, the operation may be spinal surgery, such as a discectomy, a foraminotomy, a laminectomy, or a spinal fusion. In some implementations, the surgical robotic system includes a surgical robot 5102 on a mobile cart. The surgical robot 5102 may be positioned in proximity to an operating table 5112 without being attached to the operating table, thereby providing maximum operating area and mobility to surgeons around the operating table and reducing clutter on the operating table. In alternative embodiments, the surgical robot (or cart) is securable to the operating table. In certain embodiments, both the operating table and the cart are secured to a common base to prevent any movement of the cart or table in relation to each other, even in the event of an earth tremor.

The mobile cart may permit a user (operator) 5106a, such as a technician, nurse, surgeon, or any other medical personnel in the operating room, to move the surgical robot 5102 to different locations before, during, and/or after a surgical procedure. The mobile cart enables the surgical robot 5102 to be easily transported into and out of the operating room 5100. For example, a user 5106a may move the surgical robot into the operating room from a storage location. In some implementations, the mobile cart may include wheels, a track system, such as a continuous track propulsion system, or other similar mobility systems for translocation of the cart. The mobile cart may include an attached or embedded handle for locomotion of the mobile cart by an operator.

For safety reasons, the mobile cart may be provided with a stabilization system that may be used during a surgical procedure performed with a surgical robot. The stabilization system increases the global stiffness of the mobile cart relative to the floor in order to ensure the accuracy of the surgical procedure. In some implementations, the wheels include a locking system that prevents the cart from moving. The stabilizing, braking, and/or locking system may be activated when the machine is turned on. In some implementations, the mobile cart includes multiple stabilizing, braking, and/or locking systems. In some implementations, the stabilizing system is electro-mechanical with electronic activation. The stabilizing, braking, and/or locking system(s) may be entirely mechanical. The stabilizing, braking, and/or locking system(s) may be electronically activated and deactivated.

In some implementations, the surgical robot 5102 includes a robotic arm mounted on a mobile cart. An actuator may move the robotic arm. The robotic arm may include a force control end-effector configured to hold a surgical tool. The robot may be configured to control and/or allow positioning and/or movement of the end-effector with at least four degrees of freedom (e.g., six degrees of freedom, three translations and three rotations). In some implementations, the robotic arm is active and non-backdriveable. Such an active and nonbackdriveable robotic arm comprises a force sensor.

Upon detection of a force applied to the end-effector that exceeds a predetermined minimum force, a processor of the robotic surgical system is instructed to control an actuator of the robotic arm to move the end-effector (e.g., in a direction corresponding to a direction of application of the force) at a predetermined measured pace (e.g., at a steady, slow velocity, or at an initially very slow velocity, gradually increasing in a controlled manner to a greater velocity) for positioning of the surgical tool position and/or end-effector position. In certain embodiments, the motion of an active non-backdriveable robotic arm is controlled by one or more motors that facilitate the end-effector moving at a predetermined measured pace in response to force applied by a surgeon.

Figure 54C:
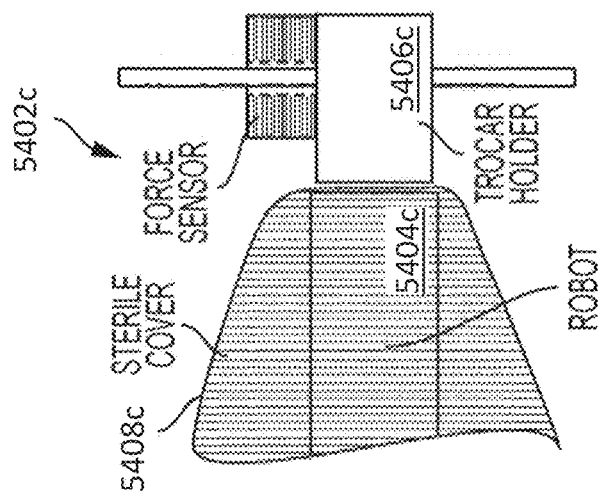
FIGS. 54A through 54C are illustrations of force sensor implementations, according to illustrative embodiments of the invention.
Figure 54B:
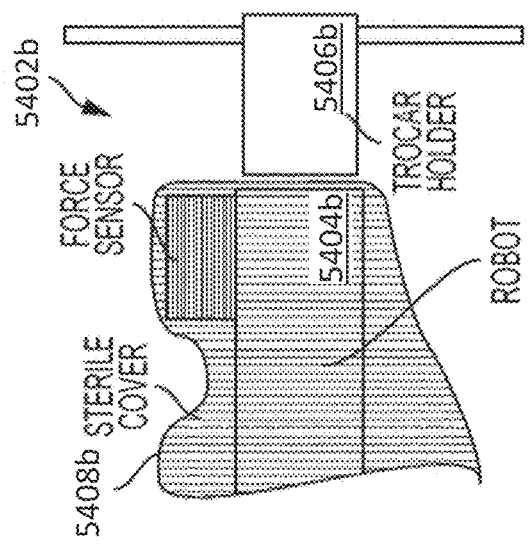
Figure 54A:
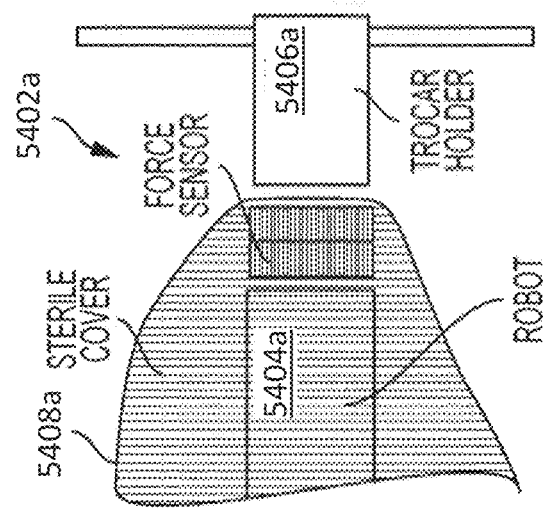

FIGS. 54A-C illustrate example locations for mounting a force sensor to detect forces applied to the end-effector (e.g., to receive haptic feedback). In some implementations, as shown in FIG. 54A, the force sensor 5402 a is located between the tool holder 5406 a and robot 5404 a. Using this configuration, the sterile cover 5408 a may be wrapped around the robot arm and between the force sensor and the tool holder to ensure sterilization. The force sensor 5402 a may provide for direct measurement of forces (e.g., forces and/or torques) on the tool. The force sensor 5402 a may be designed to resist flexing. The force sensor 5402 a may be designed to flex under the stress of certain external forces. The displacement caused when an external force is applied may be calculated based on the force and/or torque applied to the tool, radial force stiffness, axial torque stiffness, and the diameter of the holder to which the tool is attached.

As shown in FIGS. 54B and 54C, respectively, the force sensor (e.g., 5402 b in FIG. 54B or 5402 c in FIG. 54C) may be located on the robot or the tool holder, respectively. These configurations may exclusively measure the forces and/or torques applied by the user. The force sensor 5408 may be connected to the robot with an intermediary analog box which measures forces and torques and transmits them via a network (e.g., Ethernet, CAN, wireless, internet, private LAN, public LAN, etc.). Combinations of the above mentioned force sensor positions are possible to achieve predefined behavior (e.g. the first sensor in the base FIG. 54A and the second one in the handle FIG. 54B may be positioned to allow the feedback control system to decouple forces applied to the surgical tool from forces and/or torque applied by a user).

Figure 55:
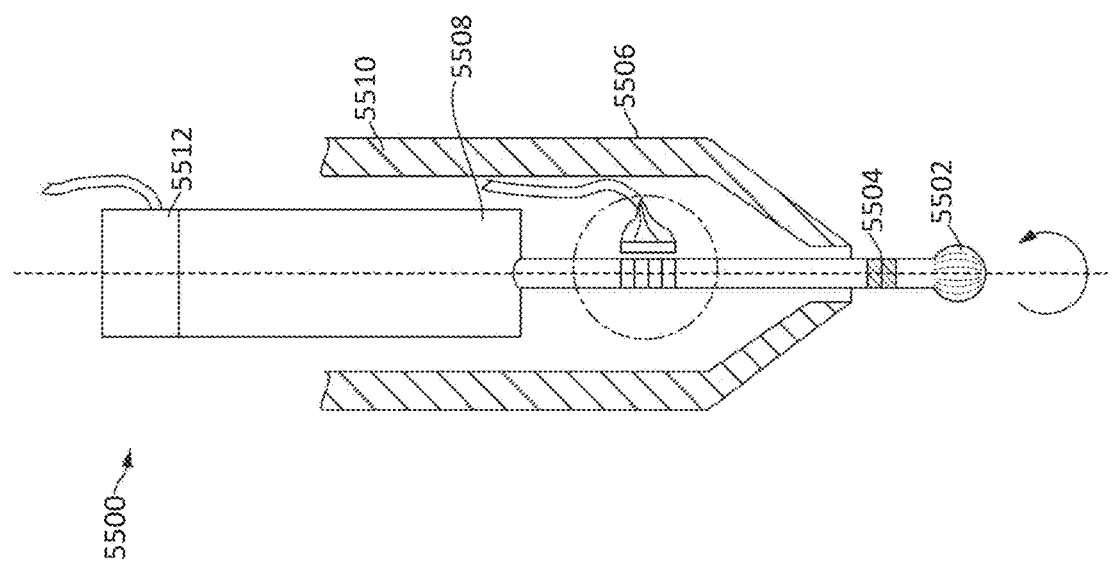
FIG. 55 is an illustration of a surgical instrument, according to illustrative embodiments of the invention.

Additionally, in some implementations the force sensor is integrated directly in the surgical instrument. For example, the force sensor may be integrated directly in the surgical drill bit as illustrated in FIG. 55. While the implementation of the force sensor 5504 is described in relation to a drill bit 5502 as shown in FIG. 55, the force sensor 5504 may be similarly integrated in other surgical instruments. Integrating the force sensor 5504 in a surgical instrument, such as a drill bit 5502, may be more robust as it minimizes the impact of external disturbances for measuring forces applied to the drill bit.

In the example configuration shown in FIG. 55, the force sensor 5504 is integrated in the shaft of the drill bit 5502. The force sensor 5504, in some implementations, is located on the drill bit 5502 outside of the body 5510 of the drill as shown in FIG. 55. In other implementations, the force sensor 5504 is located inside the body 5510 of the drill, thereby better protecting the force sensor 5504 from external influences. Force sensor can have multiple degrees of freedom and measure, for example, 1 to 3 forces and/or 1 to 3 torques. Forces are transmitted from the rotating shaft through a connector 5506. The connector, in some implementations, is one or more brushes that provide an electrical connection to the force sensor 5504. If the force sensor is an optical sensor, the connector may be an optical transmitter (e.g. LED) and/or optical receiver (e.g., photodiode). In this example, the brushes contact the drill bit thereby forming an electrical connection with the force sensor 5504. In some implementations, the brushes touch one or more contacts on the drill bit to form the electrical connection.

An electric or pneumatic motor 5508 rotates the drill bit 5502 shaft. In some implementations, a sensor 5512 (e.g., an encoder) measures position of the shaft. The sensor 5512 measures the position of the shaft in order to correlate forces measured by the force sensor to the relative position of the shaft. For example, if the force sensor is located in a drill bit, the measurement of the direction of the force will vary as the drill bit rotates. Specifically, the force sensor measures force and the direction of the force periodically (e.g., every millisecond, every microsecond, or somewhere therebetween). The drill bit rotates as the surgeon pushes it into bone. When the drill contacts the bone, the force sensor will indicate some force (F1) in a direction (D1). One period later (e.g., one millisecond), the drill bit will rotate slightly so the force sensor will indicate force of the same value (F1) (assuming a constant force is applied) in a different direction (D2). The direction of the force will continue to change relative to a single perspective as the drill bit rotates even if surgeon pushes into the bone with a constant force. A constantly changing force direction is not acceptable. In order to correlate the directions (e.g., D1, D2) with the global direction of the force (D) coming from the bone (seen by the surgeon, robotic system etc.) the position of the drill in the global space must be calculated as the drill bit rotates. The sensor 5512 is used to measure the position of the shaft and thus determine the global direction of the force (D). The sensor 5512 may be located on the back of the motor 5508 as shown in FIG. 55. The sensor 5512 may be located in other locations relative to the motor 5508 as well.

The force sensor 5504 may be provided in various configurations as shown in FIGS. 56A-D. In each configuration, the goal is to measure forces on the tip of the tool (e.g., drill bit ultrasound bit, etc.). In the example shown in FIG. 56A the force sensor 5504 is integrated in the shaft of the drill bit 5502 as described in relation to FIG. 55. The force sensor 5504 may communicate with a connector 5506 (shown in FIG. 55) via a sensor cable 5602. The sensor cable 5602, in some implementations, is routed inside the drill bit 5502. In some implementations, the connector 5506 (shown in FIG. 55) is electrically connected to the sensor cable 5602 via one or more connection pads.

The force sensor 5504 in this example may be a miniaturized industrial sensor (e.g., the multi-axis force/torque sensor from ATI Industrial Automation, Inc. of Apex, N.C.) that measures, for example, all six components of force and torque using a transducer. Alternatively, the force sensor 5504 may be an optical sensor. Alternatively, the force sensor 5504 may comprise a strain gauge 5606 integrated directly into the shaft of the drill bit 5502 as shown in FIG. 56B.

As shown in FIG. 56C, the force sensor 5504, in some implementations, measures forces on the motor instead of measuring forces on the drill bit 5502 itself. As shown in FIG. 56D, the shaft of the drill bit 5502, in some implementations, includes a flexible element 5608 that allows the drill bit 5502 to bend (e.g., only slightly) such that after deflection of the shaft of the drill bit 5502, forces can be measured by the force sensor 5504. In some implementations, for the configuration shown in FIGS. 56C and 56D, the measurement of shaft positions (e.g., by sensor 5512 as shown in FIG. 55) may be omitted as the forces are measured directly in the instrument coordinate frame.

In some implementations, the robotic arm is configured to releasably hold a surgical tool, allowing the surgical tool to be removed and replaced with a second surgical tool. The system may allow the surgical tools to be swapped without re-registration, or with automatic or semi-automatic re-registration of the position of the end-effector.

In some implementations, the surgical system includes a surgical robot 5102, a tracking detector 5108 that captures the position of the patient and different components of the surgical robot 5102, and a display screen 5110 that displays, for example, real time patient data and/or real time surgical robot trajectories.

In some implementations, a tracking detector 5108 monitors the location of patient 5104 and the surgical robot 5102. The tracking detector may be a camera, a video camera, an infrared detector, field generator and sensors for electromagnetic tracking or any other motion detecting apparatus. In some implementation, based on the patient and robot position, the display screen displays a projected trajectory and/or a proposed trajectory for the robotic arm of robot 5102 from its current location to a patient operation site. By continuously monitoring the patient and robotic arm positions, using tracking detector 5108, the surgical system can calculate updated trajectories and visually display these trajectories on display screen 5110 to inform and guide surgeons and/or technicians in the operating room using the surgical robot. In addition, in certain embodiments, the surgical robot 102 may also change its position and automatically position itself based on trajectories calculated from the real time patient and robotic arm positions captured using the tracking detector 108. For instance, the trajectory of the end-effector can be automatically adjusted in real time to account for movement of the vertebrae or other part of the patient during the surgical procedure.

Figure 52:
FIG. 52 shows a navigation screen that may be viewed by a surgeon or surgical staff during a spinal procedure in order to visualize the position, orientation, and trajectory of a surgical instrument guide relative to a patient's anatomy, according to illustrative embodiments of the invention.

FIG. 52 shows an exemplary navigation screen as viewed by a surgeon or surgical staff during a spinal procedure. Three of the four panels show radio images of the patient's anatomy with an overlay showing the position of a surgical instrument guide with its tool center point highlighted and a line segment emanating from the tool center point demonstrating the current trajectory of the surgical instrument guide or any surgical instrument guided therethrough. The fourth panel shows a 3D reconstruction of the patient's spine with a rendering of the surgical instrument guide shown to further acclimate the surgeon and surgical staff to the current position, orientation, and trajectory of the surgical instrument guide. Such a display changes as the position or orientation of the universal surgical instrument guide are updated by manipulation of the robotic arm by the surgeon. The surgeon may consult the current projected trajectory, position, or orientation of the surgical instrument guide relative to the patient's anatomy to intraoperatively adjust the position of the robotic arm to update the trajectory, position, and/or orientation of surgical instrument guide (and any surgical instrument inserted therethrough).

The disclosed technology may include a robot-based navigation system for real-time, dynamic registration and re-registration of a patient position (e.g., position of vertebrae of a patient) during a procedure (e.g., surgical procedure, e.g., a spinal surgery). An example robotic surgical system is shown in FIG. 53. The robotic surgical system 5300 includes a robotic arm 5302. The robotic arm can have 3, 4, 5, 6, or 7 degrees of freedom. The robotic arm 5302 has an end effector 5304.

In certain embodiments, the robotic arm 5302 includes a position sensor 5306 for dynamically tracking a position of the end effector 5304 and/or surgical instrument during a surgical procedure. Additionally, one or more points of the surgical instrument can be dynamically tracked, for example, at a rate of at least 100 Hz, 250 Hz or greater, 500 Hz or greater, or 1000 Hz or greater (e.g., position determination per second).

In certain embodiments, the system 5300 includes a force feedback subsystem 5308. The force feedback subsystem 5308 can include sensor(s), actuator(s), controller(s), servo(s), and/or other mechanisms for delivering a haptic force to a user manipulating the end effector or a surgical instrument inserted in the instrument holder of the end effector. The force feedback subsystem 5308 can detect the resistive force caused by the surgical instrument contacting, moving against, penetrating, and/or moving within a tissue of the patient. Furthermore, the force feedback subsystem 5308 can distinguish between contacted tissue types (e.g., determining when contacted tissue meets or exceeds a threshold resistance, e.g., when the tissue is bone).

The force feedback subsystem 5308 can also detect a force delivered by the operator. For example, it can detect forces delivered by direct manipulation of the surgical instrument inserted in the surgical instrument holder of the end effector to cause movement of the surgical instrument and, therefore, the end effector. The force feedback subsystem 5308 can further distinguish between the force delivered by the operator and the resistive force caused by movement of the surgical instrument in relation to the tissue of the patient. This allows the operator to both apply forces to the system as well as feel resistance (e.g., via haptic feedback) as a surgical instrument contacts tissue in the patient.

In certain embodiments, the robotic surgical system 5300 includes a display 5310 that is attached to, embedded within, or otherwise positioned in relation to the robotic arm being directly manipulated by the operator (e.g., surgeon) to allow for unimpeded visual feedback to the operator during the procedure.

When an operator uses the system, the system initially accesses (e.g., and graphically renders on the display) an initial registration of a target volume, such as a vertebra of the patient. This can be accomplished using medical images of the patient, including MRI, CT, X-rays, SPECT, ultrasound, or the like in accordance with the methods described herein below. These images can be obtained preoperatively or intraoperatively.

As the operative moves the position of the end effector, the position of the end effector is dynamically determined (e.g., by processor 5312). Specifically, in some implementations, the system dynamically determines a 3D position of one or more points of a surgical instrument. Forces received by the surgical instrument are dynamically determined when the surgical instrument contacts, moves against, penetrates, and/or moves within the patient. The system can measure these forces and distinguish between contacted tissue types. This can be accomplished, for example, by determining when contacted tissue meets or exceeds a threshold resistance, such as when the tissue is bone). The system can further detect forces applied to the surgical instrument by the operator and distinguish between forces delivered by the operator and the resistive force caused by movement of the surgical instrument in relation to the tissue of the patient.

In certain embodiments, the system can dynamically re-register the patient position based at least in part on an updated position of the end effector determined by the position sensor. This can be used to update the 3D representation of the patient situation based at least in part on the updated position of the end effector when it is determined (e.g., via the force feedback subsystem) that the surgical instrument is in contact with a target anatomy. This can be accomplished using a surface matching algorithm keyed to the initial (or previous) registration.

For example, the system can dynamically re-register the patient position upon detected contact or proximity of the end effector, or the surgical instrument, or a portion or component of the surgical instrument or end effector, with a pre-planned fiducial, such as a mechanical marker, a marker fixed to the patient. Alternatively, the system can dynamically re-register the patient position based upon the updated position of the end effector determined upon operator command, such as the operator pressing a button or otherwise activating a graphical or tactile user interface when a re-registered representation is desired.

A surgical instrument holder can be connected to the end effector for insertion or attachment of a surgical instrument therein/thereto. The instrument holder can be removable. In such instances, attachment of the instrument holder to the end effector is precise and predictable such that it is always connected in the same position.

The robotic arm is designed to allow direct manipulation of a surgical instrument by an operator (e.g., by a surgeon) when the surgical instrument is inserted in/attached to the surgical instrument holder of the end effector. The manipulation of the instrument can be subject to haptic constraints based on the position of the end effector (and/or the surgical instrument) in relation to the patient. The surgical instrument has a known geometry and position in relation to the surgical instrument holder such that the location of the instrument (e.g., the tip of the instrument) is known by the robotic surgical system. For example, when a surgical instrument is fully inserted into the instrument holder, the position of the instrument is known to the robotic surgical system because the position of the end effector is known as well as information about the surgical instrument and the instrument holder.

In certain embodiments, a tool center point (TCP) facilitates precise positioning and trajectory planning for surgical instrument guides and surgical instruments inserted through or attached to the surgical instrument holder. Surgical instruments can be engineered such that when inserted into the surgical instrument holder, there is a defined tool center point with known coordinates relative to robotic arm. The origin of a coordinate system used to define the tool center point may be located at a flange of a robotic arm. It may additionally be located at any convenient to define point such as an interface, joint, or terminal aspect of a component of a robotic surgical system.

In certain embodiments, because the TCP is in a constant position relative to the robotic arm, regardless of whether a surgical guide or surgical instrument is being used with the surgical instrument holder, a surgeon can be provided visualization of the orientation, trajectory, and position of an instrument or instrument guide used with the surgical instrument holder. The use of engineered surgical instrument systems eliminates the need for navigation markers to be attached to the end of surgical guides or tools in order to precisely determine the position, orientation, and trajectory of a surgical instrument guide relative to a patient's anatomy.

Additionally, a navigation marker attached to surgical instrument holder can be used to track the position and orientation of the universal surgical instrument guide to update the position, orientation, and current trajectory based on manipulation of robotic arm by a surgeon. Additional information provided by patient imaging (e.g., CT data, radio imaging data, or similar) taken pre- or intra-operatively as well as navigation markers attached to a patient's body may be combined with data from a navigation marker attached to a universal surgical instrument guide and displayed on a screen viewable by the surgeon such that the surgeon can see the location of necessary features of the patient's anatomy and the position, trajectory, and orientation of a surgical instrument or surgical instrument guide relative to said anatomy.

Figure 49:
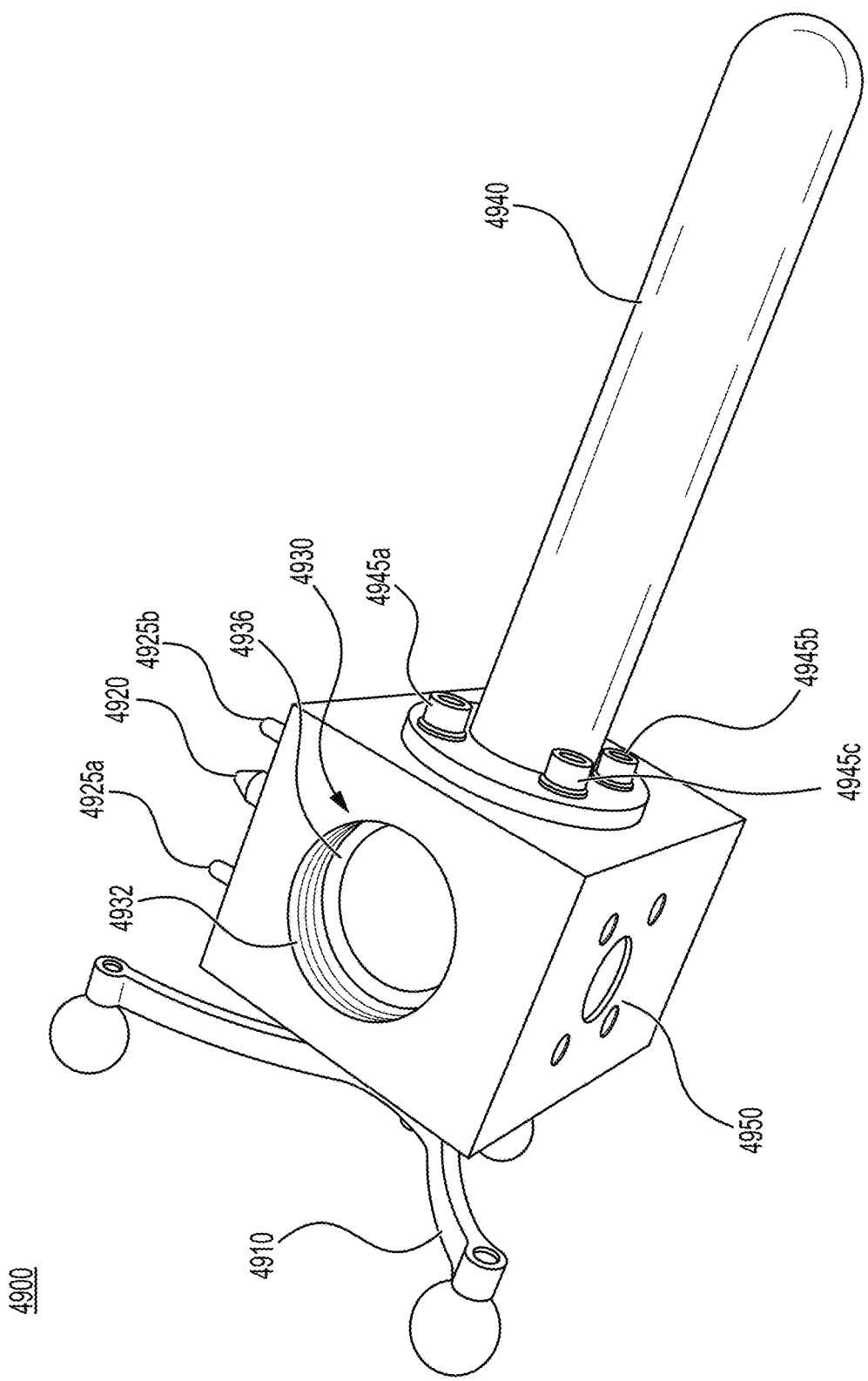
FIG. 49 shows a universal surgical instrument guide, according to illustrative embodiments of the invention.

FIG. 49 shows a universal surgical instrument guide 4900 for attachment to a robotic surgical system to assist in guiding surgical instruments used in preparing holes as described herein. Universal surgical instrument guide 4900 attaches to a proximal end of a robotic surgical system with high precision and rigidity using pins 4925*a-c* (pin 4925*c* not shown in FIG. 49) and threaded screw 4920. Threaded screw 4920 is accessed through first channel 4950. The attachment system is described in greater detail below. Second channel 4930 is sized for surgical instrument guides to be received therethrough such that a portion of the surgical instrument guides reside in the second channel 4930. Additionally, second channel 4930 has a threaded portion 4932 near one of its openings such that surgical instrument guides can engage the threaded portion 4932 to be securely held while in use. The distal end of the threaded portion 4932 of second channel 4930 has a lip 4936 to eliminate the possibility of over-threading a surgical instrument guide. Alternative temporary secure attachment means may be used with the second channel 4930 such as tension sleeves, pressure connections, quick connect type fittings, or similar. In some embodiments, surgical instruments are inserted directly through the second channel 4930 of a universal surgical instrument guide without the use of an additional surgical instrument guide. In those embodiments, surgical instruments may be appropriately threaded as to engage threads in the second channel 4930 of the body of a universal surgical instrument guide. First channel 4950 is shown to be oriented perpendicular to second channel 4930. In some embodiments of a universal surgical instrument guide, the first channel 4950 and second channel 4930 are non-parallel and not perpendicularly oriented.

Universal surgical instrument guide 4900 has sterile handle support member 4940. Sterile handle support member 4940 is attached to universal surgical instrument guide 4900 with fasteners 4945*a-d* (fastener 4945*d* not shown). Sterile handle support member 4940 is sized and shaped to accommodate a sterile handle assembly for gripping by a surgeon in order to manipulate the position of the end-effector of the robotic surgical system. Sterile handle support member 4940 is removably attached to universal surgical instrument guide 4900. Removable attachment can, for example, assist in sterilization of a universal surgical instrument guide and its handle support member. In some embodiments, robotic surgical systems comprise a manipulator for the end-effector located in an alternative location (i.e., not on the universal surgical instrument guide). Removable attachment of the handle support member 4940 additionally allows the support member 4940 to be removed from the robotic surgical system when it is not necessary as to not have an unnecessary obstruction on the universal surgical instrument guide 4900.

Navigation marker 4910 is attached to universal surgical instrument guide using a fastener inserted into an opening in the body of universal surgical instrument guide 4900 sized and shaped to receive such a fastener. Navigation marker 4910 can be any navigation marker suitable for tracking the position of a universal surgical instrument guide. Navigation marker 4910 comprises three navigation member elements that can be used to triangulating the position of the universal surgical instrument guide with high precision. In certain embodiments, a navigation marker may have more or less constituent navigation member elements (e.g., 2 or 4). In certain embodiments, the position of a navigation marker is tracked using a navigation camera, wherein the navigation camera is part of a robotic surgical system. In some embodiments, a navigation marker has more or less navigation member elements. Navigation marker 4910 is located on the opposite side of universal surgical instrument guide 4900 from handle support member 4940 to reduce the likelihood of the support member, any sterile handle attached thereto, and any part of a surgeon's body near the sterile handle during use from interfering with tracking of navigation marker 4910.

Fasteners used to attach navigation marker 4910 or handle support member 4940 to universal surgical instrument guide body or to attach the universal surgical instrument guide body to a robotic arm (i.e., fastener 4920) may be any fastener suitable to securely hold the respective components together. For example, the fastener may be an expansion fastener, screw, bolt, peg, flange or similar.

Figure 50:
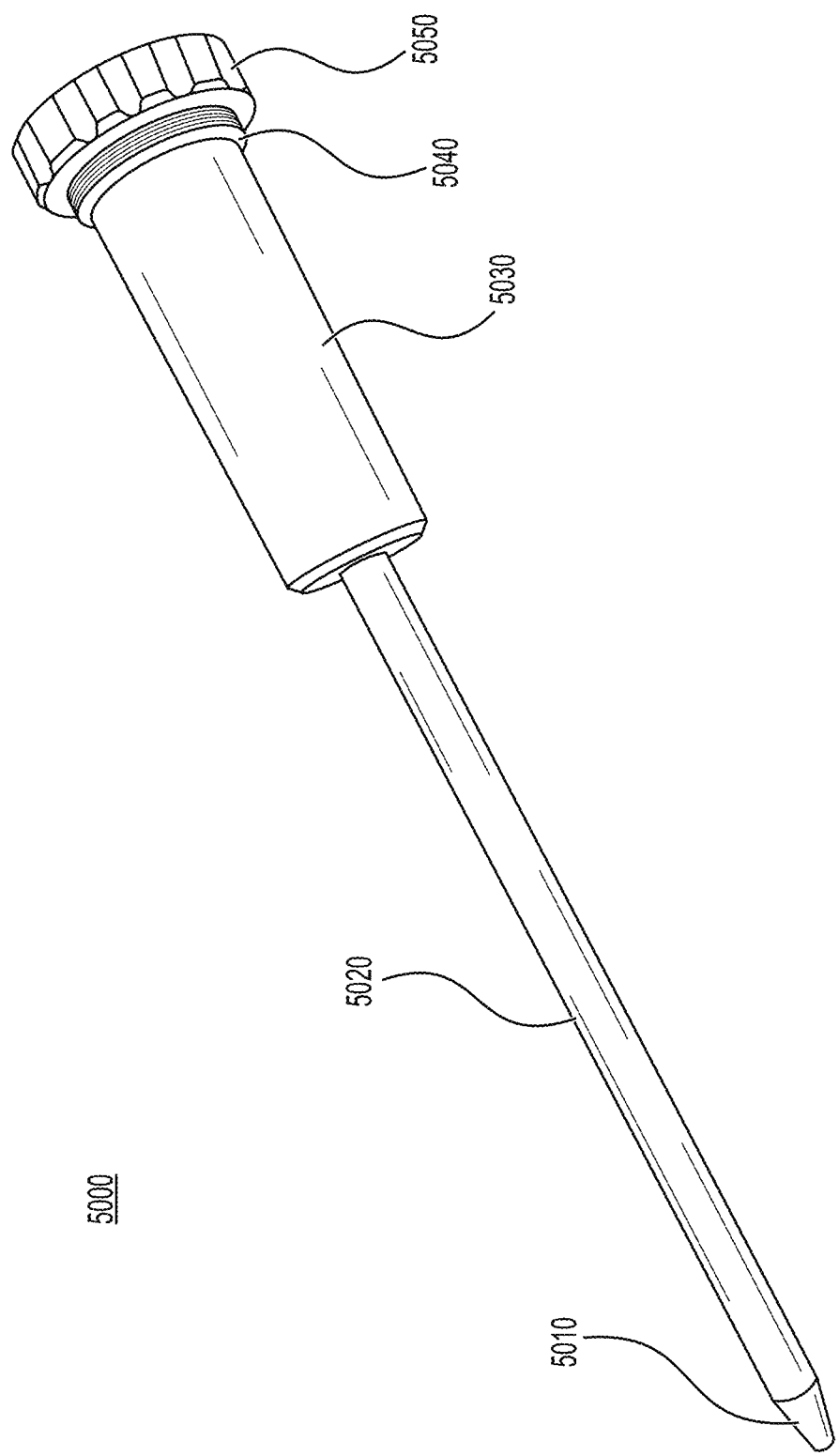
FIG. 50 shows a drill guide, according to illustrative embodiments of the invention.

FIG. 50 shows a drill guide 5000 engineered for use with a universal surgical instrument guide (e.g., the guide 4900 of FIG. 49). Drill guide 5000 comprises tapered end 5010, guiding shaft 5020, and a proximal portion comprising first exterior surface 5030, second exterior surface 5040, and collar 5050. Guiding shaft 5020 is sized such that the hollow internal portion of the shaft is of appropriate size to accommodate the stem of a drill bit. Guiding shaft 5020 runs from tapered end 5010 to the terminal aspect of the collar such that a drill bit enters drill guide 5000 at an opening near collar 5050 and exits drill guide 5000 at tapered end 5010 with its movement restricted along an axis along the long dimension of guiding shaft 520. First exterior surface 5030 is substantially in contact with a second channel (e.g., 4930) of a universal surgical instrument guide when drill guide 5000 is inserted therein such that drill guide 5000 cannot be easily deflected. Furthermore, threads on second exterior surface 5040 engage threads (e.g., 4932) of the universal surgical instrument guide's second channel such that drill guide 5000 is securely held by the universal surgical instrument guide. Collar 5050 can be gripped by a surgeon to thread drill guide 5000 into a universal surgical instrument guide and additionally acts as a limiter to prevent overthreading of drill guide 5000. Such a drill guide may be used in conjunction with a universal instrument guide (e.g., guide 4900 of FIG. 49) to provide guidance of a drill bit during hole preparation (e.g., during the methods disclosed herein).

FIG. 1 is an illustration of example prior art drill bits 102 and 104 and an additional exemplary surgical instrument guide 106 that may be used with robotic surgical system to prepare holes in bone. Typically, surgical instruments include a tapered end 114 that narrows to a point 116. The point 116 is used to guide the drill bit. Standard surgical instruments, especially drill bits, may skid on the surface of bone tissue which significantly decreases precision of the hole. The skidding can be linked with drill angle a which is not well adapted to drilling at an angle (different from the right angle) to the bone tissue surface. Given that the surface of most bones are not perfectly flat, standard drill bits often result in imprecise holes in the bone. For example, if the side of the drill (e.g., the side of the tapered tip 114 of the drill) touches the bone tissue before tip 116 of the drill bit has entered the tissue and provides guidance, drill skid is more likely.

Figure 2:
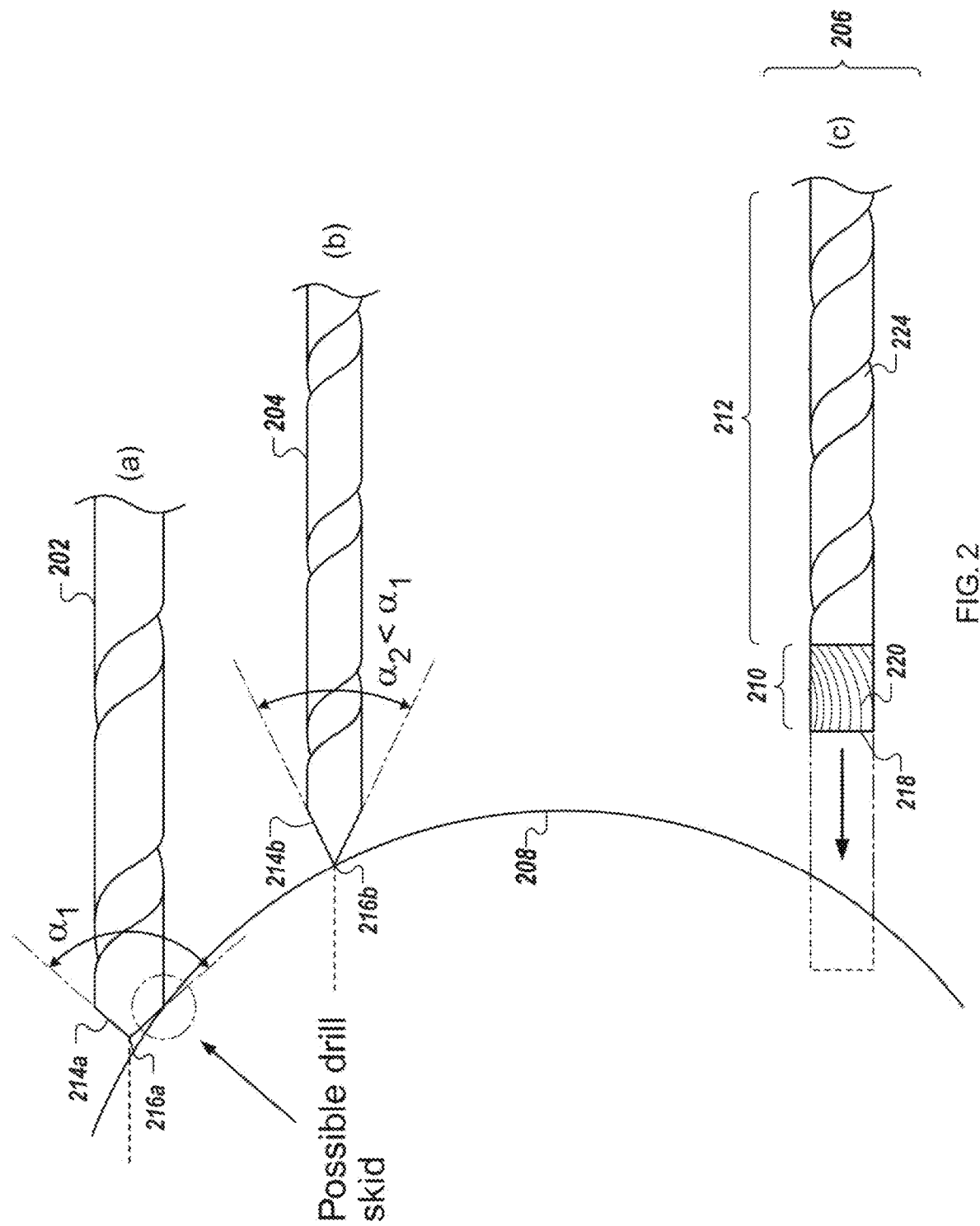
FIG. 2 is an illustration of example surgical instruments for preparing holes in bone tissue.

FIG. 2 is a comparison of three drill bits contacting the surface of bone tissue 208. As shown in FIG. 2, drill bit 202 is likely to skid because the tip 216*a* of the drill bit 202 will not contract the surface of the bone tissue 208 first. Instead, the side 214*a* of the tapered tip will contract the bone tissue 208 before the tip 216*a*. Relative to drill bit 202, the tip 216*b* of drill bit 204 is less likely to skid because the tip 216*b* of the drill bit 204 contracts the bone tissue 208 first. However, one of the reasons it is difficult to predict if and when a drill bit will skid during surgeries is the difficulty of determining whether the tip of the drill bit will contract the bone tissue 208 first. The anti-skid surgical instrument 206 as shown in FIG. 2 reduces the risk of drill bit skid because the "tip" is a flat milling surface 218 which is perpendicular to the surface of the body of the surgical instrument. The mill head 210 of the anti-skid surgical instrument 206 is adapted for milling (e.g., rather than drilling) when entering the bone tissue 208. The portion of the instrument body 212 after the head 210, in some implementations, is adapted for drilling (e.g., contains evacuating holes, spirals, twists, etc.).

In some implementations, the anti-skid surgical instrument 206 has a mill head 210 at the end of the elongate structure for removing bone tissue with reduced skidding (e.g., unintentional lateral movement of the surgical instrument) of the surgical instrument upon contact of the anti-ski surgical instrument with the bone tissue 208. The mill head 210 has a flat end 218 substantially perpendicular to a longitudinal axis of the elongate structure. In some implementations, the mill head 210 has one or more side-cutting flutes 220 (e.g., sharpened) about the longitudinal axis of the elongate structure for cutting into bone tissue. The one or more side cutting flutes 220 can include two, three, four, six, eight, ten, or twenty flutes.

In some implementations, the anti-skid surgical instrument 206 has a shank (not shown) for connection to a drill. In some implementations, the anti-skid surgical instrument 206 has a shaft 212 between the mill head 210 and the shank, the shaft 212 having one or more drill flutes 224 (e.g., non-cutting flutes; e.g., unsharpened) for evacuating removed bone tissue. In some implementations, the one or more drill flutes 224 include two, three, four, six, eight, ten, or twenty flutes. The one or more drill flutes 224 are different than the one or more side cutting flutes 220. For example, the drill flutes 224 may have a different (e.g., larger or smaller) twist rate, (e.g., flute angle) than the side cutting flutes 220.

In some implementations, the flat end 218 of the mill head 210 has one or more end cutting flutes (not shown) for cutting axially into the bone tissue. In some implementations, the one or more end cutting flutes are cutting teeth. Additionally, a longitudinal length of the shaft, in some implementations, is greater than a longitudinal length of the mill head. The longitudinal length of the shaft, in some implementations, is less than a longitudinal length of the mill head.

As shown in FIG. 2, the anti-skid surgical instrument 206 has an elongate structure with a mill head 210 with milling surface 218, a shaft 212 with a drill surface. In some implementations, the instrument 206 includes a second end, opposite the first end 210, with a shank configured to be grasped by a drill. The mill head 210 of the anti-skid surgical instrument 206 is flat and substantially perpendicular to the surface of the elongate structure, thereby reducing skidding (e.g., unintentional lateral movement of the surgical instrument 206) of the surgical instrument 206 upon contact of the milling surface 218 with bone tissue 208.

The mill end 210, in some implementations, utilizes rotary cutters to remove material. The mill end 210 can take the form of several shapes and sizes. For example, the mill end 210 can be an end mill, slab mill, or other types of milling devices.

The flutes 220 of the mill head 210, in some implementations, are deep helical grooves running up the cutter, while the sharp blade along the edge of the flute 220 is known as the tooth. The tooth cuts the material, and chips of this material are pulled up the flute 220 by the rotation of the cutter. In some implementations, there is one tooth per flute. In some implementations, there are two or more teeth per flute. For example, the cutter of each flute 220 may have 2, 3, 4, 5, or more teeth (e.g., 1-4, 5-10, or 10-20 teeth). Typically, the more teeth a cutter has, the more rapidly it can remove material. Thus, typically a 4-tooth cutter can remove material at twice the rate of a 2-tooth cutter. The mill head 210 may be an end mill with cutting teeth at one end (i.e., the flat end 218) and on the sides 220 of mill end 210. For example, the flat end 218 can be a flat bottom cutter.

In some implementations, the surgical instrument 206 is rigidly guided (e.g., by a robotic surgical system). The surgical instrument 206 may cause higher radial forces when entering bone tissue 208, thus a rigid guide ensures that the hole will be placed accurately. The drill used with the surgical instrument 206, in some implementations, is sufficiently rigid to avoid deflection of the drill itself. A high rotational velocity drill (e.g., power drill) may be used to reduce radial forces.

In certain embodiments, hole placement accuracy is achieved by the combination of the anti-skid drill bit and the robotic surgical system. The rigidity provided by the robotic surgical system along with the anti-skid drill bit allows precise drilling of holes, thereby minimizing (or eliminating) skiving along the bone upon contact between the bone and the anti-skid drill bit. The robotic surgical system provides rigidity from the floor of the operating room (and/or the surgical table) to the surgical instrument itself. This is achieved by each component within the "chain" providing rigidity. An example surgical system is described in U.S. Pat. No. 9,283,048, filed Apr. 30, 2014 and entitled "Apparatus, Systems, and Methods for Precise Guidance of Surgical Tools," the contents of which are hereby incorporated by reference in its entirety. In this example, the mobile cart is designed to rest on legs during surgery such that the robot is fixed in place. Further, the robotic arm is rigidly attached to the base and is an active arm. Similarly, the notched guide and the surgical instrument holder are designed to provide rigidity. Examples of notched guides are provided in U.S. Pat. No. 9,241,771, filed Jan. 15, 2015, entitled "Notched Apparatus for Guidance of an Insertable Instrument along an Axis during Spinal Surgery," which is hereby incorporated by reference in its entirety. Examples of surgical instrument holders are provided in U.S. Patent Application Publication No. 2015/0305817, filed Apr. 24, 2015, entitled "Surgical Instrument Holder for use with a Robotic Surgical System," which is hereby incorporated by reference in its entirety. The combination of the notched guide or surgical instrument holder, active robotic arm, and robot (e.g., robot base), along with the anti-skid drill bit, reduces skidding (e.g., skiving) when the drill bit contacts the bone, thereby allowing accurate placement of holes for surgical screws.

In some implementations, the surgical instrument 206 is used in combination with a robotic surgical system, such as the robotic surgical system described in U.S. Pat. No. 9,283,048, filed Apr. 30, 2014 and entitled "Apparatus, Systems, and Methods for Precise Guidance of Surgical Tools," the contents of which are hereby incorporated by reference in its entirety.

In some implementations, the surgical instrument 206 is used with a passive arm or any device that provides rigid fixation of the surgical instrument 206. The surgical instrument 206 may be insertable into a surgical instrument guide such that the surgical instrument 206 is constrained by the surgical instrument guide. The surgical instrument guide may include a rigid hollow tubular structure having a first open end and a second open end. The structure of the guide may define the axis along which movement of a surgical instrument sliding through the structure is restricted. The tubular structure may have an interior surface shaped and sized to accommodate the anti-skid surgical instrument 206 sliding through the guide such that movement of the surgical instrument 206 (e.g., fitted with a tool support) is constrained in all directions except along the axis defined by the guide. The surgical instrument 206 may be fitted with or have an integrated tool support such that the tool support engages the guide to provide accurate guidance of the surgical instrument 206. For example, the anti-skid surgical instrument 206 may be fitted with a tool support shaped and sized to slide through the surgical instrument guide along the axis defined by the guide.

In instances in which the surgical instrument 206 is guided by a robotic surgical system, the robotic surgical system may include a robotic arm. In some implementations, the robotic arm has an end effector including a surgical instrument guide attached thereto, the surgical instrument guide configured to hold and/or restrict movement of a surgical instrument therethrough. A navigation marker may be used to track the surgical instrument 206. The axis of the surgical instrument guide can be aligned with the desired trajectory in relation to the patient situation via the manipulator.

Figure 3:
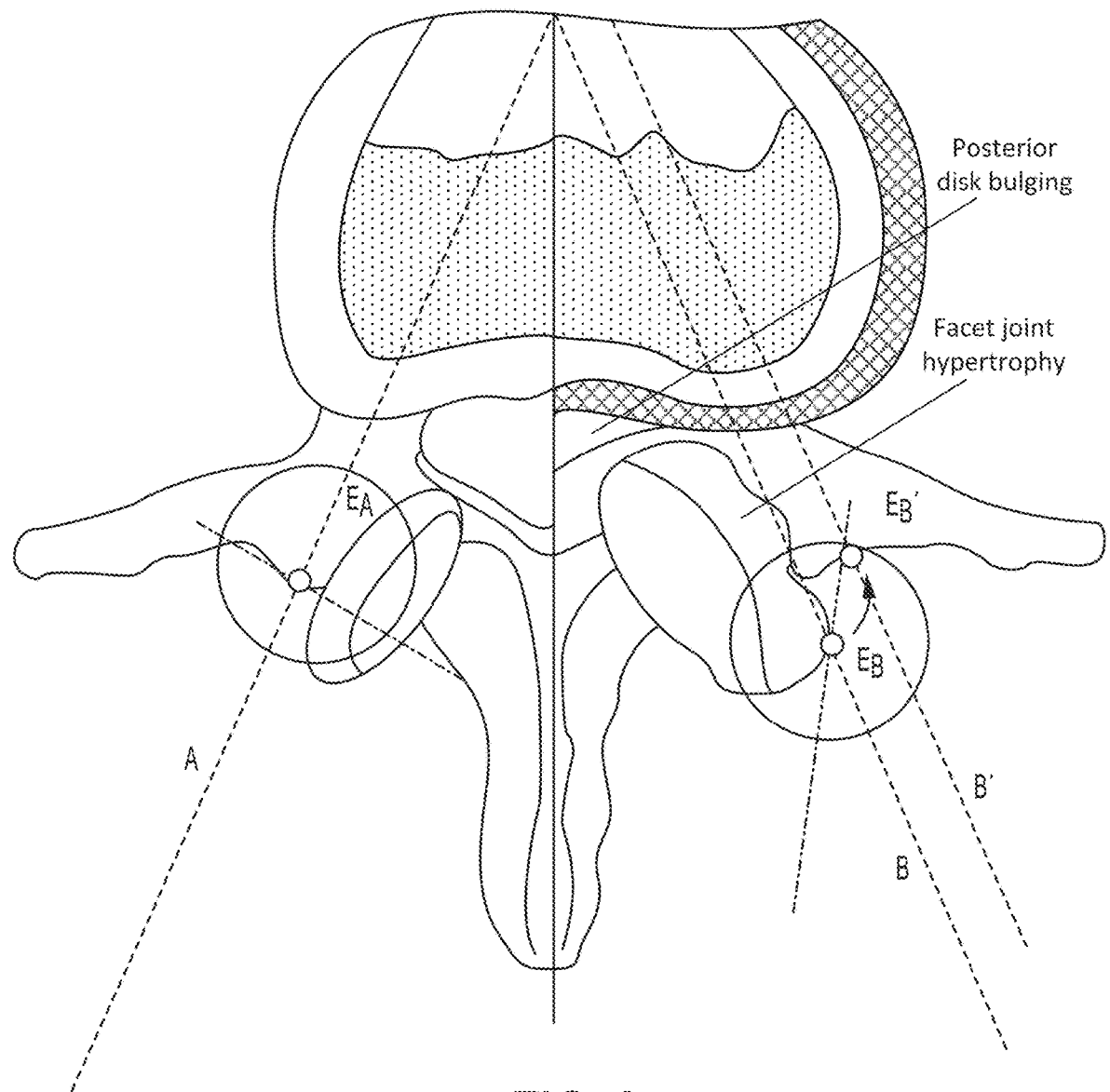
FIG. 3 illustrates why a drill bit skiving on the surface vertebrae can be particularly problematic for abnormal vertebrae (e.g. arthritic)

FIG. 3 illustrates why drill bit skiving on the surface vertebrae can be particularly problematic for abnormal vertebrae (e.g. arthritic). On the left side of the image, a "normal" vertebra is shown with standard trajectory A going through a pedicle. In this case entry point EA is located where surface of the bone is close to being perpendicular to drilling axis. This decreases the possibility of skiving.

In contrast, situation on the right side of the image shows an arthritic vertebrae (e.g., of an older person). Due to additional hard bony tissue, facet joint increases its volume and interferes with the trajectory. It places ideal entry point EB on the angled surface and increases chances of skiving. If skiving occurs, it will likely displace entry point to EB1. Instead of the trajectory being trajectory B, it likely will be trajectory B1 and might lead to screw implant going out of the pedicle. This can result in serious clinical consequences (neurologic, vascular, etc.) for the patient. It should be noted that in most operated patients arthritis appears at various levels of advancement (e.g., healthy patients would have surgery principally as a result of trauma only).

Figure 4:
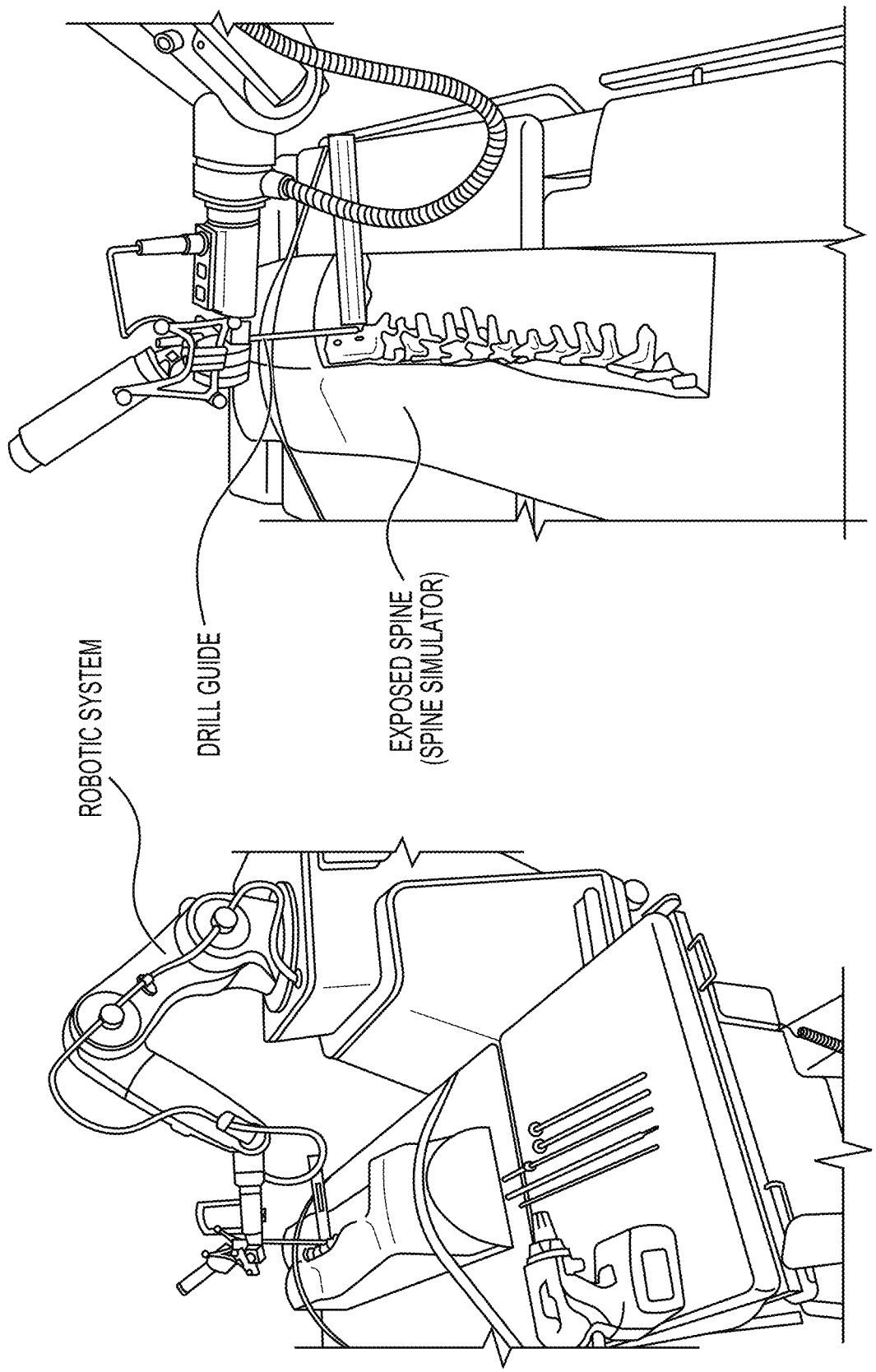
FIG. 4 is a still photographs taken during an experiment performed using the disclosed technology and standard drill bits to measure the amount of skiving experienced with different drill bit designs.

FIGS. 4 through 30 are still photographs taken during an experiment performed using the disclosed technology and standard drill bits to measure the amount of skiving experienced with different drill bit designs. As discussed above, a problem with drilling bone with traditional drill bits is drill skiving on the surface of the bone (e.g., vertebrae). The test setup is shown in FIG. 4. A robot and a drill guide were used to drill holes in simulated patient anatomy. An example robot that can be used with the disclosed technology is described in U.S. Pat. No. 9,283,048, filed Apr. 30, 2014 and entitled "Apparatus, Systems, and Methods for Precise Guidance of Surgical Tools," which is hereby incorporated by reference in its entirety. The patient's anatomy was simulated by a custom-made spine simulator which integrates bony tissue and foam representing soft tissue to provide a model with sufficient vertebrae mechanical behavior (resistance, elasticity, bone quality, etc.).

Figure 5:
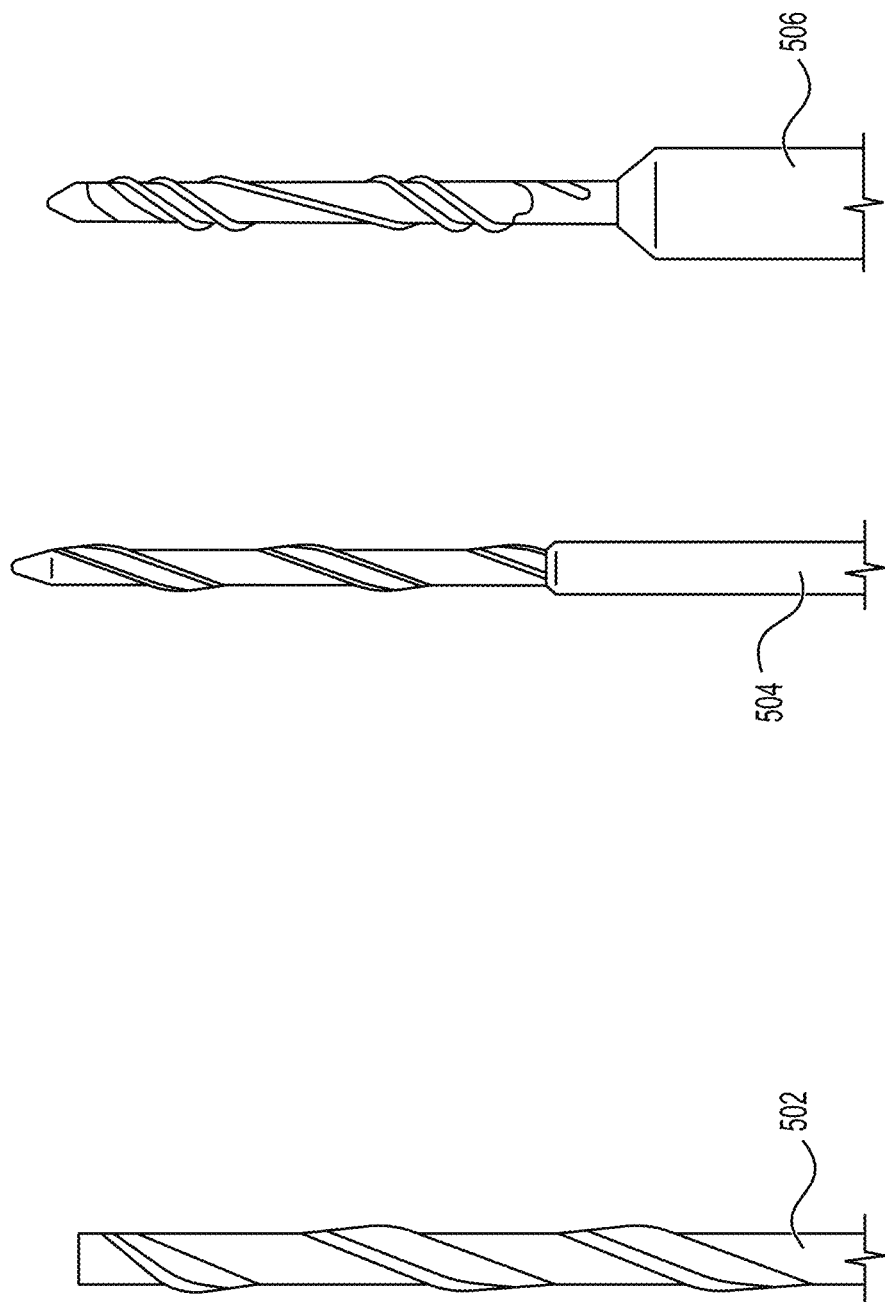
FIG. 5 is a still photographs taken during an experiment performed using the disclosed technology and standard drill bits to measure the amount of skiving experienced with different drill bit designs.
Figure 6:
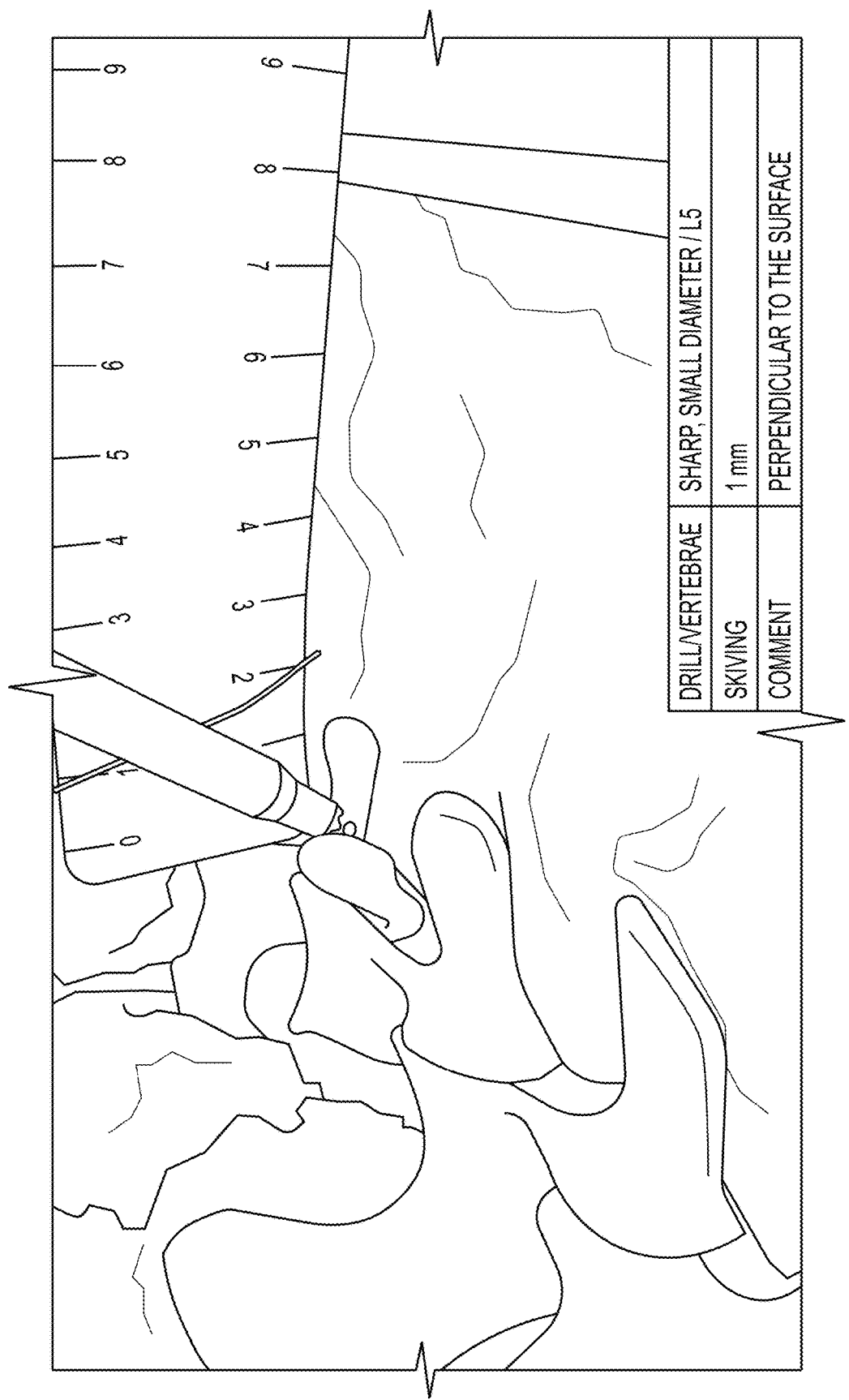
FIG. 6 is a still photographs taken during an experiment performed using the disclosed technology and standard drill bits to measure the amount of skiving experienced with different drill bit designs.
Figure 7:
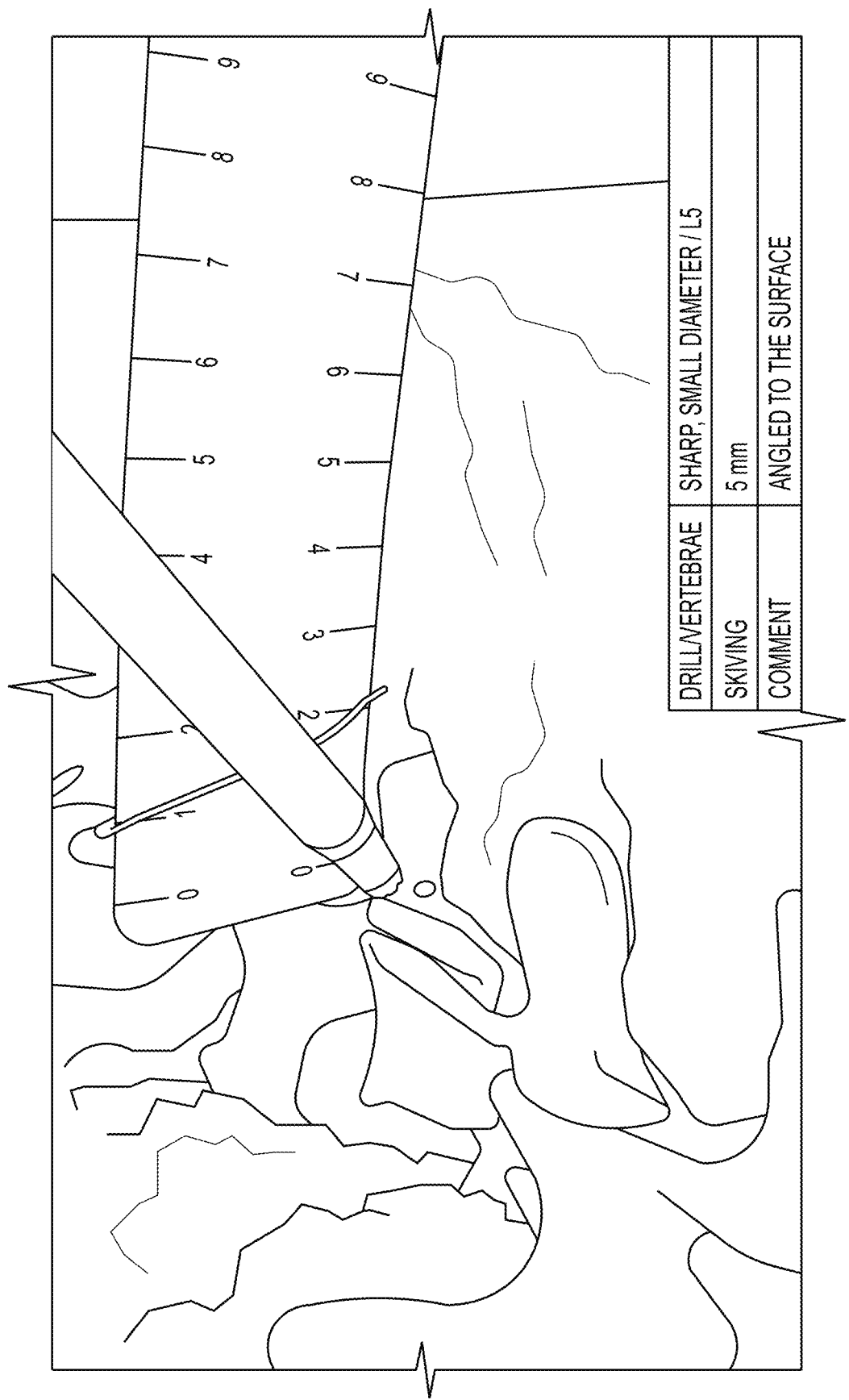
FIG. 7 is a still photographs taken during an experiment performed using the disclosed technology and standard drill bits to measure the amount of skiving experienced with different drill bit designs.
Figure 8:
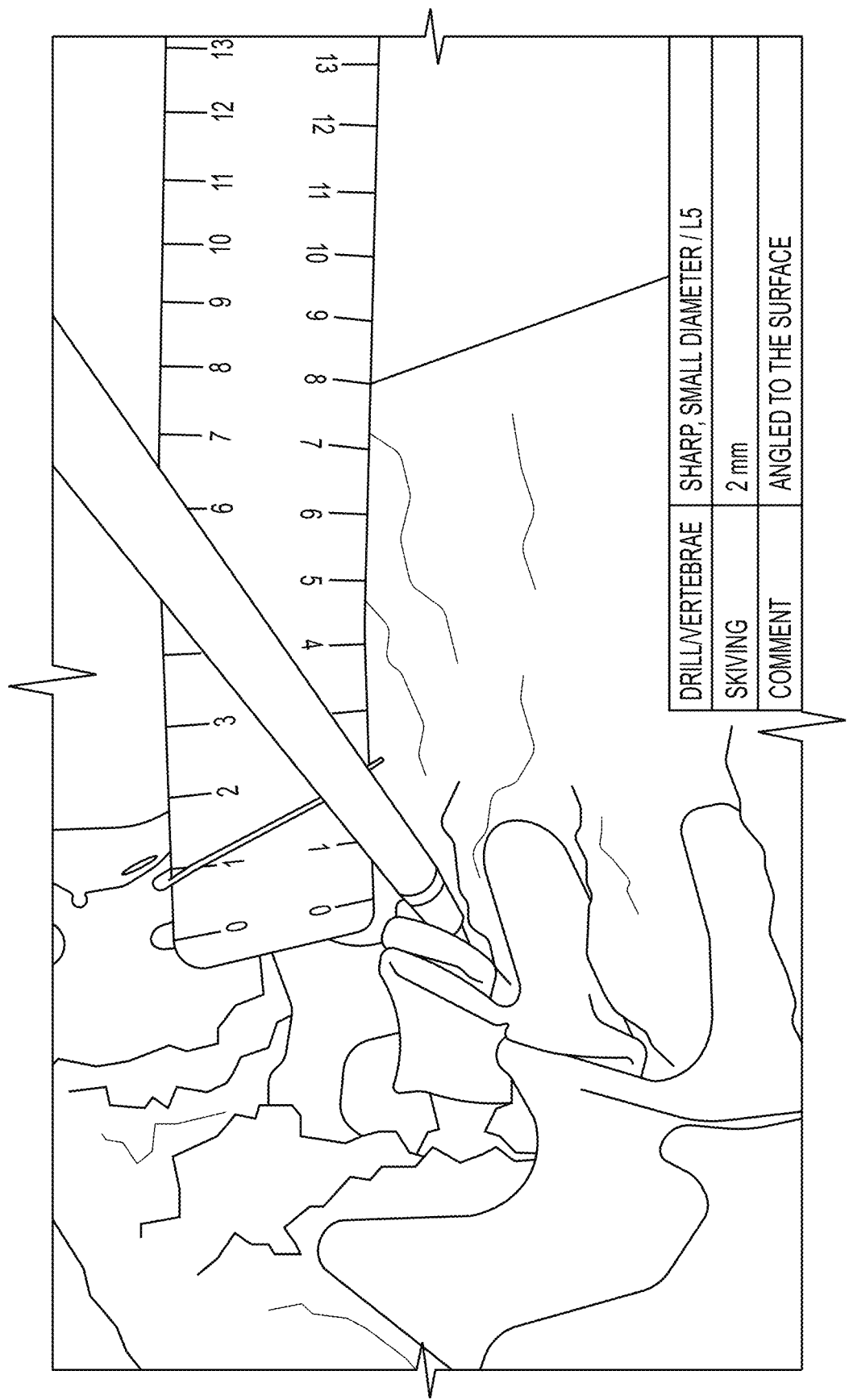
FIG. 8 is a still photographs taken during an experiment performed using the disclosed technology and standard drill bits to measure the amount of skiving experienced with different drill bit designs.
Figure 9:
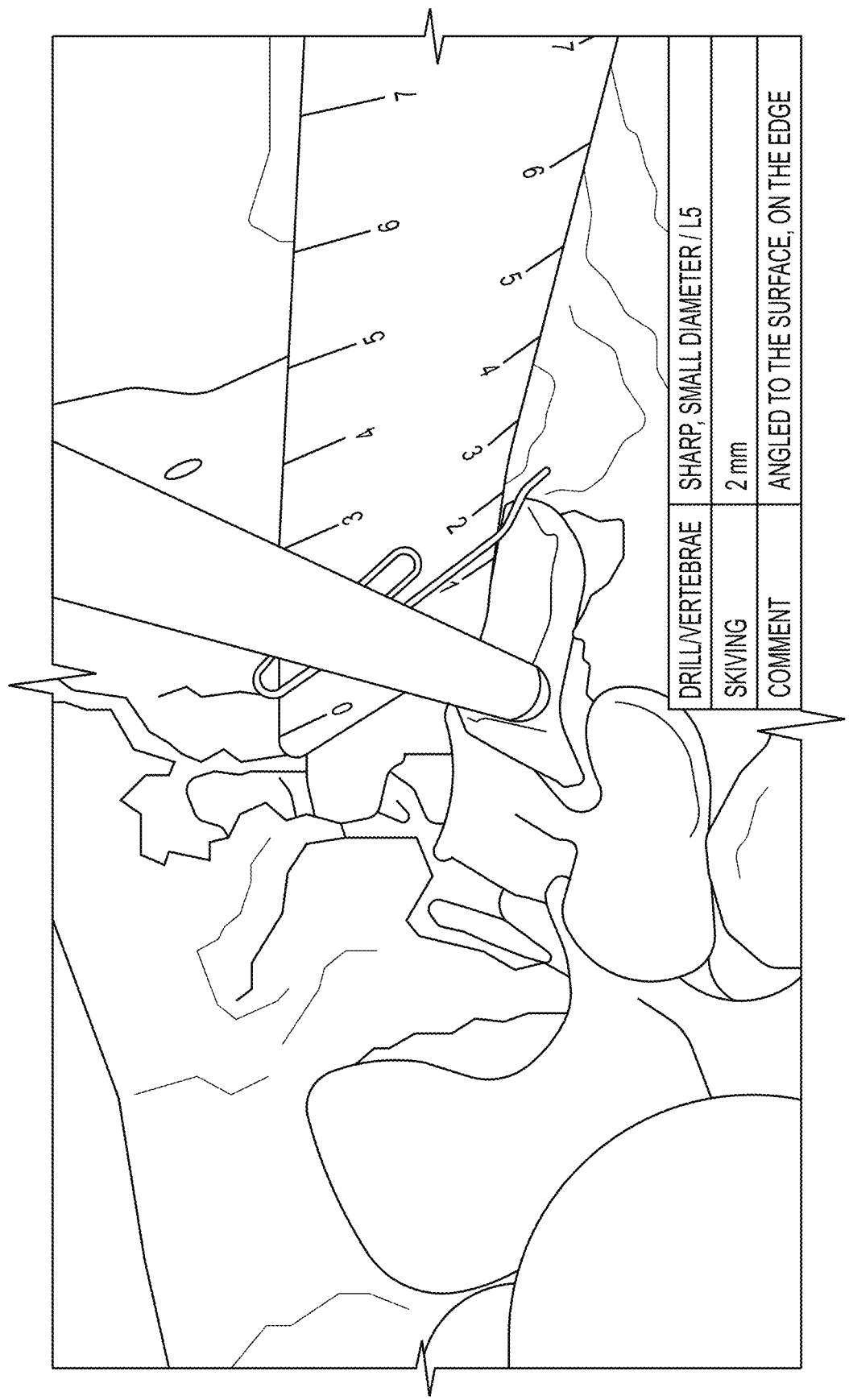
FIG. 9 is a still photographs taken during an experiment performed using the disclosed technology and standard drill bits to measure the amount of skiving experienced with different drill bit designs.
Figure 10:
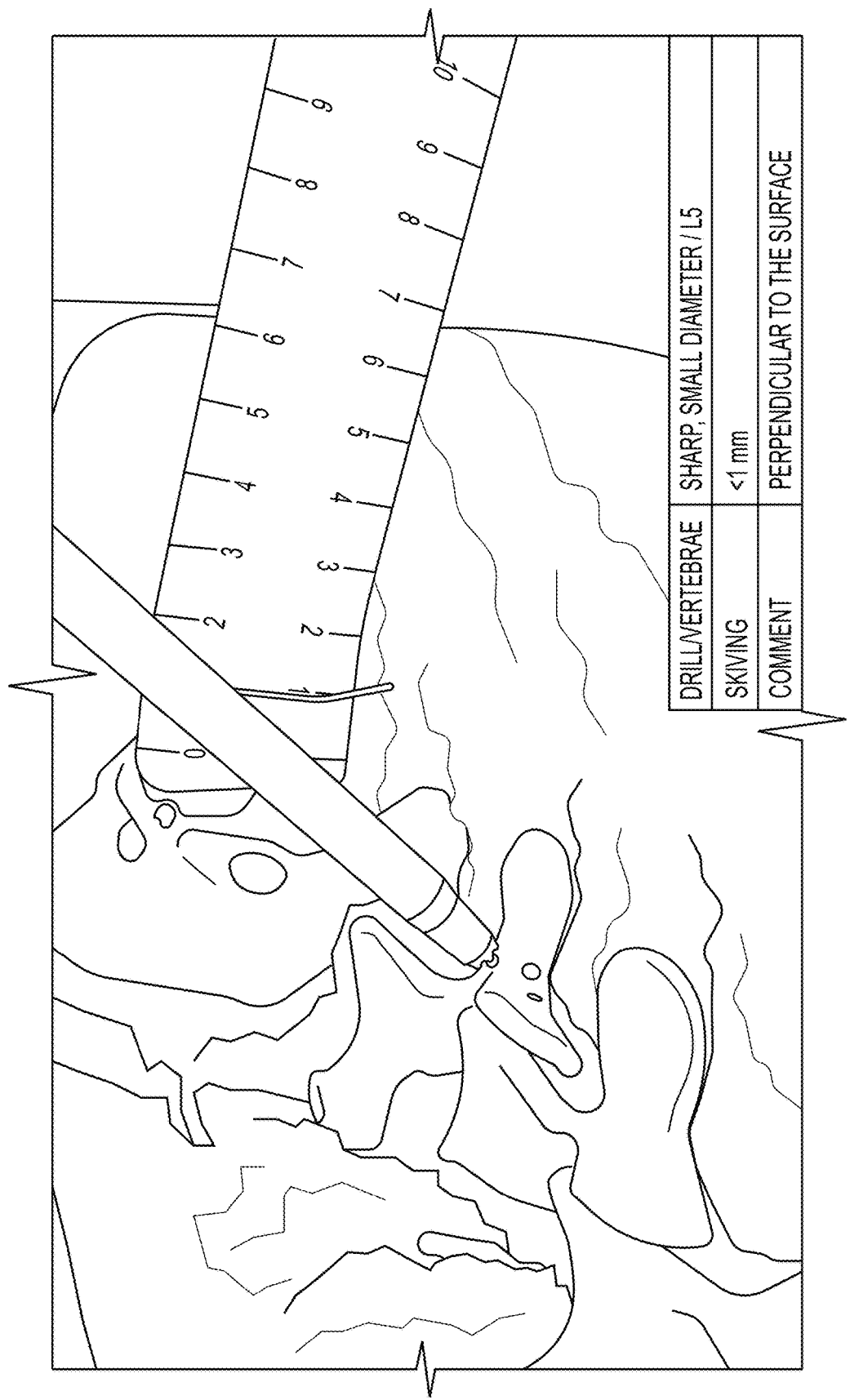
FIG. 10 is a still photographs taken during an experiment performed using the disclosed technology and standard drill bits to measure the amount of skiving experienced with different drill bit designs.
Figure 11:
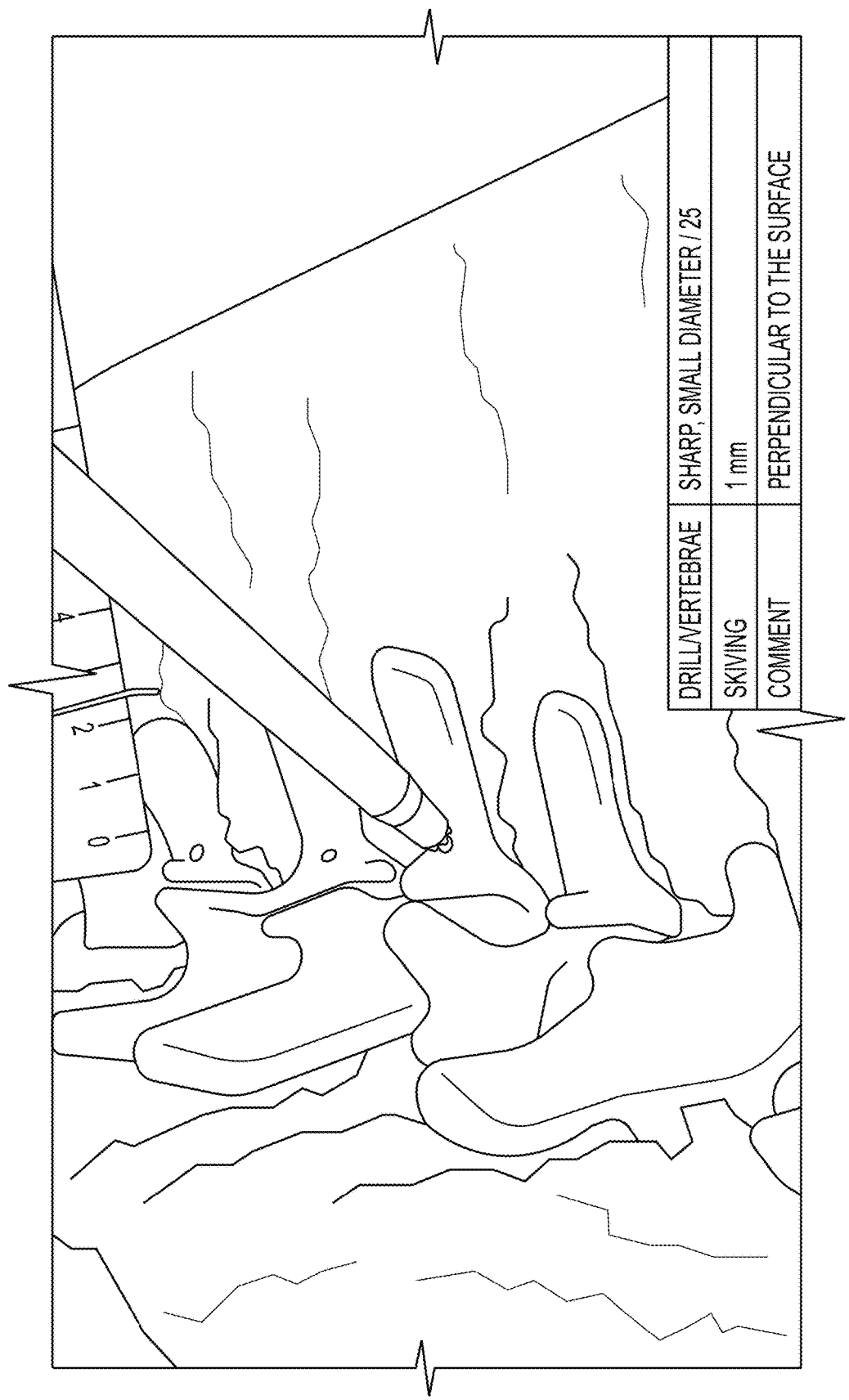
FIG. 11 is a still photographs taken during an experiment performed using the disclosed technology and standard drill bits to measure the amount of skiving experienced with different drill bit designs.
Figure 12:
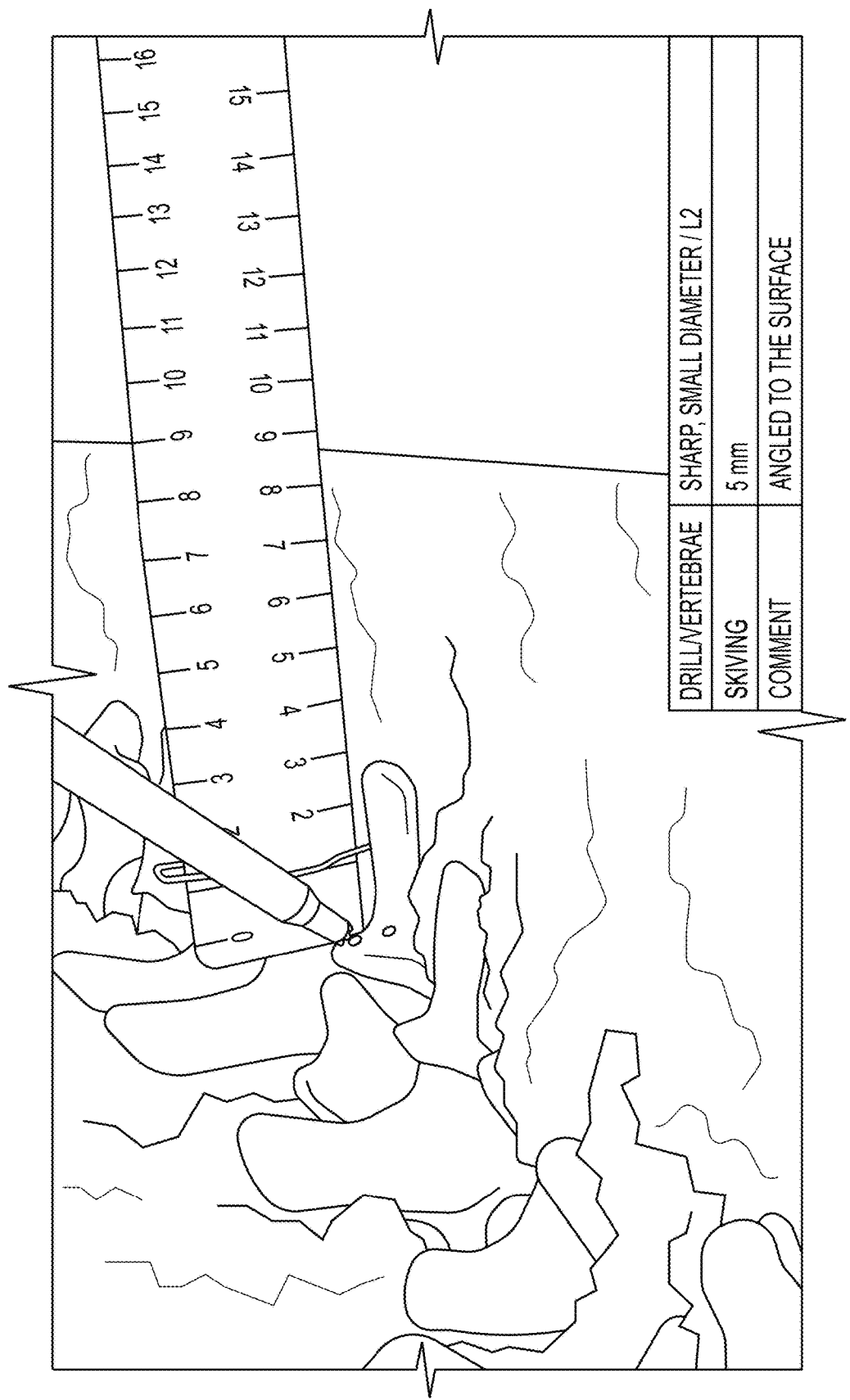
FIG. 12 is a still photographs taken during an experiment performed using the disclosed technology and standard drill bits to measure the amount of skiving experienced with different drill bit designs.
Figure 13:
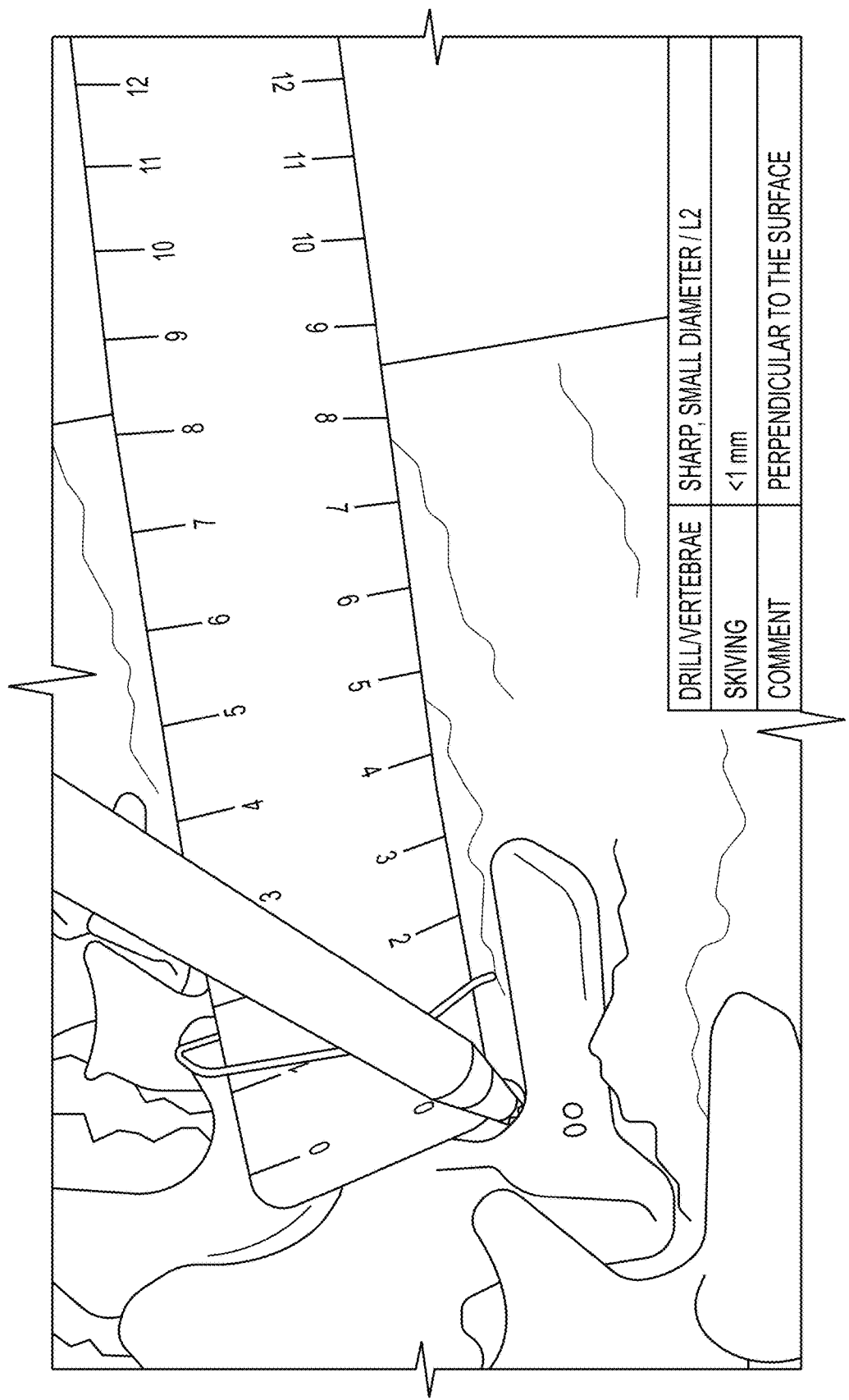
FIG. 13 is a still photographs taken during an experiment performed using the disclosed technology and standard drill bits to measure the amount of skiving experienced with different drill bit designs.
Figure 14:
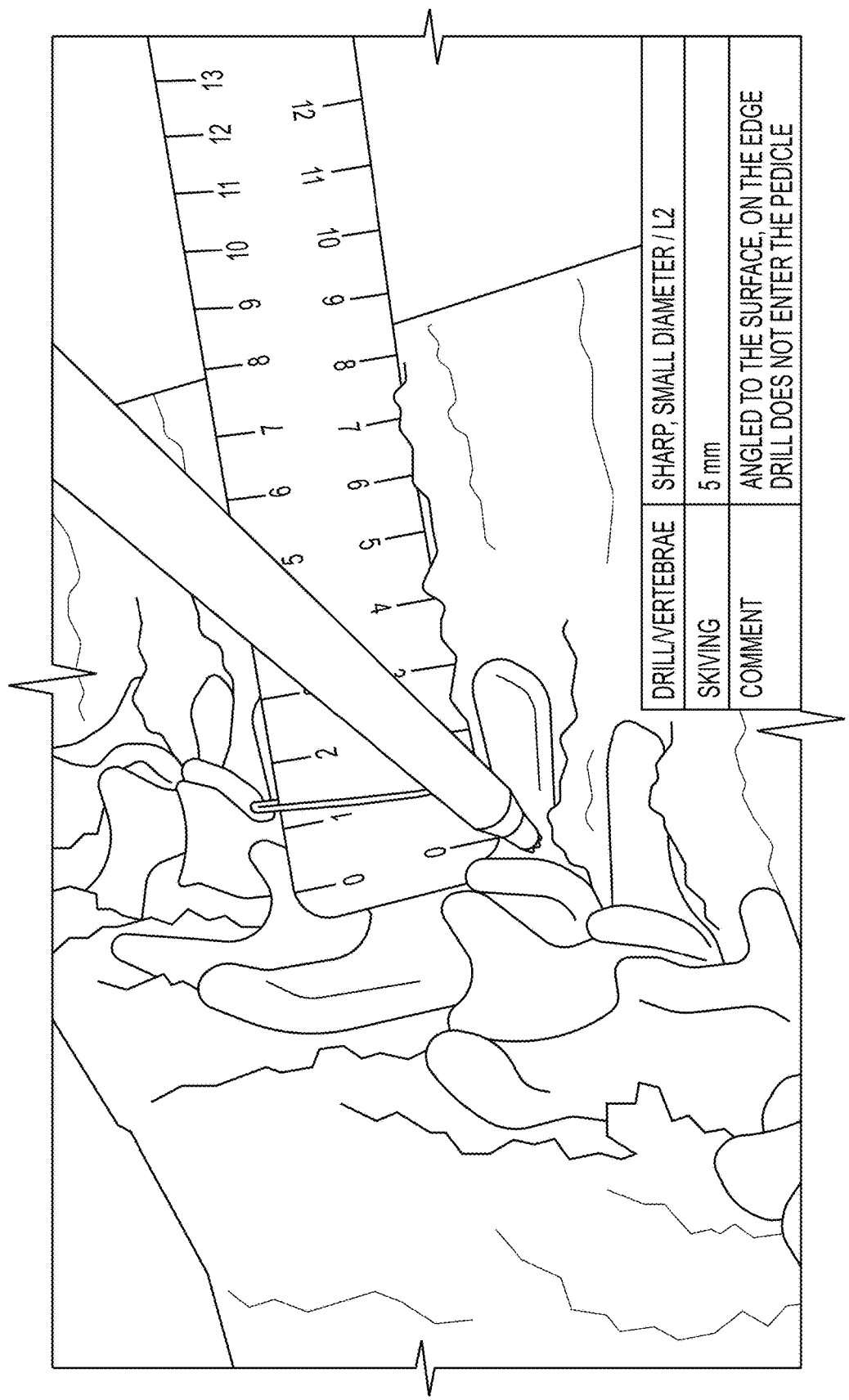
FIG. 14 is a still photographs taken during an experiment performed using the disclosed technology and standard drill bits to measure the amount of skiving experienced with different drill bit designs.
Figure 15:
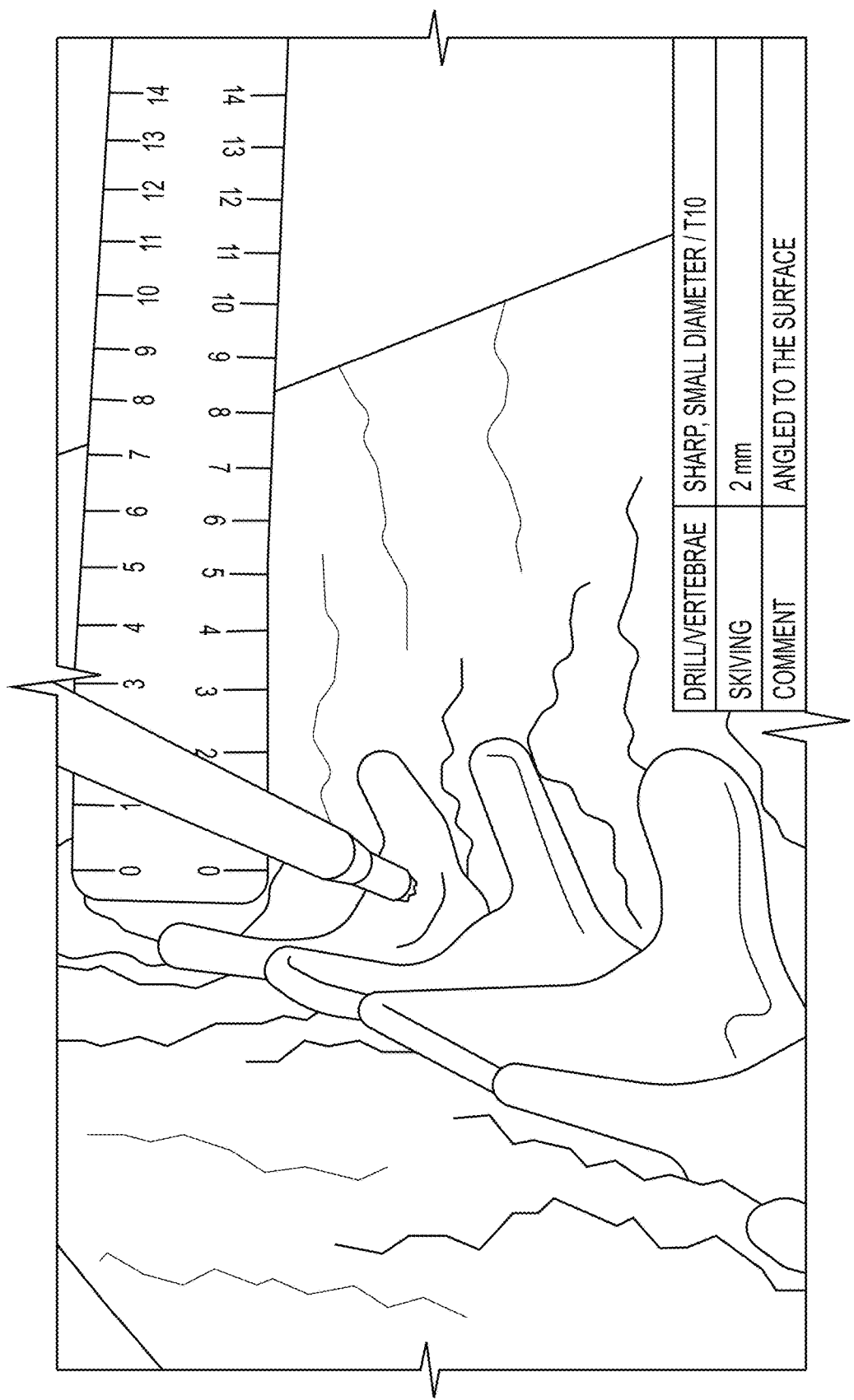
FIG. 15 is a still photographs taken during an experiment performed using the disclosed technology and standard drill bits to measure the amount of skiving experienced with different drill bit designs.
Figure 16:
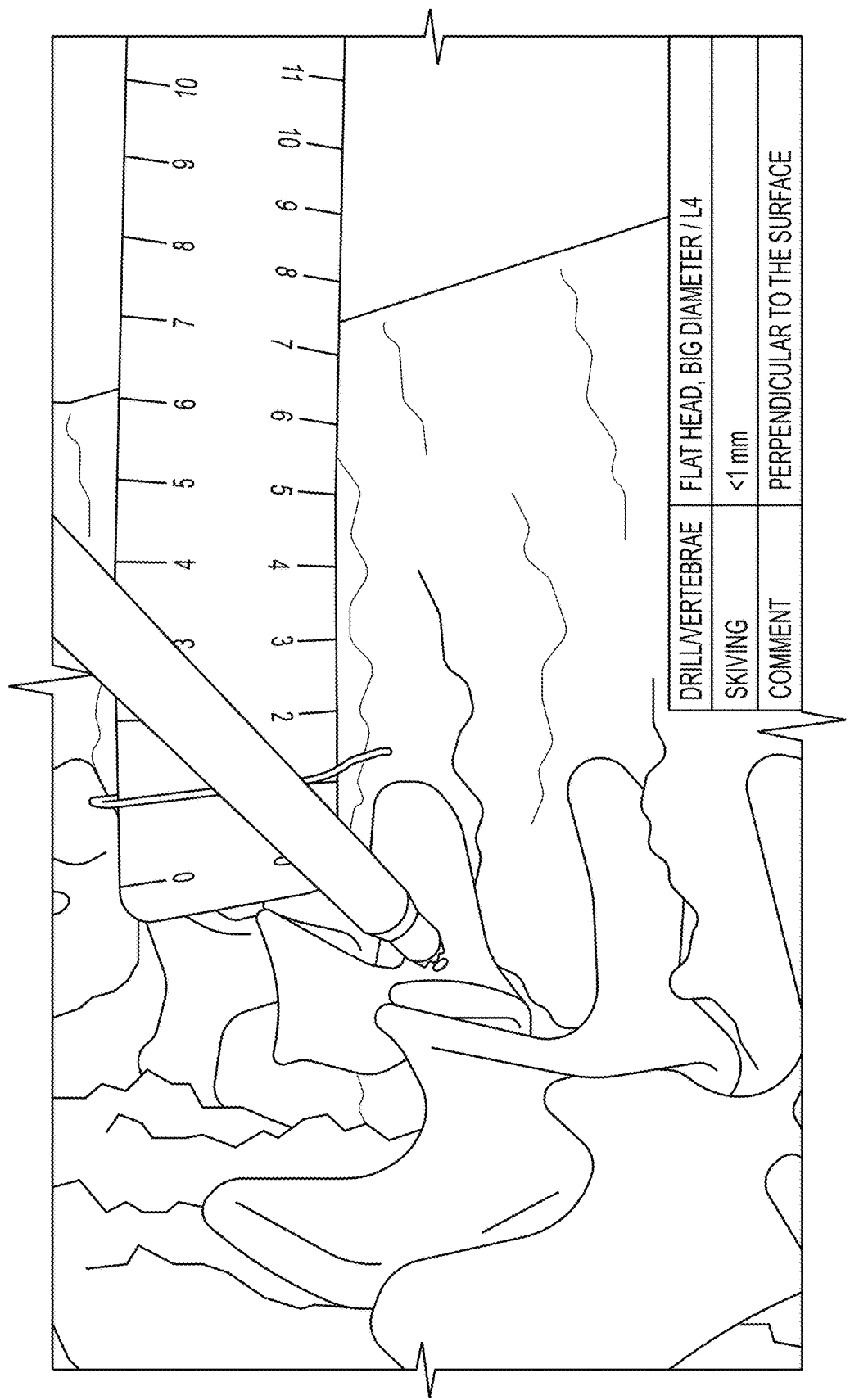
FIG. 16 is a still photographs taken during an experiment performed using the disclosed technology and standard drill bits to measure the amount of skiving.
Figure 17:
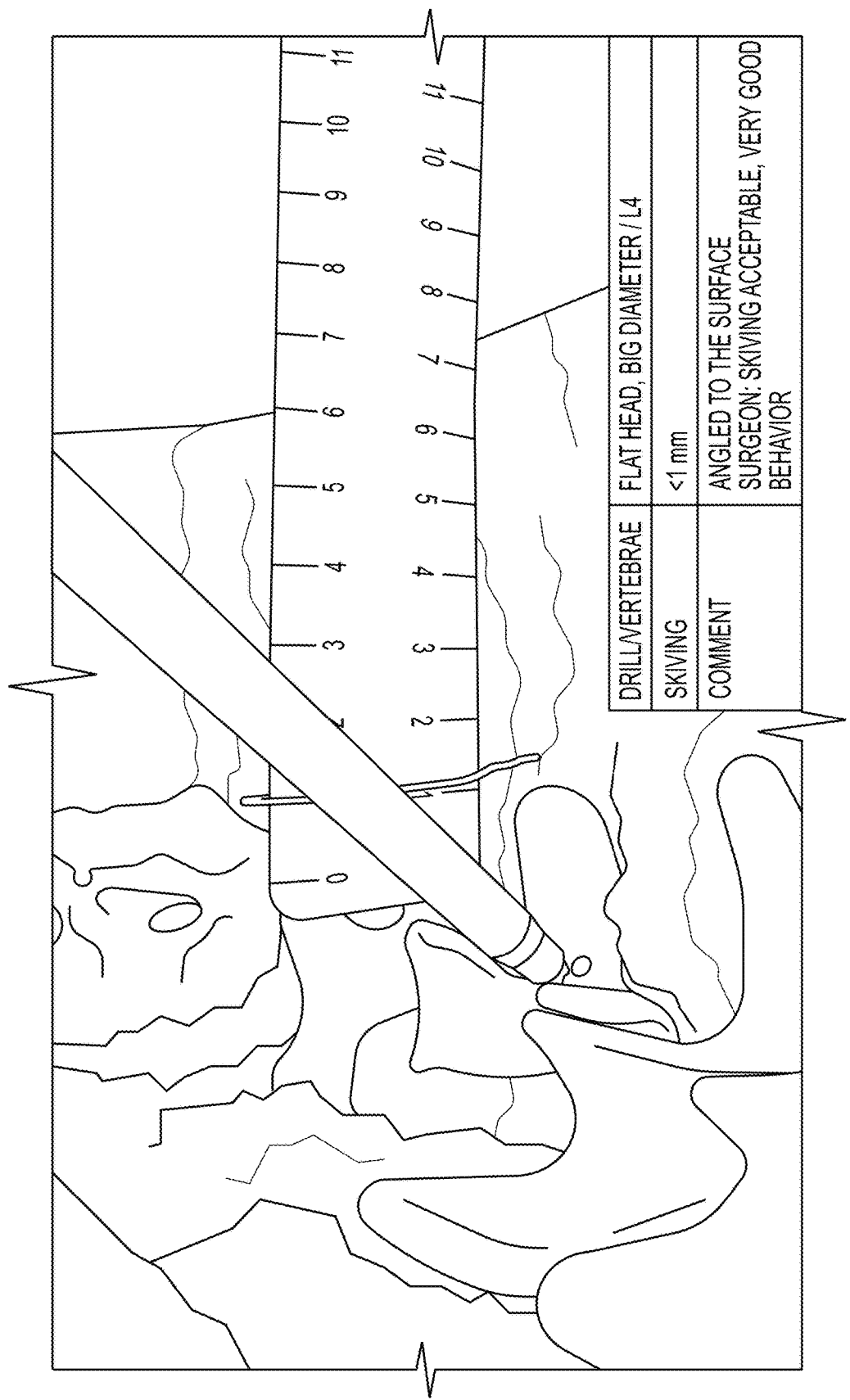
FIG. 17 is a still photographs taken during an experiment performed using the disclosed technology and standard drill bits to measure the amount of skiving experienced with different drill bit designs.
Figure 18:
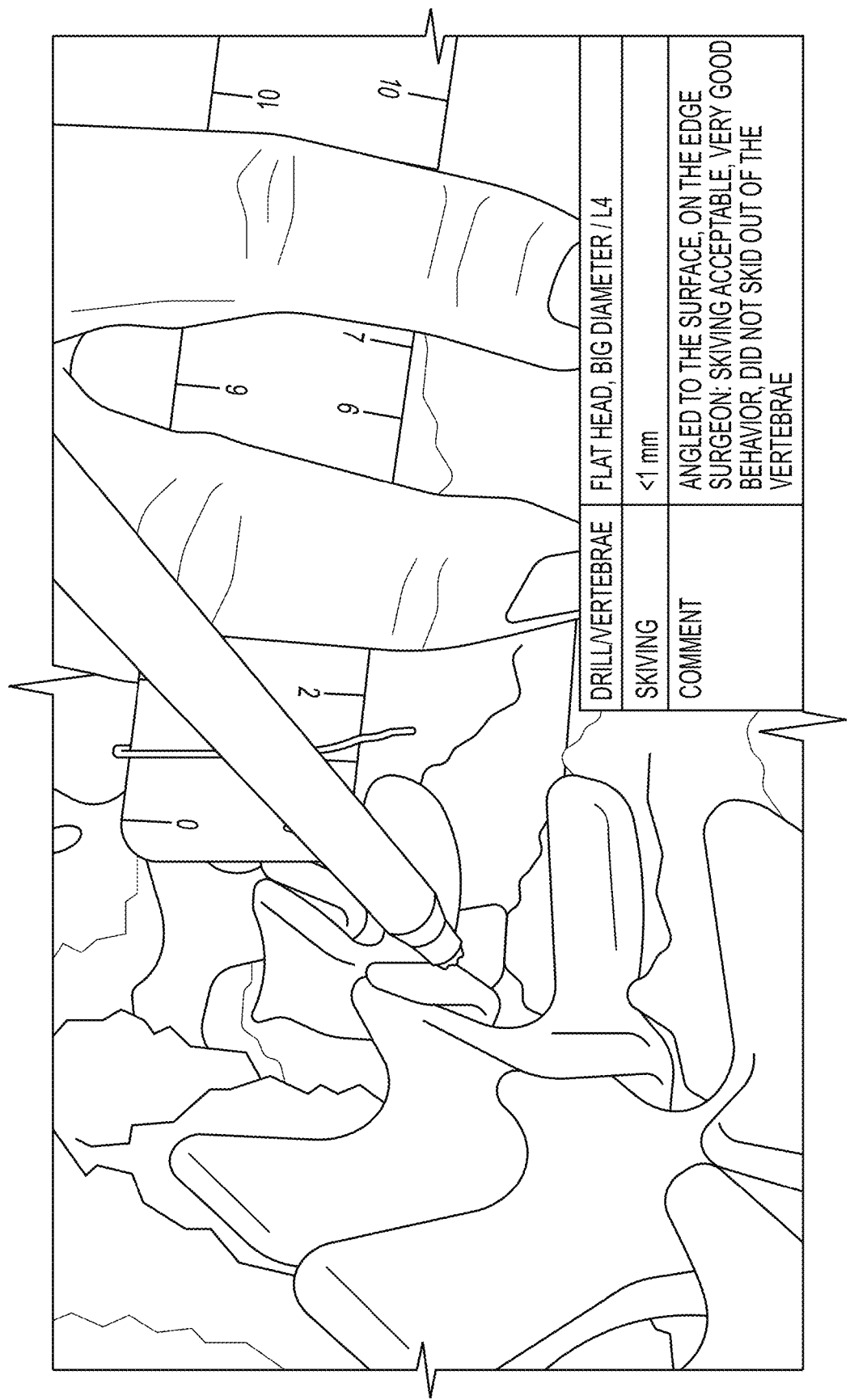
FIG. 18 is a still photographs taken during an experiment performed using the disclosed technology and standard drill bits to measure the amount of skiving experienced with different drill bit designs.
Figure 19:
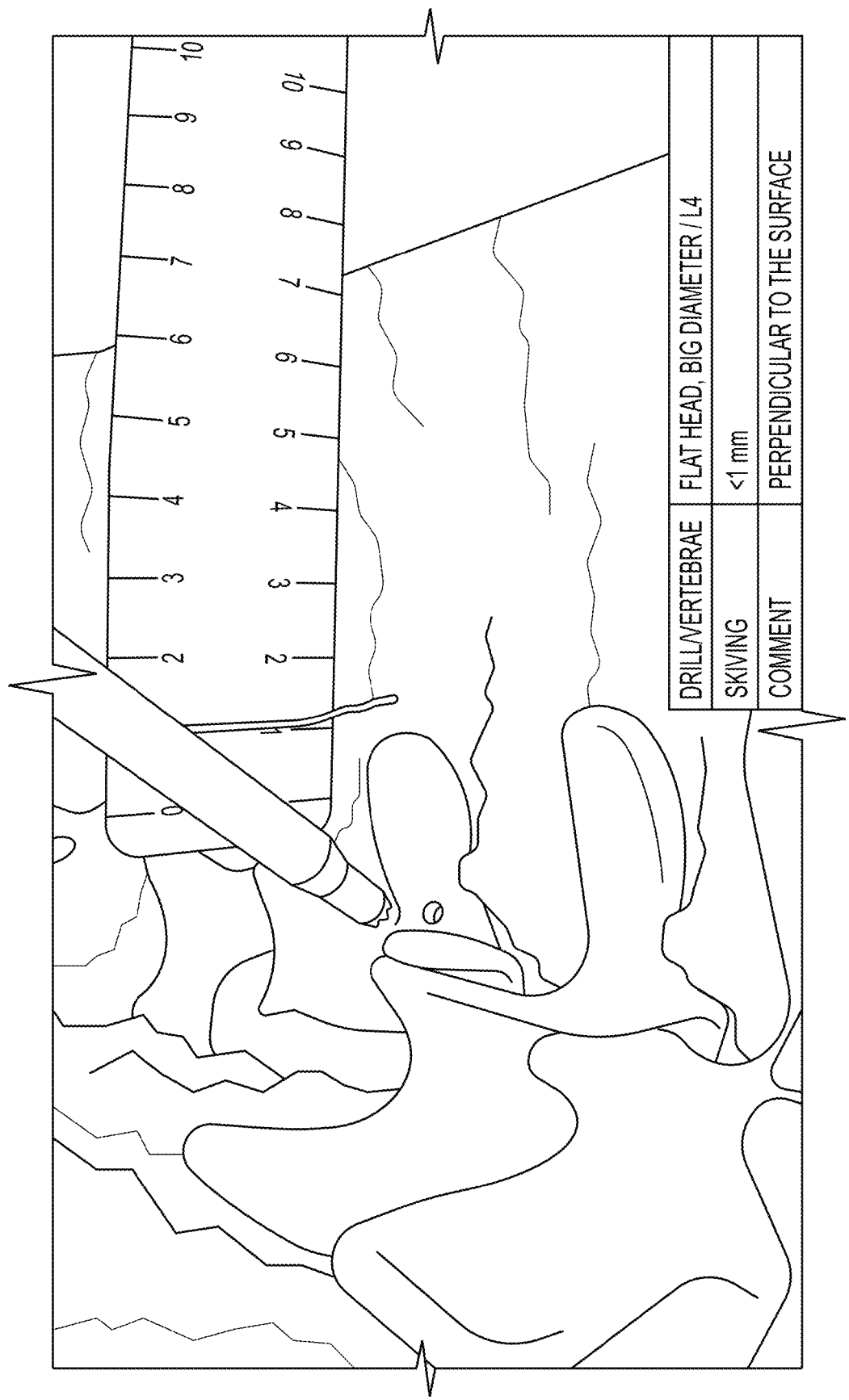
FIG. 19 is a still photographs taken during an experiment performed using the disclosed technology and standard drill bits to measure the amount of skiving experienced with different drill bit designs.
Figure 20:
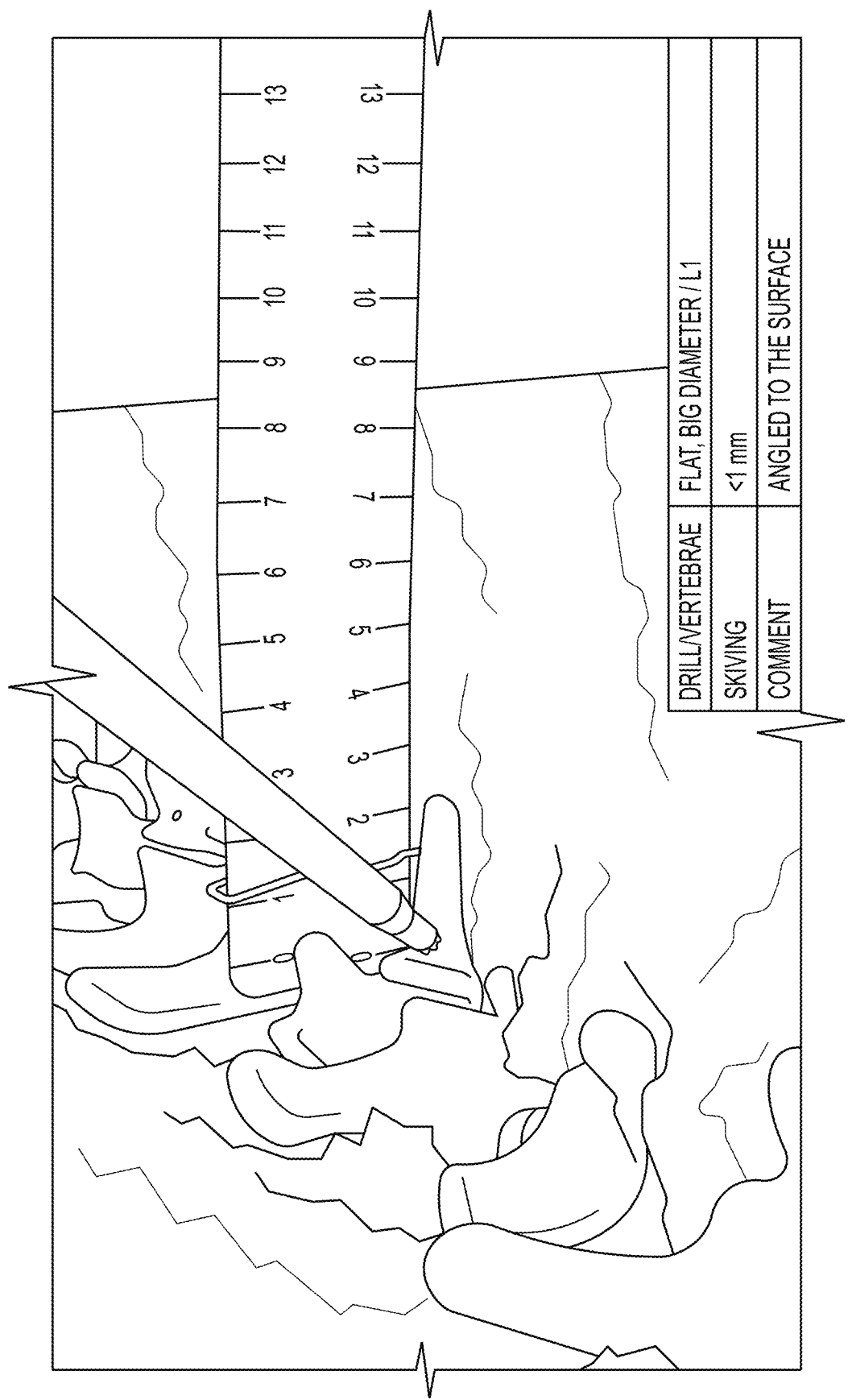
FIG. 20 is a still photographs taken during an experiment performed using the disclosed technology and standard drill bits to measure the amount of skiving experienced with different drill bit designs.
Figure 21:
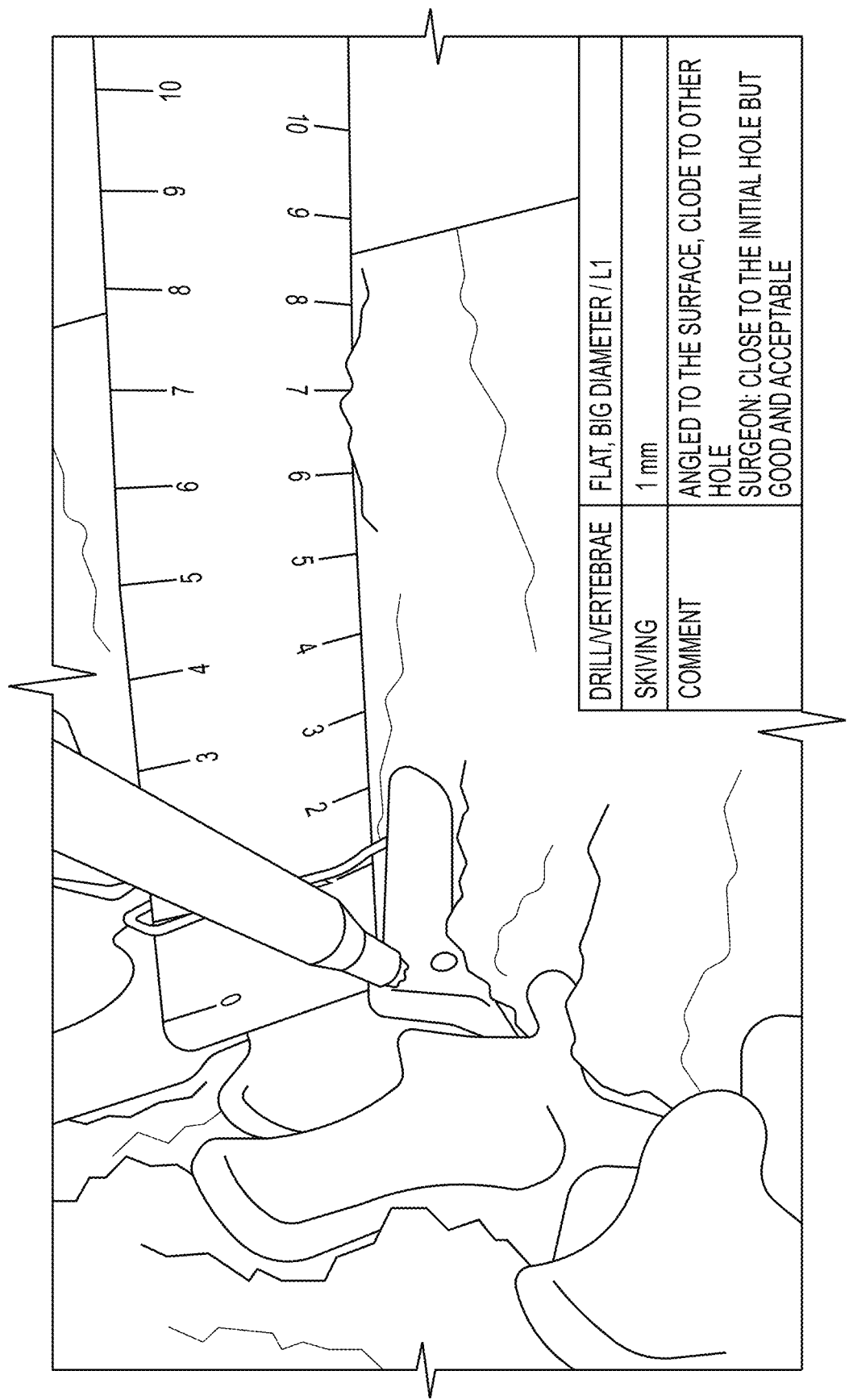
FIG. 21 is a still photographs taken during an experiment performed using the disclosed technology and standard drill bits to measure the amount of skiving experienced with different drill bit designs.
Figure 22:
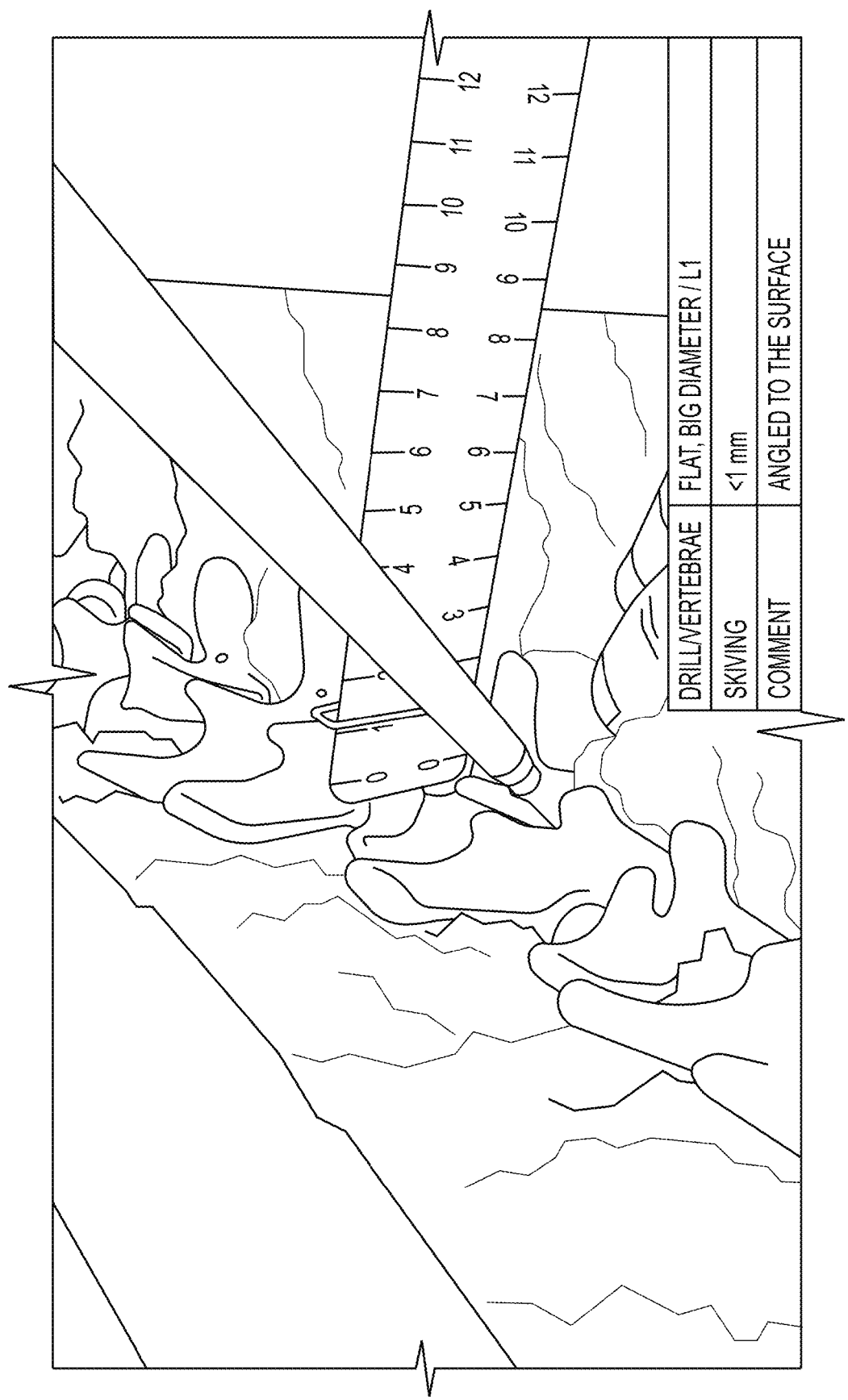
FIG. 22 is a still photographs taken during an experiment performed using the disclosed technology and standard drill bits to measure the amount of skiving experienced with different drill bit designs.
Figure 23:
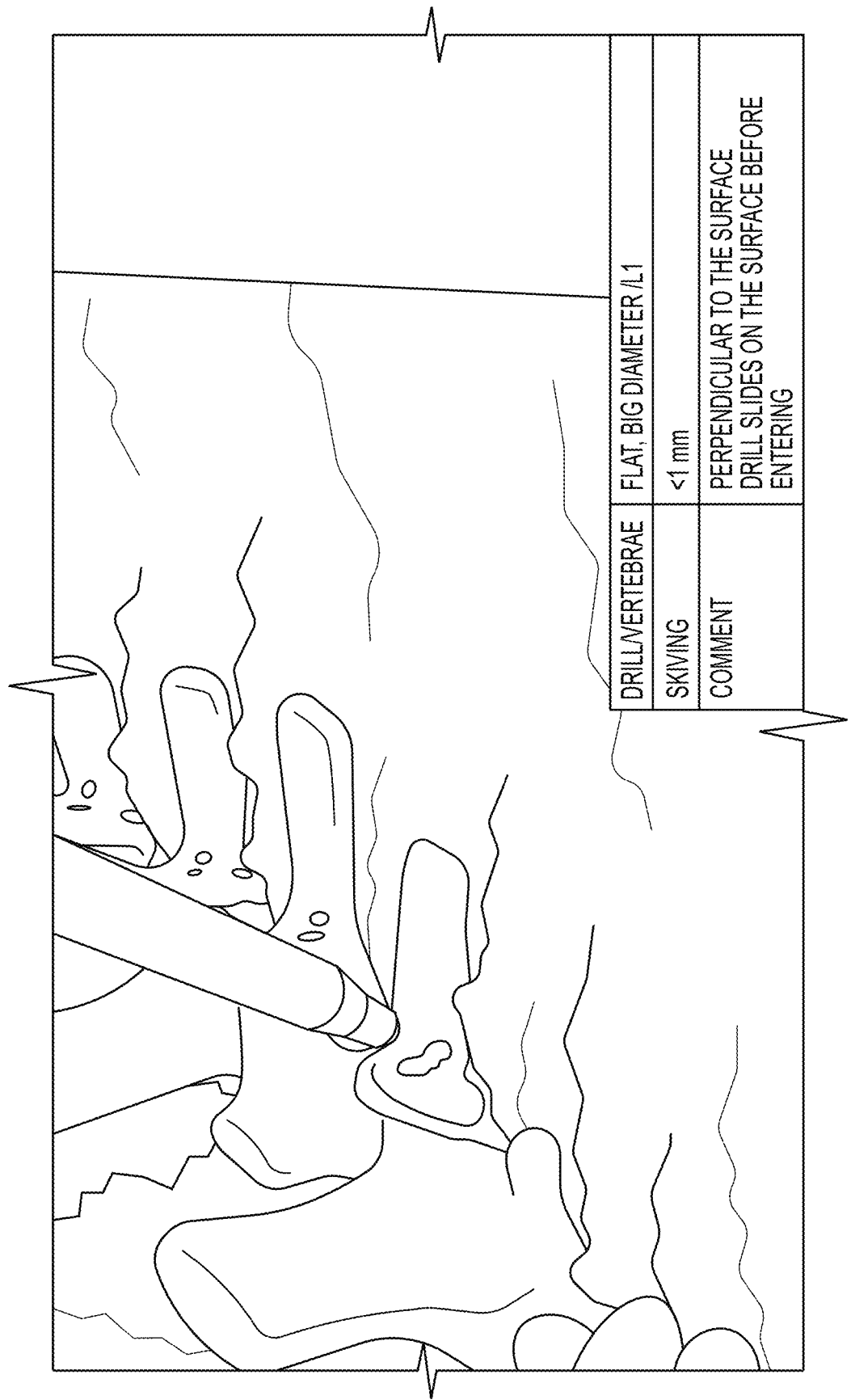
FIG. 23 is a still photographs taken during an experiment performed using the disclosed technology and standard drill bits to measure the amount of skiving experienced with different drill bit designs.
Figure 24:
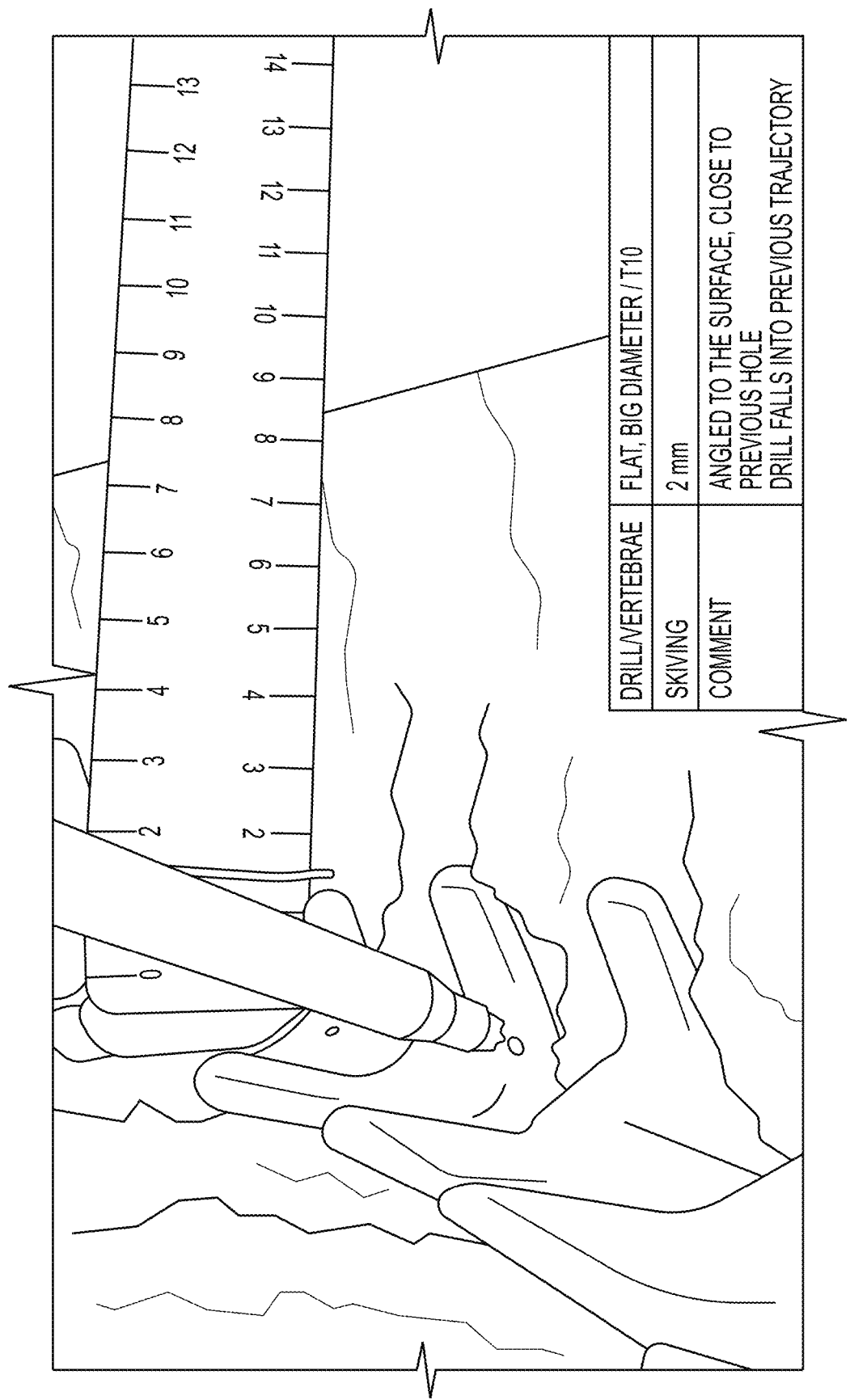
FIG. 24 is a still photographs taken during an experiment performed using the disclosed technology and standard drill bits to measure the amount of skiving experienced with different drill bit designs.
Figure 25:
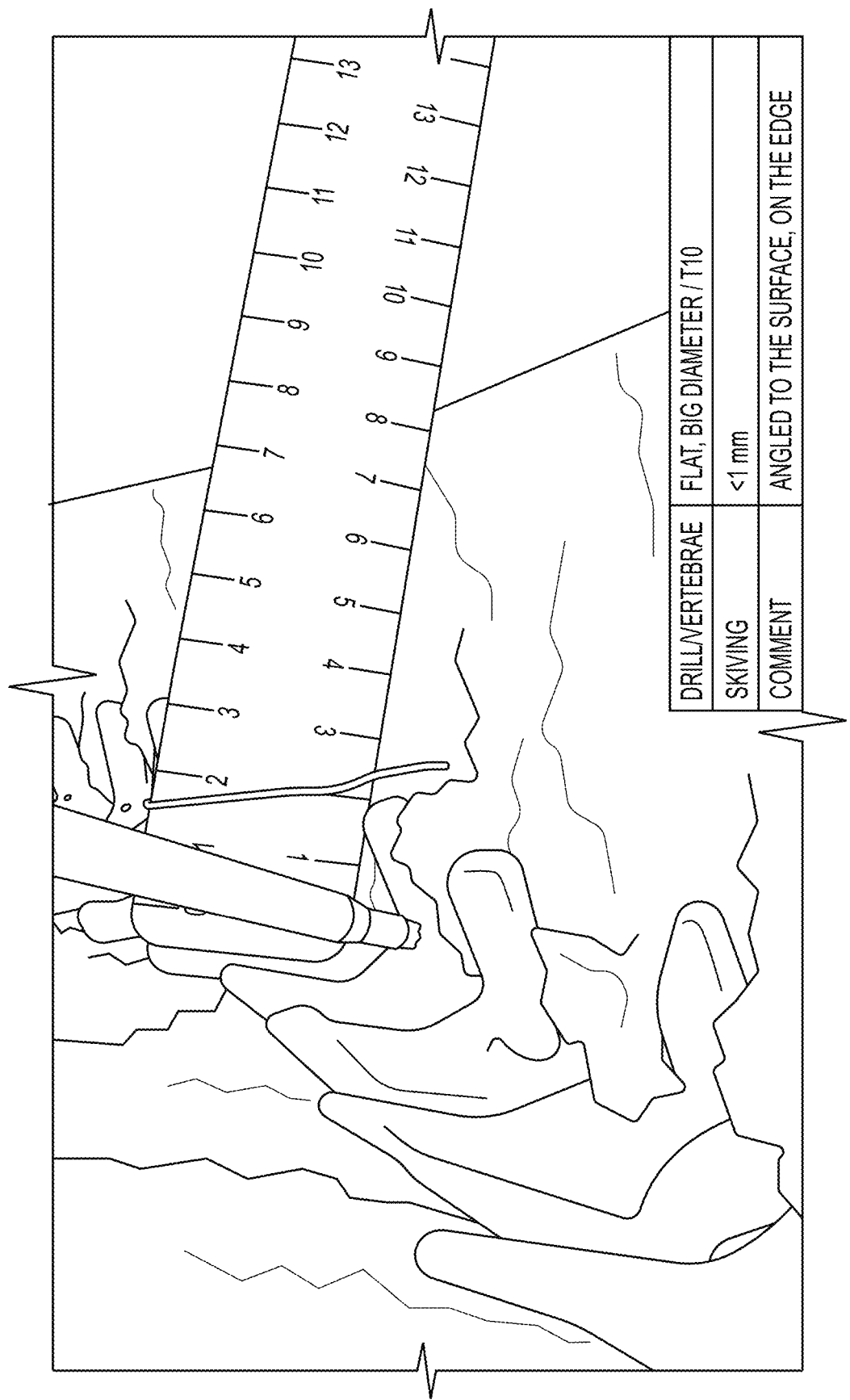
FIG. 25 is a still photographs taken during an experiment performed using the disclosed technology and standard drill bits to measure the amount of skiving experienced with different drill bit designs.
Figure 26:
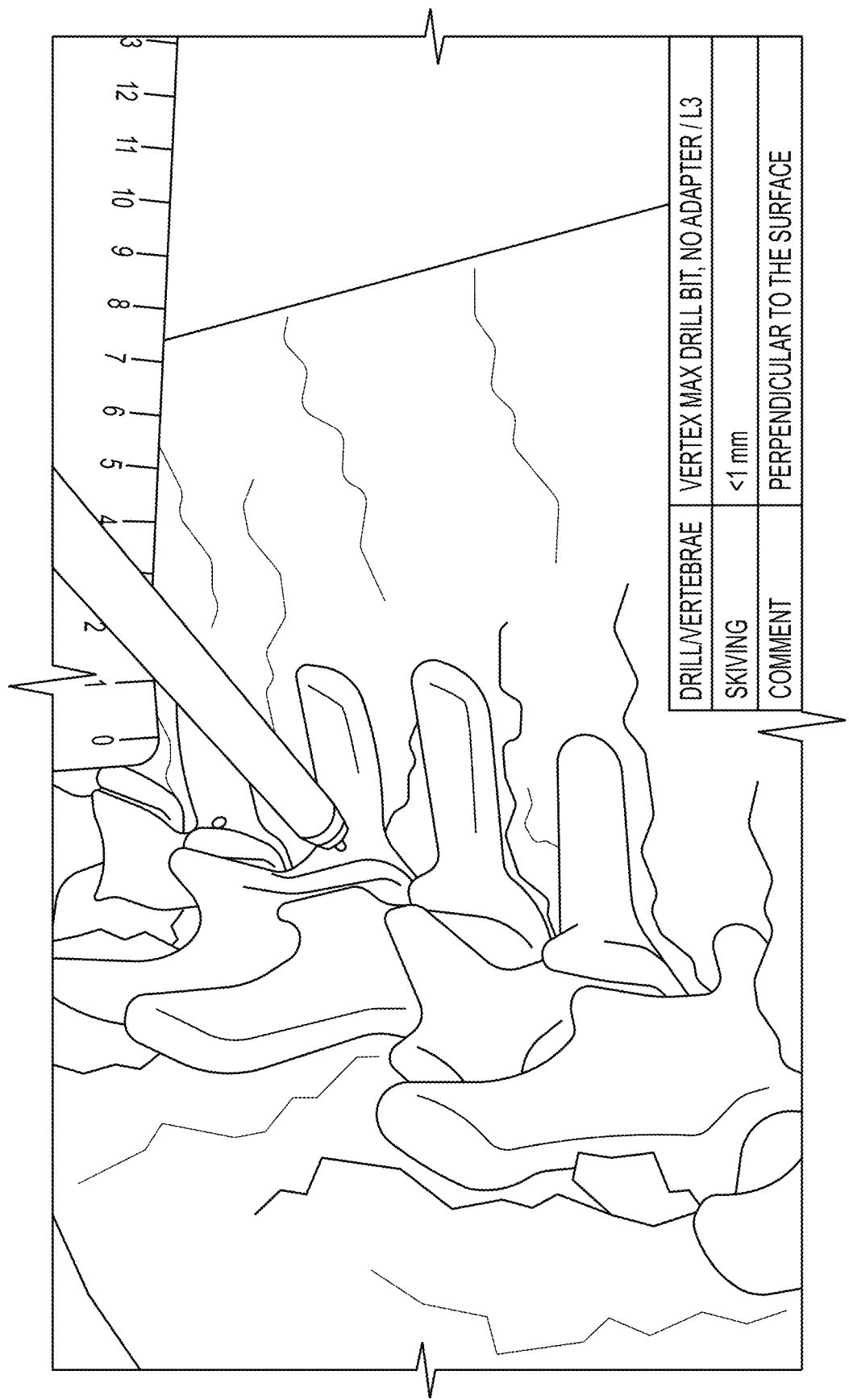
FIG. 26 is a still photographs taken during an experiment performed using the disclosed technology and standard drill bits to measure the amount of skiving experienced with different drill bit designs.
Figure 27:
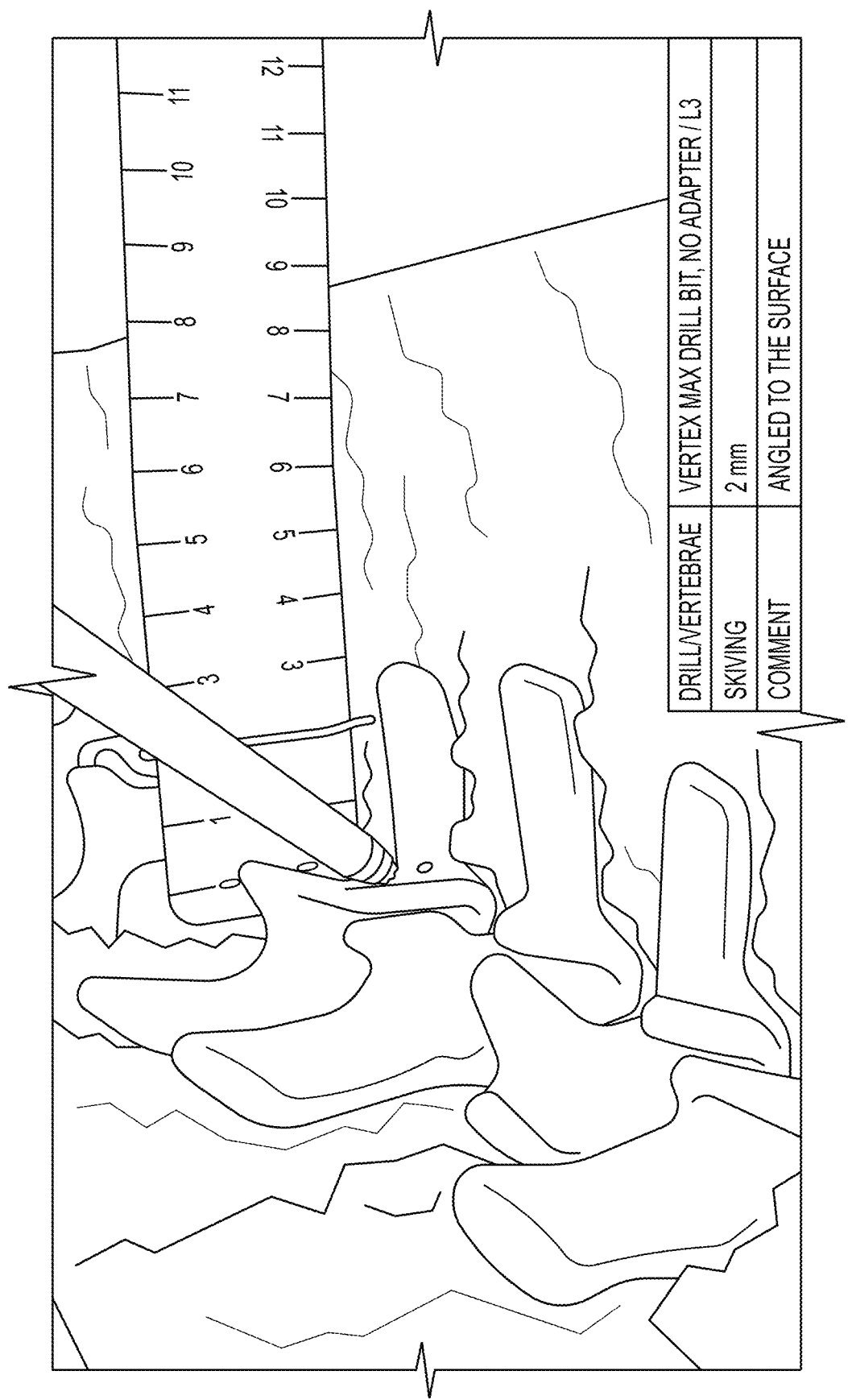
FIG. 27 is a still photographs taken during an experiment performed using the disclosed technology and standard drill bits to measure the amount of skiving experienced with different drill bit designs.
Figure 28:
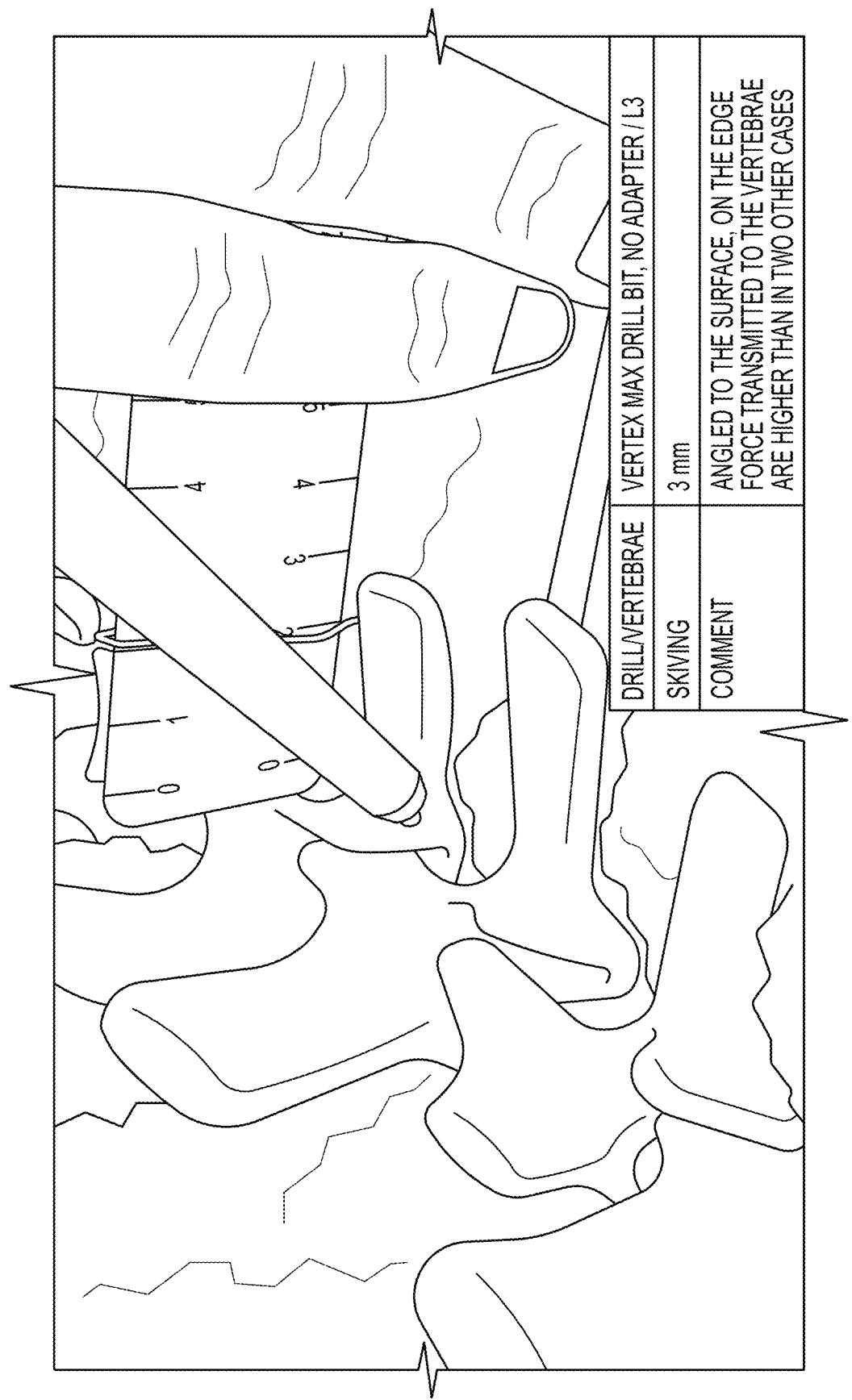
FIG. 28 is a still photographs taken during an experiment performed using the disclosed technology and standard drill bits to measure the amount of skiving experienced with different drill bit designs.
Figure 29:
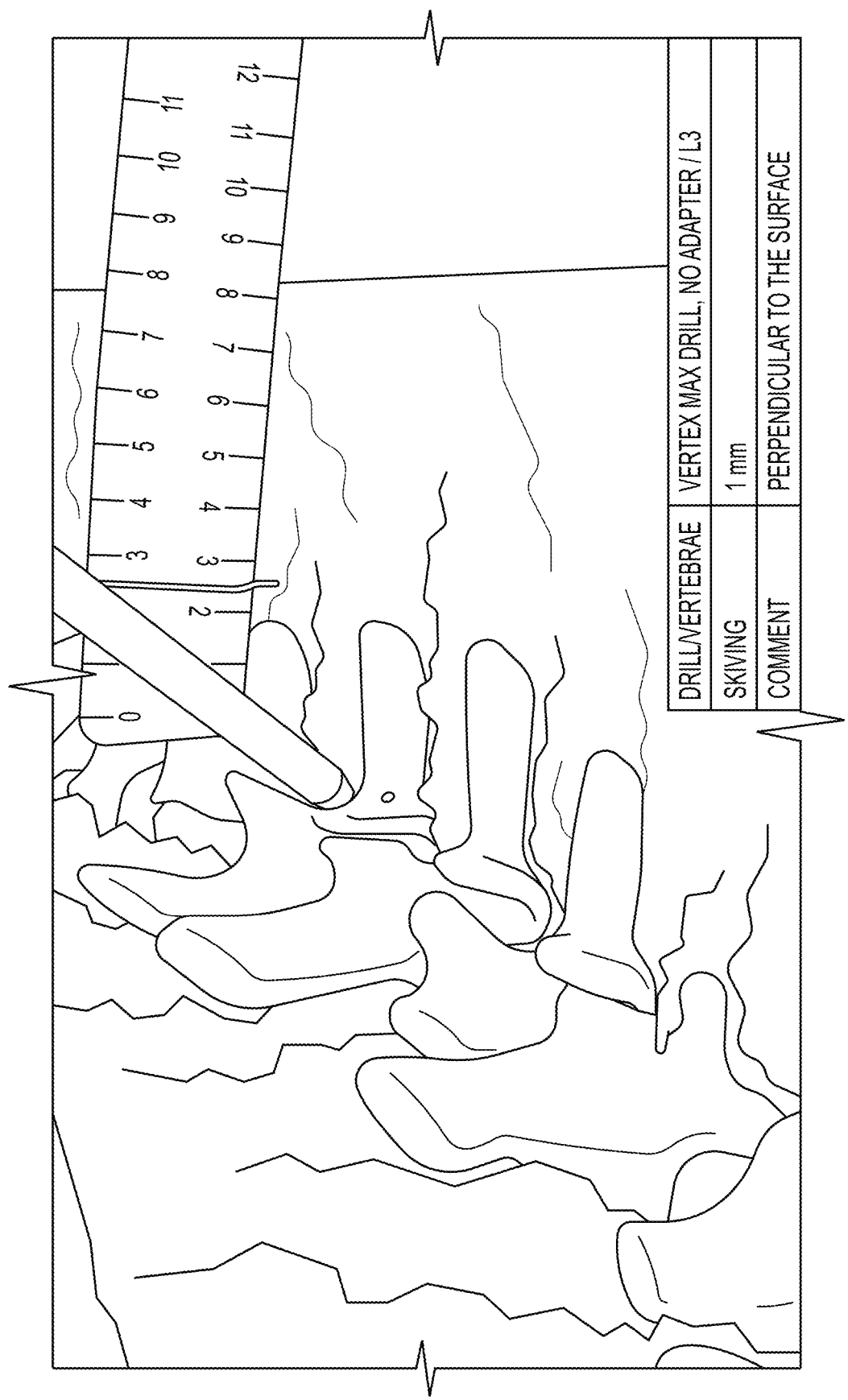
FIG. 29 is a still photographs taken during an experiment performed using the disclosed technology and standard drill bits to measure the amount of skiving experienced with different drill bit designs.
Figure 30:
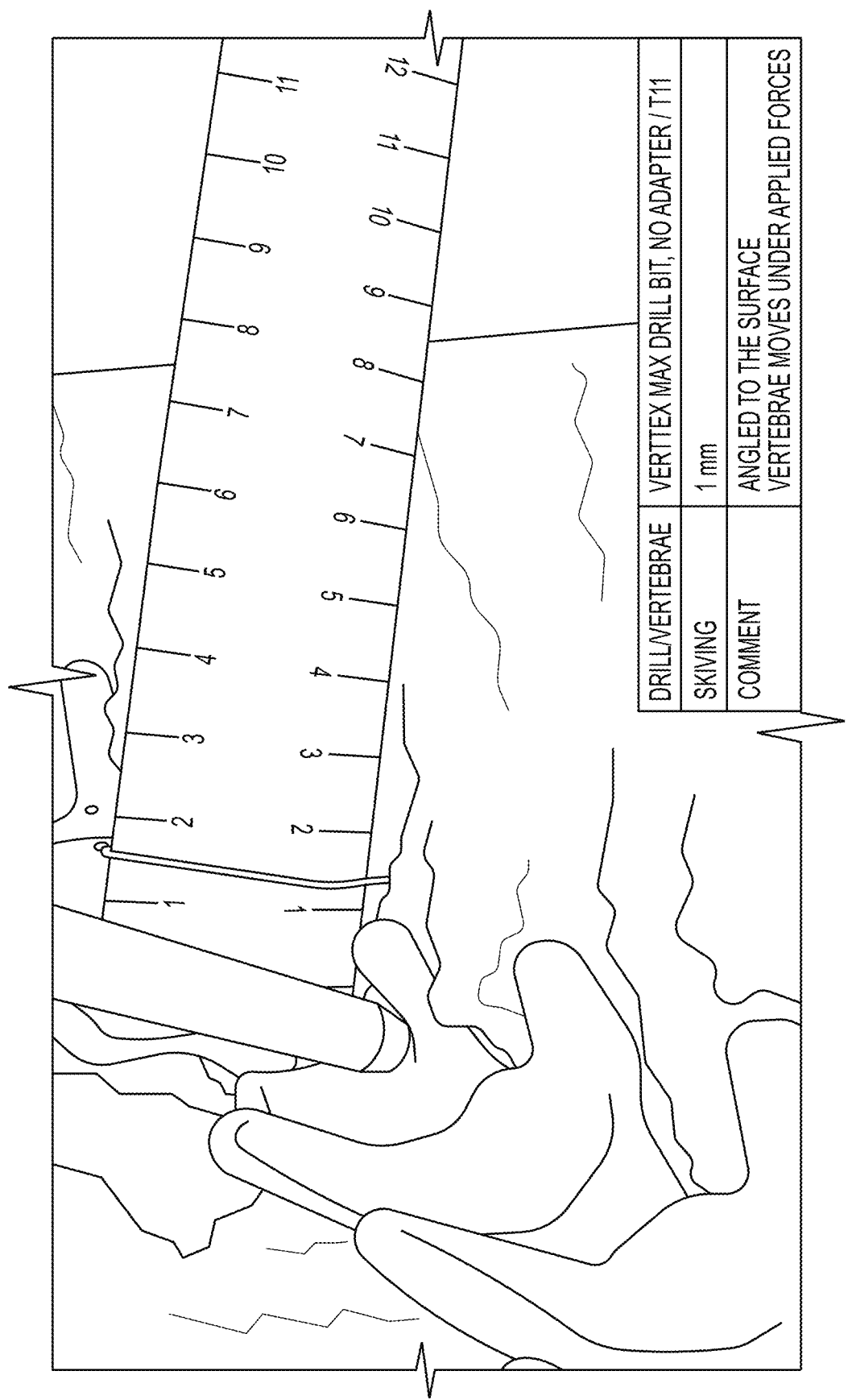
FIG. 30 is a still photographs taken during an experiment performed using the disclosed technology and standard drill bits to measure the amount of skiving experienced with different drill bit designs.

FIG. 5 is a photograph of different types of drill bits tested during this experiment. An anti-skid drill-bit in accordance with the disclosed technology is shown as drill bit 502. It comprises a body similar to a standard drill bit and a flat end (rather than a pointy end) in accordance with an embodiment of the invention. Drill bit 504 (e.g., Drill Bit for Universal Drill Bit Guide by Medtronic of Minneapolis, MN) and drill bit 506 (e.g., Vertex® Max Drill Bit by Medtronic of Minneapolis, MN) are commercially available drill bits.

FIGS. 6 through 30 show images from a series of drilling movies captured during the experiment. Recording was done using a high-frequency camera (128 fps) for greater precision. The visible ruler in the background allowed for estimating displacements of various elements. All drilling was done by the surgeon. Trajectories were planned in the way that emphasizes possible skiving situations while being clinically relevant. Such situations are: angles surface (i.e. not perpendicular to the drill bit axis), on the bone edge, close to other existing hole.

FIGS. 6 through 15 are images captured during experiments conducted with drill bit 504. Experiments with drill bit 504 (a standard drill bit represented by a small diameter, sharp drill bit) illustrated no skiving if drill bit is perpendicular to the drilled surface. However, there was significant skiving (+5 mm) on angled surfaces which can lead to imprecise drilled holes and extra-pedicular holes (i.e., holes outside pedicle either medial (spinal canal, can lead to paralysis) or lateral (vascular system, can lead to death)).

FIGS. 16 through 25 are images captured during experiments conducted with drill bit 502 (flat head, big diameter) which was constructed in accordance with an embodiment of this invention. Experiments with anti-skiving drill bit 502 illustrated acceptable skiving (=1 mm) in drilling to all surfaces (perpendicular and angled). Experiments showed that the anti-skive drill bit 502 can drill in proximity of previous holes without falling into them and the bit 502 can jitter on the flat surface before penetrating into bone (i.e., ski before penetrating into bone). With optimized drill bit shape (e.g., the drill bit shown in FIG. 32A or FIG. 32B), the performance of this function shall improve.

FIGS. 26 through 30 are images captured during experiments conducted with drill bit 506 (represented by Vertex Max drill bit in the experiment). Experiments found that drill bit 506 skived less than the standard drill bit 504, but more than the anti-skiving drill bit 502. Additionally, the drill bit 506 transmitted higher forces to the vertebrae. Thus, as shown in the experiments, the disclosed technology provides drill bits that reduce or eliminate unwanted skiving less than conventional drill bits.

Figure 31:
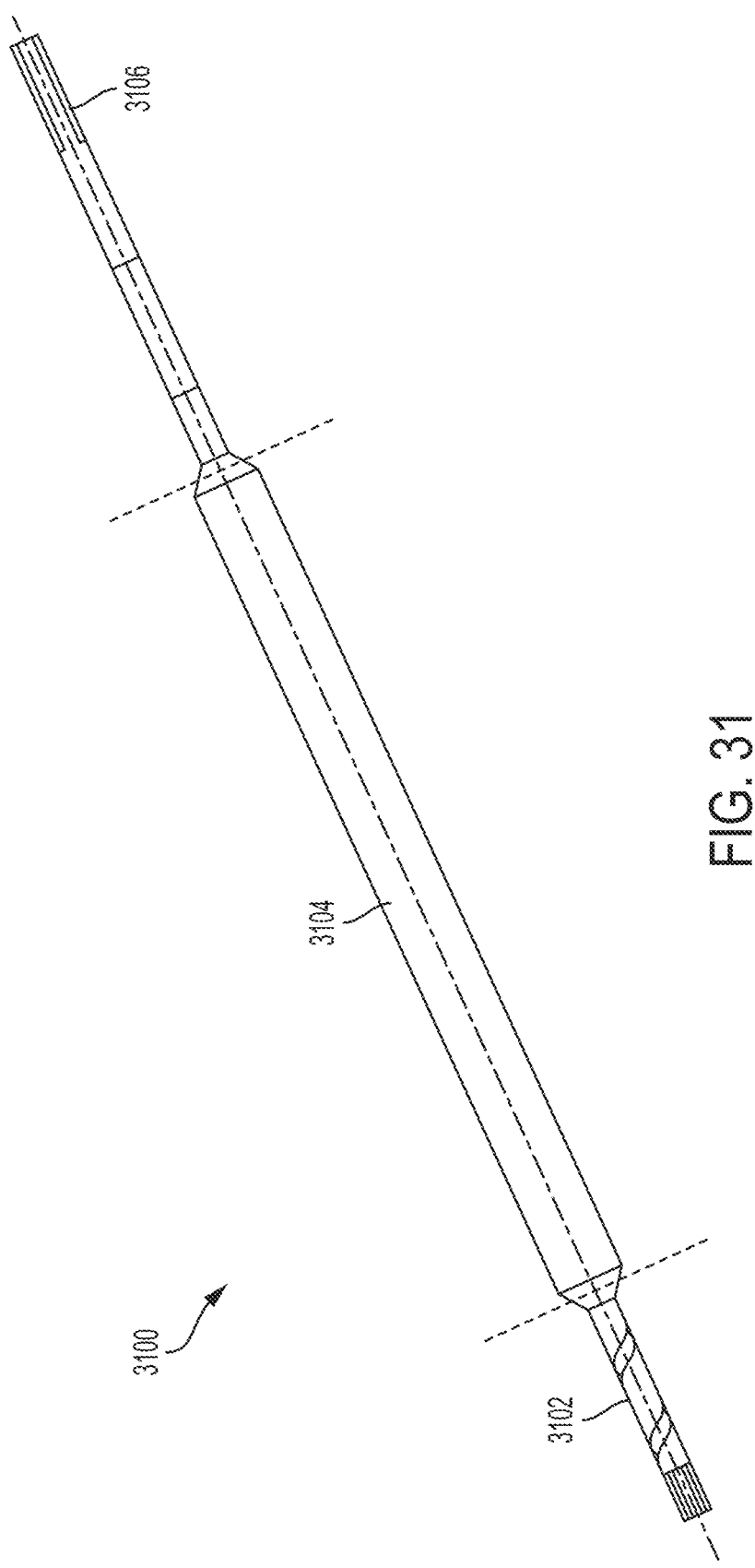
FIG. 31 illustrates an anti-skive drill bit in accordance with embodiments of the disclosed technology.

FIGS. 31 through 35 illustrate anti-skive drill bits in accordance with embodiments of the disclosed technology. In certain embodiments, as illustrated in FIG. 31, a drill bit 3100 in accordance with an embodiment of the disclosed technology includes a drilling part 3102 for creating a hole and evacuate material as the hole is created, a guiding part 3104 that interacts with a guide (e.g., held by a robot), and an attachment part 3106 (e.g., a shank) that can be inserted into and/or securely held by a drill. As discussed above, the drill bit 3100 has a milling head 3108.

Figure 32A:
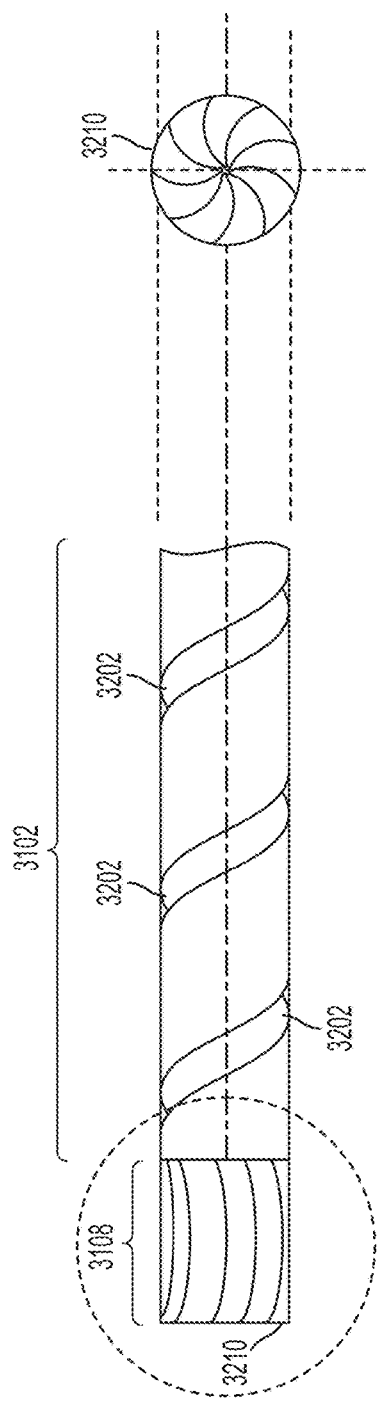
FIG. 32A and FIG. 32B illustrate anti-skive drill bits in accordance with embodiments of the disclosed technology.
Figure 32B:
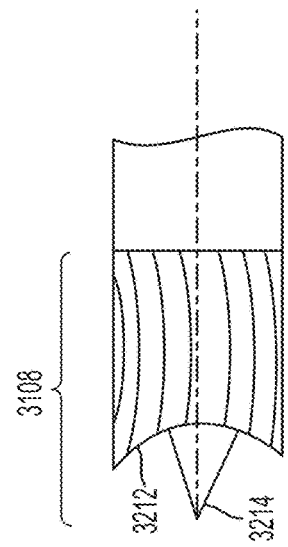

In certain embodiments, as shown in FIGS. 32A and 32B, the drilling part 3102 has flutes 3202 along the side of the body. These flutes 3202 evacuate material as a hole is drilled. The front face 3210 may be flat and/or have front-cutting surfaces 3210. Additionally, a portion of the body 3108 between the front face and the flutes can have side-cutting surfaces (e.g., milling faces). An alternative front face device includes a concave shape 3212 with a spike 3214 to better guide on flat faces of bone. The spike 3214, in this embodiment, is centered on the front face.

Figure 33A:
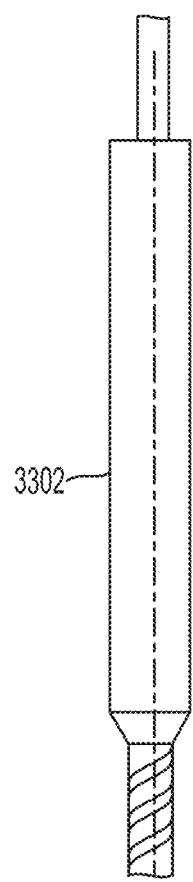
FIG. 33A and FIG. 33B illustrate anti-skive drill bits in accordance with embodiments of the disclosed technology.
Figure 33B:
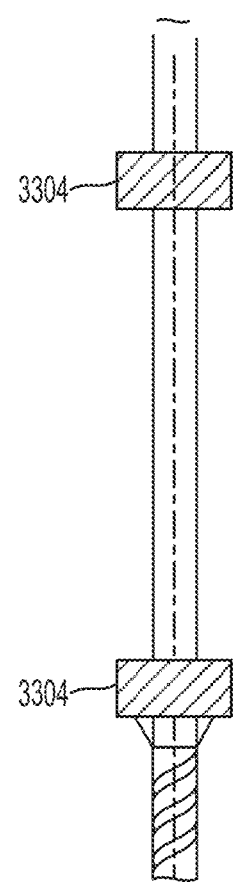

In certain embodiments, as shown in FIGS. 33A and 33B, the drill bit includes a guiding part 3104 that interacts with a guide (e.g., held by a robot). The guiding part 3104 is sized to fit into a guide without an adapter. The guiding part 3104 may consisting of a single cylindrical body 3302 as shown in FIG. 33A along the length of the drill bit that has a diameter to fit into a guide. In an alternative embodiment, the guiding part includes two cylindrical parts 3304 as shown in FIG. 33B, each with a diameter to fit into a guide. The two guiding parts are separated by a portion of the drill bit body extending therebetween with a smaller diameter than the guiding parts.

Figure 34:
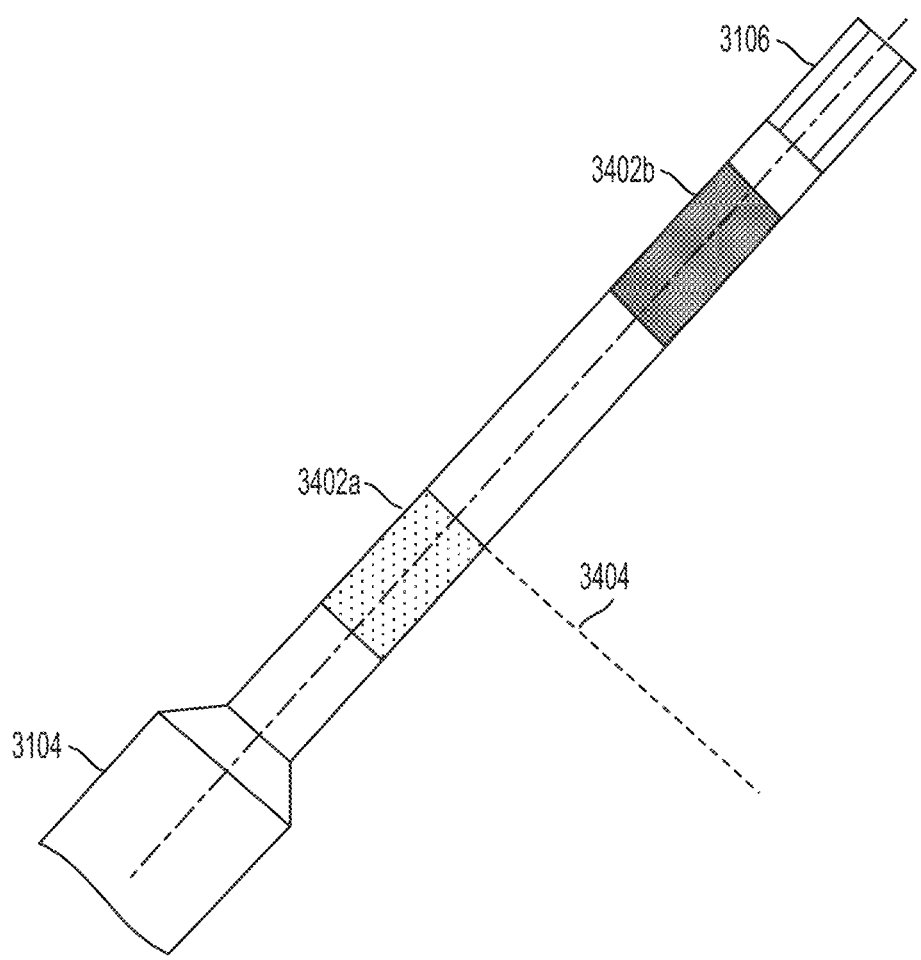
FIG. 34 illustrates an anti-skive drill bit in accordance with embodiments of the disclosed technology.

In certain embodiments, as shown in FIG. 34, between the drill attachment part 3106 of the drill bit and the guide part 3104 of the drill bit, the body of the drill bit has markings 3402a-b to assist a user in preparing holes in a bone. The markings 3402a-b can be notches, colorings, bands, or other indicators. The marking 3402a indicates when to start drill rotation (e.g., before contact with bone). An additional marking 3402b indicates when to stop drill rotation and/or stop depth penetration in the bone. The top side of the marking 3402a can indicate when the drill bit will begin exiting the guide. In certain embodiments, depth control can include a separate depth controller 3506 that attaches to the drill bit 3502 as shown in FIG. 35. The depth controller 3506 can sit on one or more notches 3508 on the drill bit 3502 and be tightened to control the depth the drill bit 3502 will extend beyond a drill bit guide, thereby controlling the depth of penetration in the patient.

Figure 36:
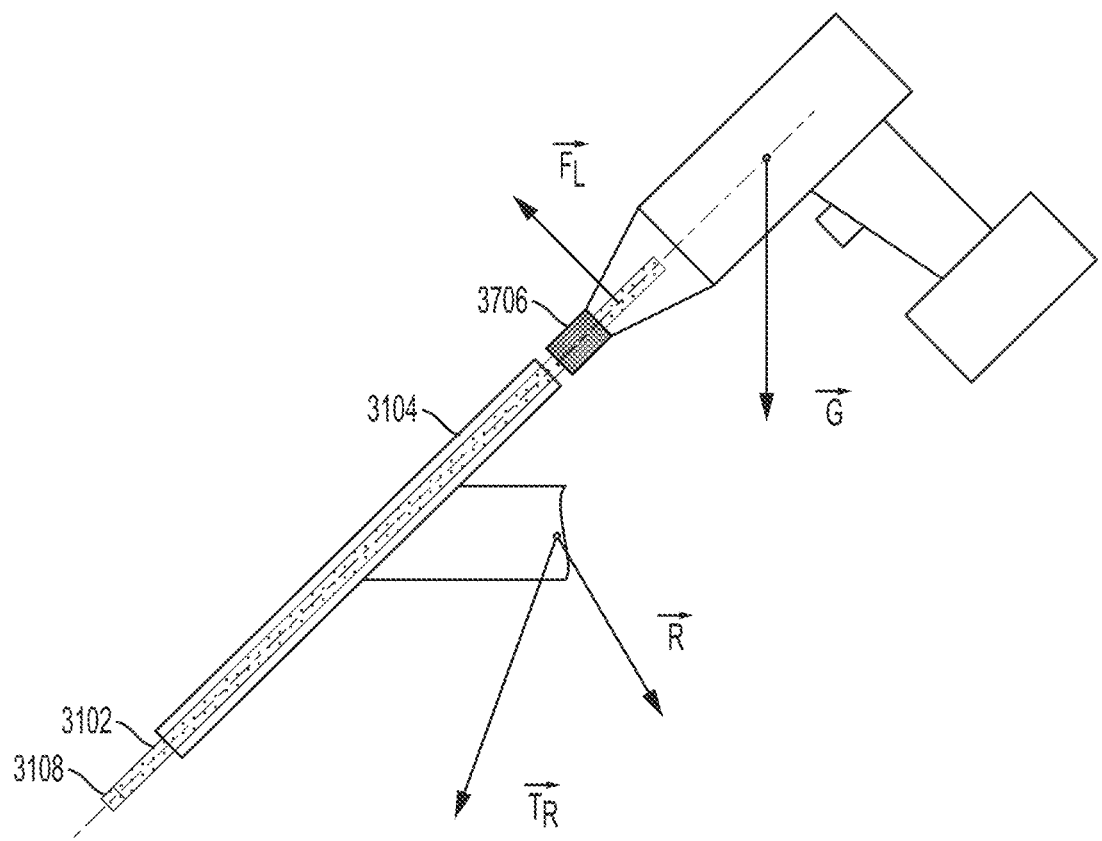
FIG. 36 illustrates a problem solved by use of a compliant part as described in relation to FIGS. 37 through 39C.
Figure 37A:
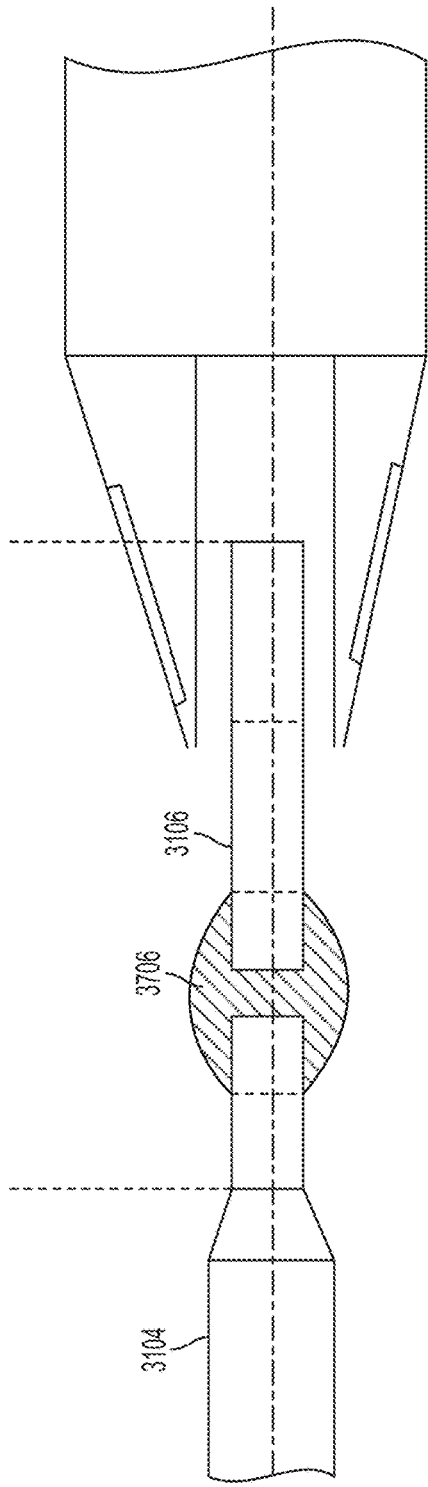
FIG. 37A and FIG. 37B illustrate example compliant parts in accordance with an embodiment of the invention.
Figure 37B:
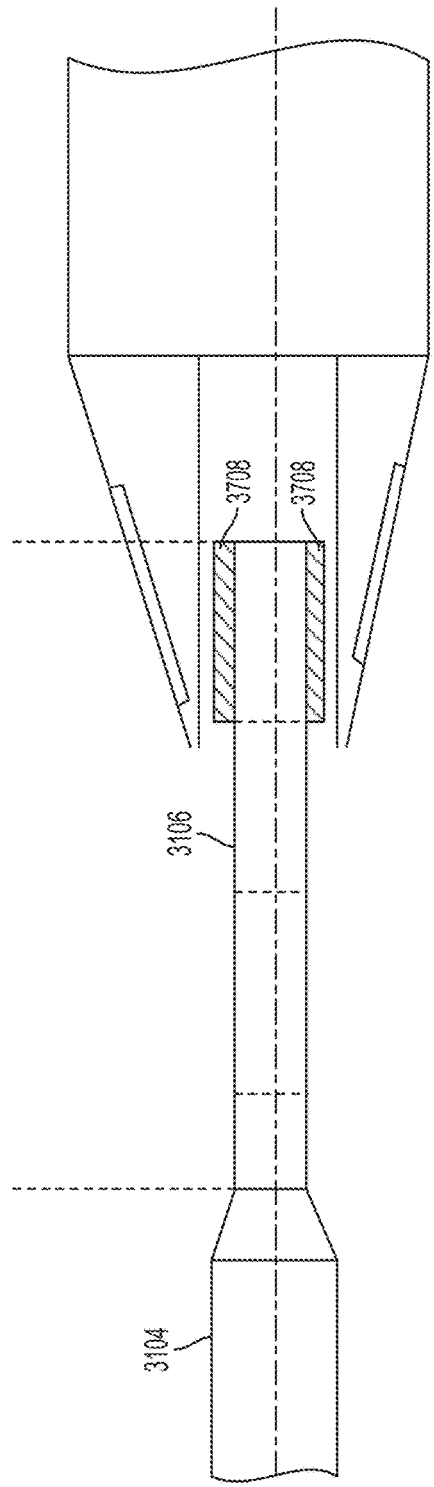
Figure 38:
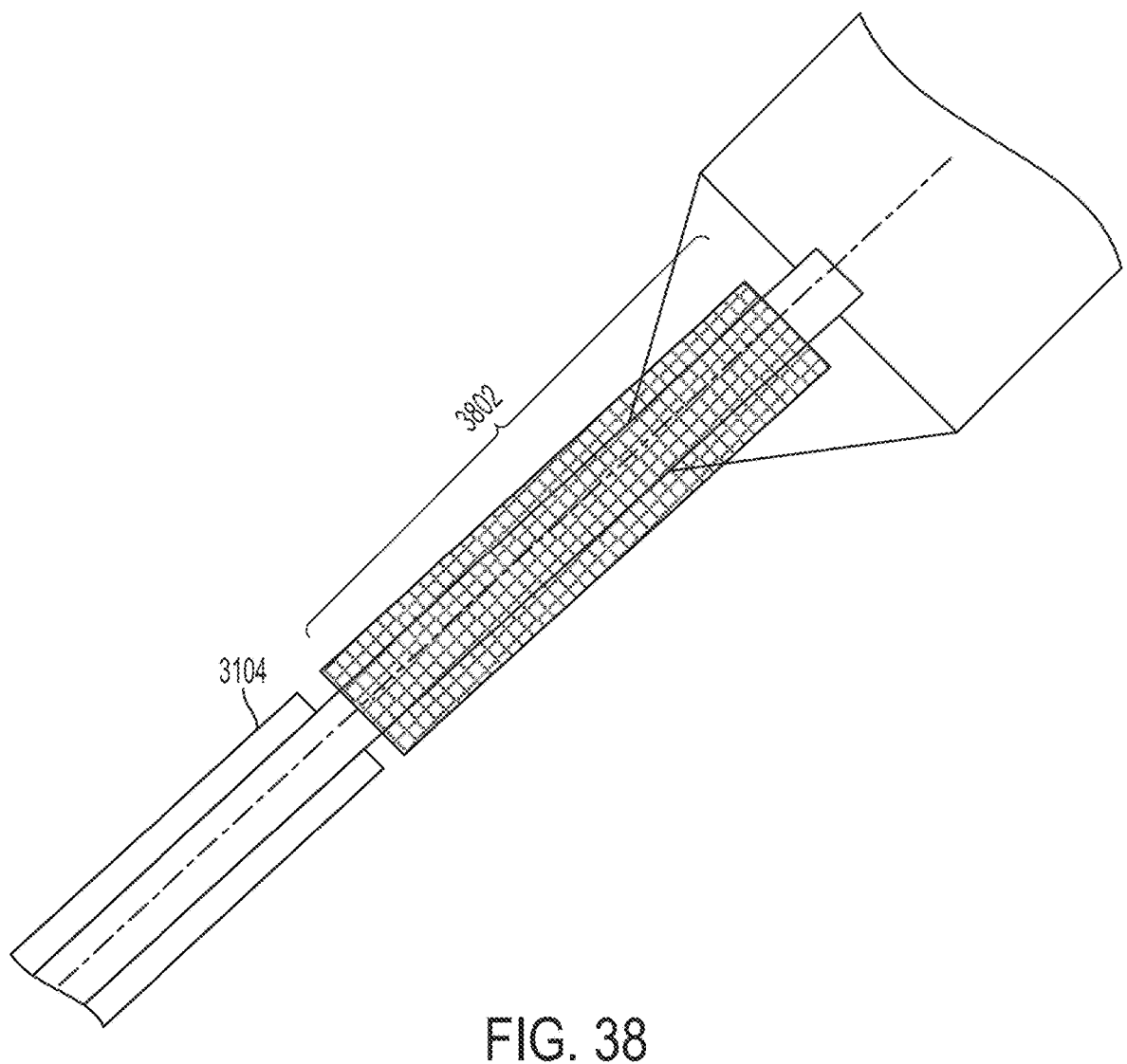
FIG. 38 illustrates an example compliant part in accordance with an embodiment of the invention.

FIG. 36 illustrates a set-up for describing the problem solved by a compliant part as described in relation to FIGS. 37 through 39. A drill guide is held by the robot represented by robot attachment. A drill bit is fixed to the surgical drill which gives drill bit rotation. Typically the surgical drill is hand held by the surgeon. A surgeon inserts drill bit into guide and drills hole in patient anatomy/bone (could be any bone, including vertebrae, cranial, and/or standard orthopedic surgery).

A surgical drill can have significant weight (e.g., a few kilograms even) which makes gravitation force G shown in FIG. 36 high. Additionally, drill rotation as well as forces applied by surgeon give forces FL. These forces generate high reactions at the robot attachment represented by reaction force R and torque TR. These high reactions put high load on robot part and guided instruments. Additionally, they can introduce imprecisions when guiding. To solve these problems, in certain embodiments, a compliant part (e.g., on or part of the drill bit) is used which allows the insertion movement while transmitting less reaction forces from the drill and drill bit system to the robot and guide.

FIGS. 37A and 37B is illustrate of a portions of drill bits in accordance with embodiment s of the invention. In this example, the drill bit includes one or more compliant parts (e.g., made of rubber). In some cases, it is difficult to hold the drill in line with the guide. One or more compliant parts increases the tolerance to these errors. As shown in FIG. 37A, the compliant part 3706 is used to connect first portion 3104 of the drill bit to a second portion 3106 of the drill bit. In an alternative embodiment, as shown in FIG. 37B, the compliant part 3708 extends around and/or covers at least a portion of the drill attachment part of the drill bit. In certain embodiments, both compliant part 3706 and compliant part 3708 are used. FIG. 38 illustrates a zone 3802 where the compliant part can be placed along the shaft of the drill bit. In certain embodiments, the compliant part can be located on the drill bit shaft and/or on the interface between drill bit and surgical drill.

Figure 39A:
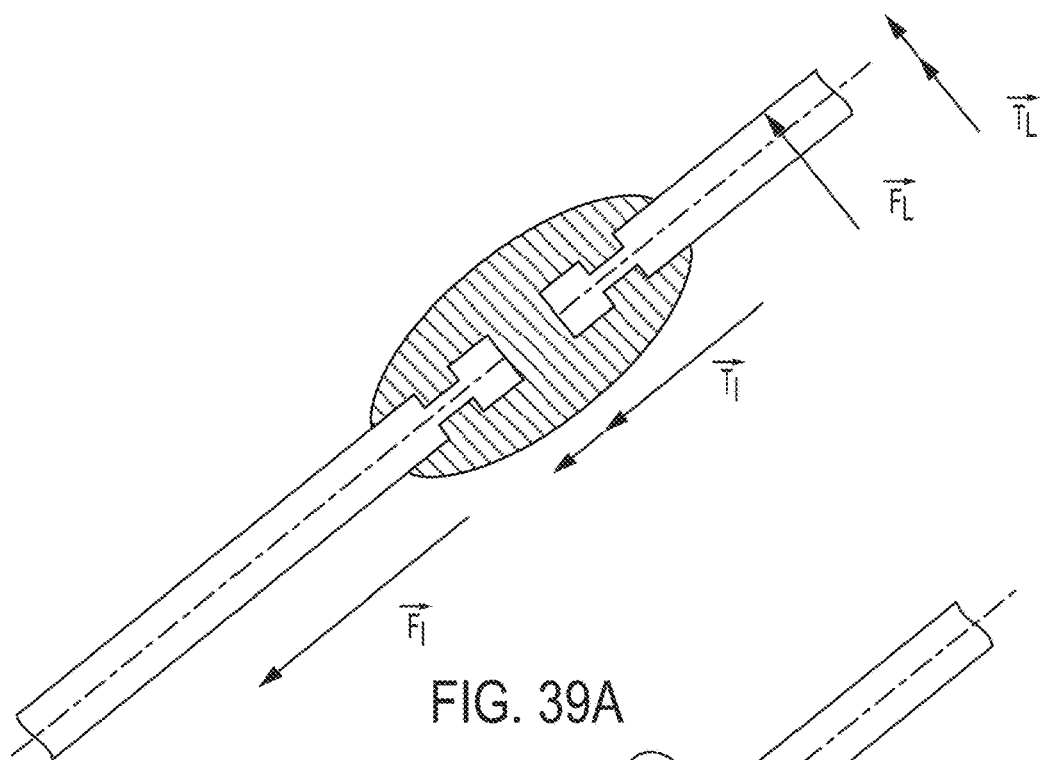
FIG. 39A, FIG. 39B, and FIG. 39C illustrate example compliant parts in accordance with an embodiment of the invention.
Figure 39B:
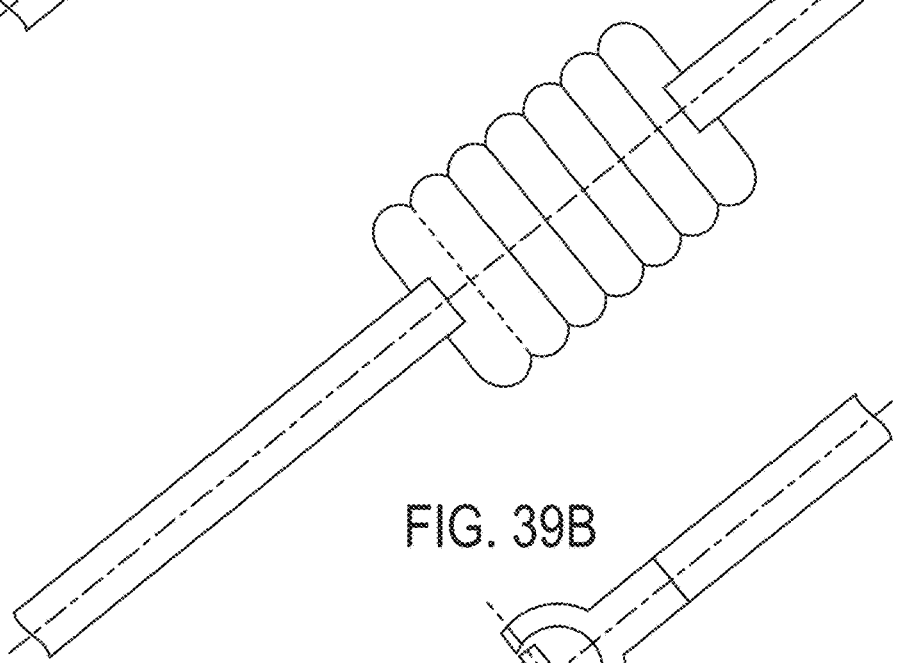
Figure 39C:
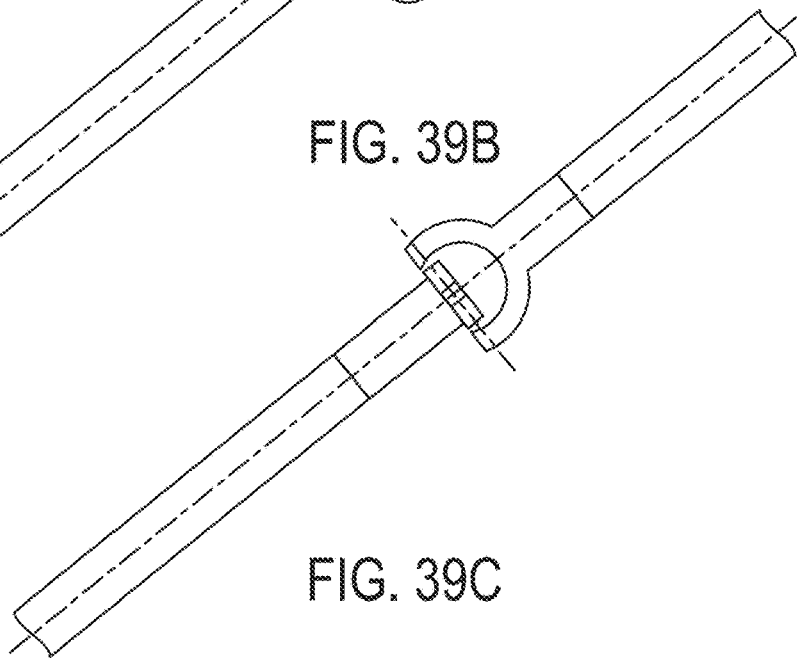

FIGS. 39A, 39B, and 39C illustrates various embodiments of a drill bit that includes a compliant part. The embodiment shown in FIG. 39A uses a compliant part made of elastic material, such as rubber. The embodiment shown in FIG. 39B uses a bellow as the compliant part, such as a metal bellow, is used to provide compliance. The embodiment shown in FIG. 39C uses a standard universal joint is used to allow for compliance.

Figure 40:
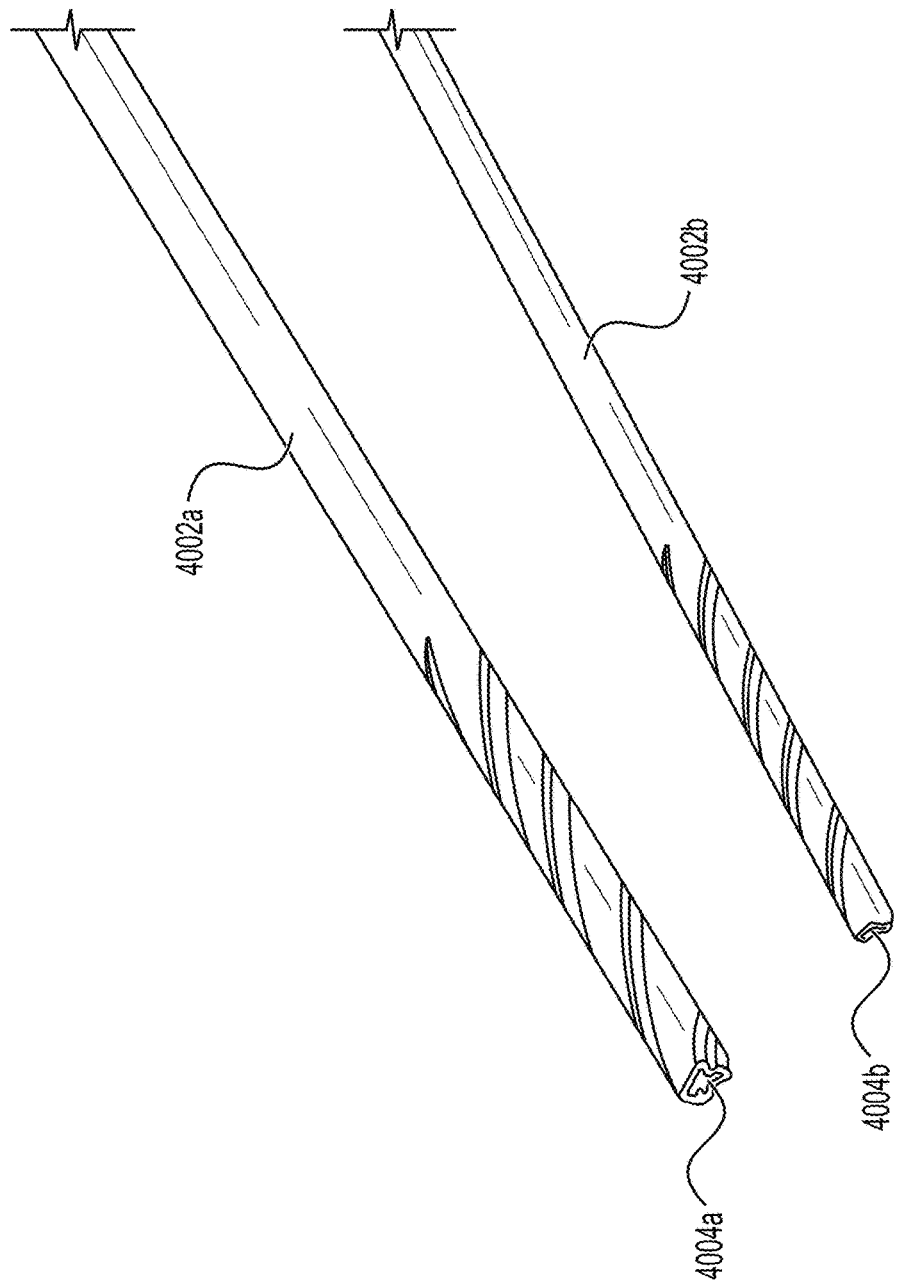
FIG. 40 is an illustration of cannulated drill bits.

FIG. 40 is an illustration of cannulated drill bits 4002a and 4002b. In certain embodiments, the drill bits disclosed herein are cannulated. In certain cases, surgeons prefer to use k-wires to provide guidance between various stages of the surgery. An example workflow is described in relation to, for example, FIGS. 2A, 2B and 9A of U.S. Patent Application Publication No. 2016/0235492, filed Feb. 18, 2016, entitled "Systems and Methods for Performing Minimally Invasive Spinal Surgery with a Robotic Surgical System using a Percutaneous Technique", the contents of which are hereby incorporated by reference in their entirety. To implement such workflow, a cannulation 4004a, 4004b (i.e., a throughput hole adapted to the size of the k-wire, also called guide wire) can be created in the drill bit 4002a, 4002b.

Figure 43:
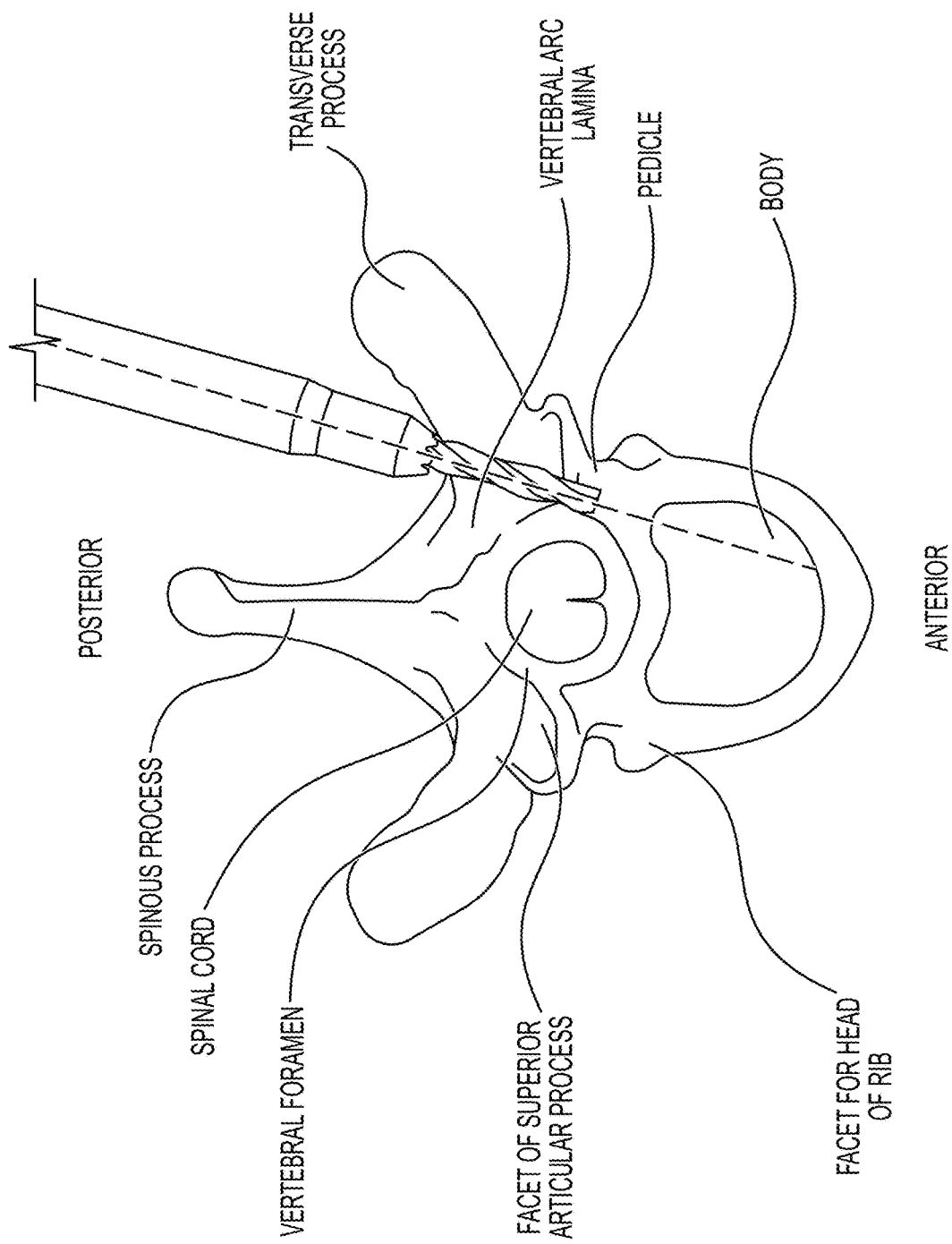
FIG. 43 shows a correct drilling trajectory when drilling through the pedicle of a vertebra, according to an illustrative embodiment.
Figure 44:
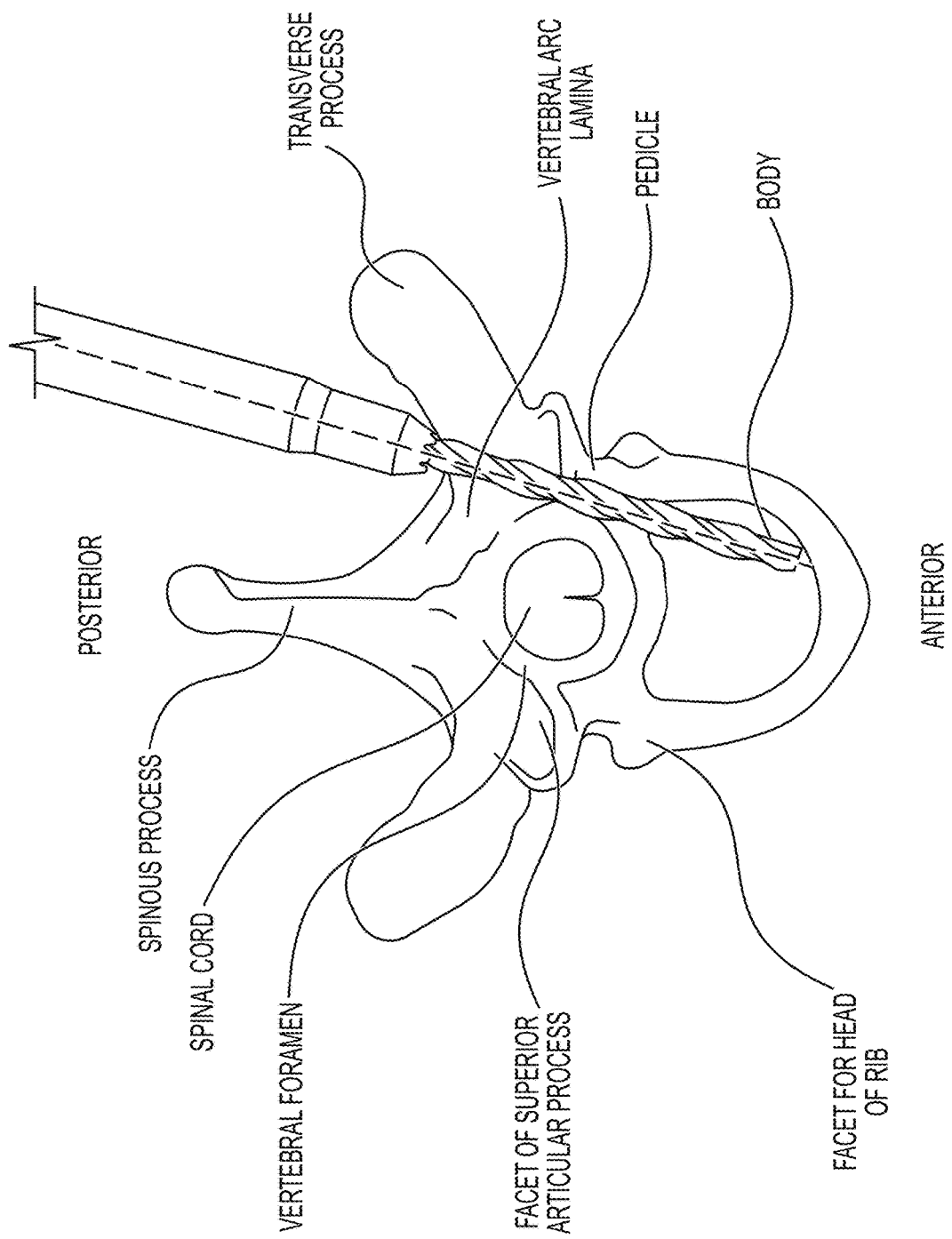
FIG. 44 shows a correct drilling trajectory when drilling through the pedicle of a vertebra at a later stage of drilling, according to an illustrative embodiment.

FIGS. 43 and 44 show a trajectory of a drill bit during a spinal procedure in accordance with the robotic surgical systems described above. In FIG. 43, the drill bit has penetrated into a vertebra along a trajectory whose axis is shown by the dashed line. In FIG. 44, the drill bit has penetrated further through the bone along the axis. In the procedure shown in FIGS. 43 and 44, the trajectory has been well-selected by the surgeon such that there is very little to no risk to the patient of complications related to the orientation and position of the prepared hole (e.g., the spinal cord has been sufficiently avoided).

Figure 45:
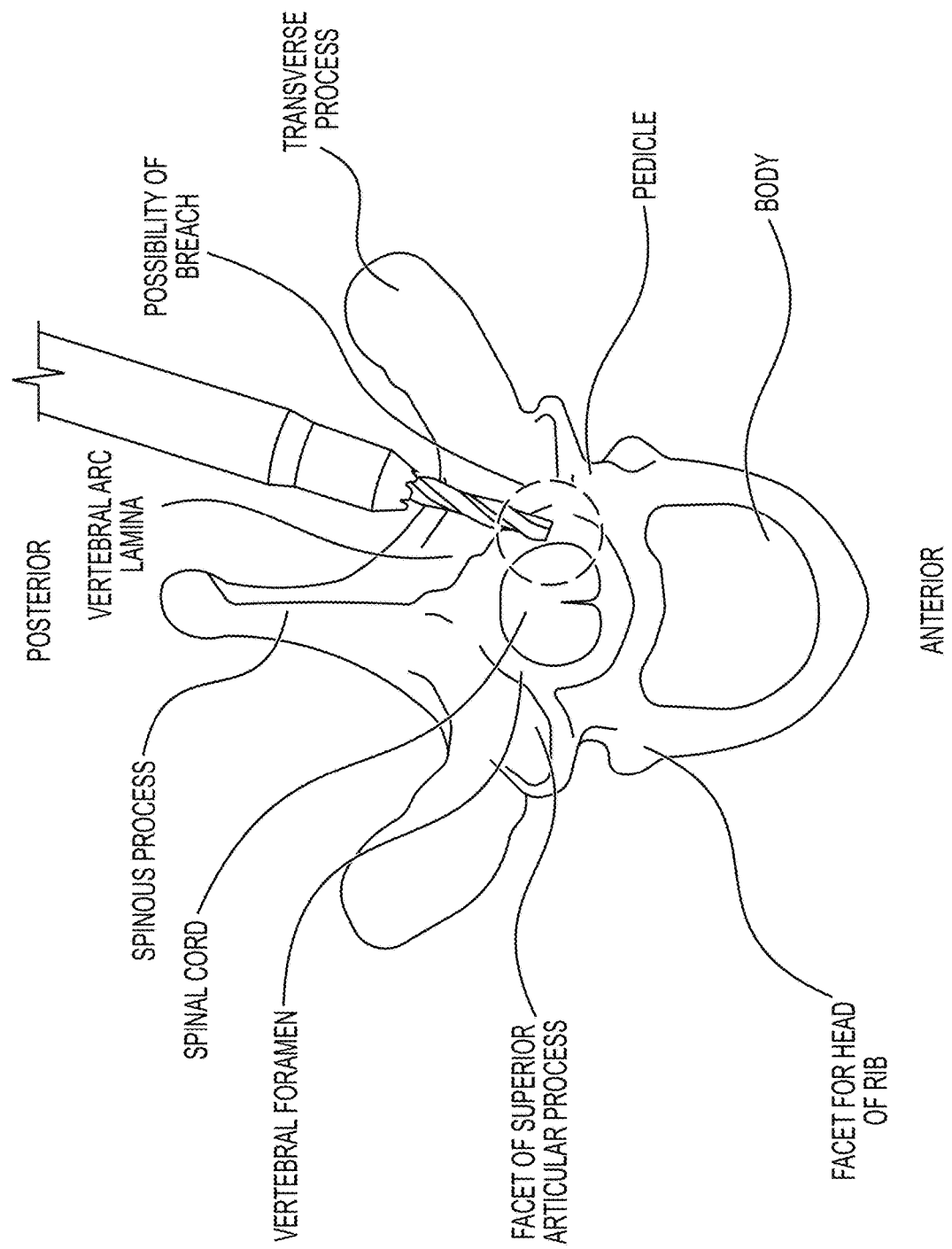
FIG. 45 shows an incorrect drilling trajectory that may result in a breach of the pedicle wall (e.g., exposing the spinal cord), according to an illustrative embodiment.
Figure 46:
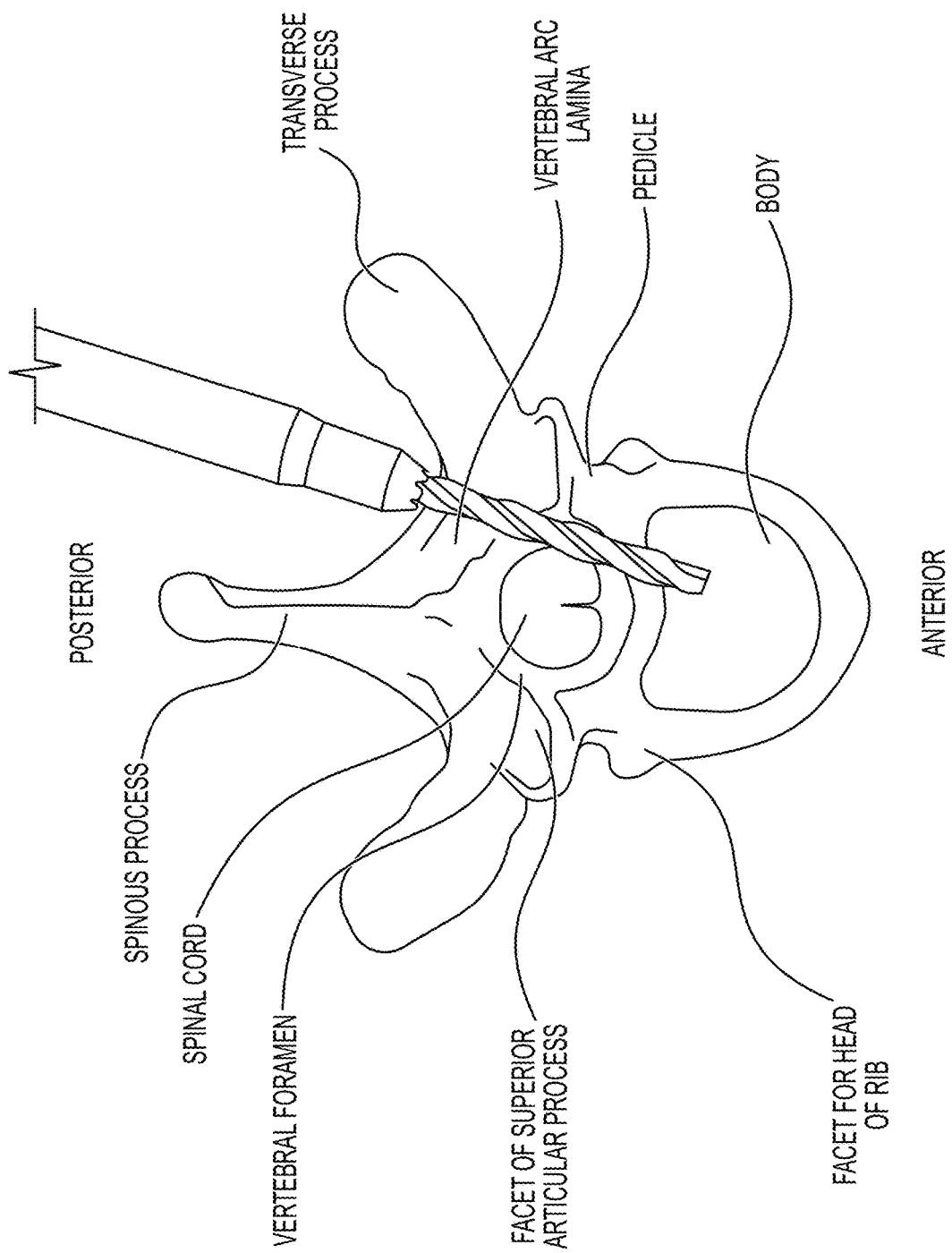
FIG. 46 shows an incorrect drilling trajectory that resulted in a breach of the pedicle wall (e.g., exposing the spinal cord)

FIGS. 45 and 46 show a trajectory where the spinal cord is not avoided and the pedicle wall is breached during the preparation procedure, resulting in serious complications for the patient. As seen in FIG. 45, the drill bit is headed towards the spinal cord such that there exists a possibility of a breach of the pedicle wall during hole preparation. As nothing is done to redirect the drill bit, the bit continues along its trajectory resulting in a breached pedicle wall, as shown in FIG. 46.

Figure 41:
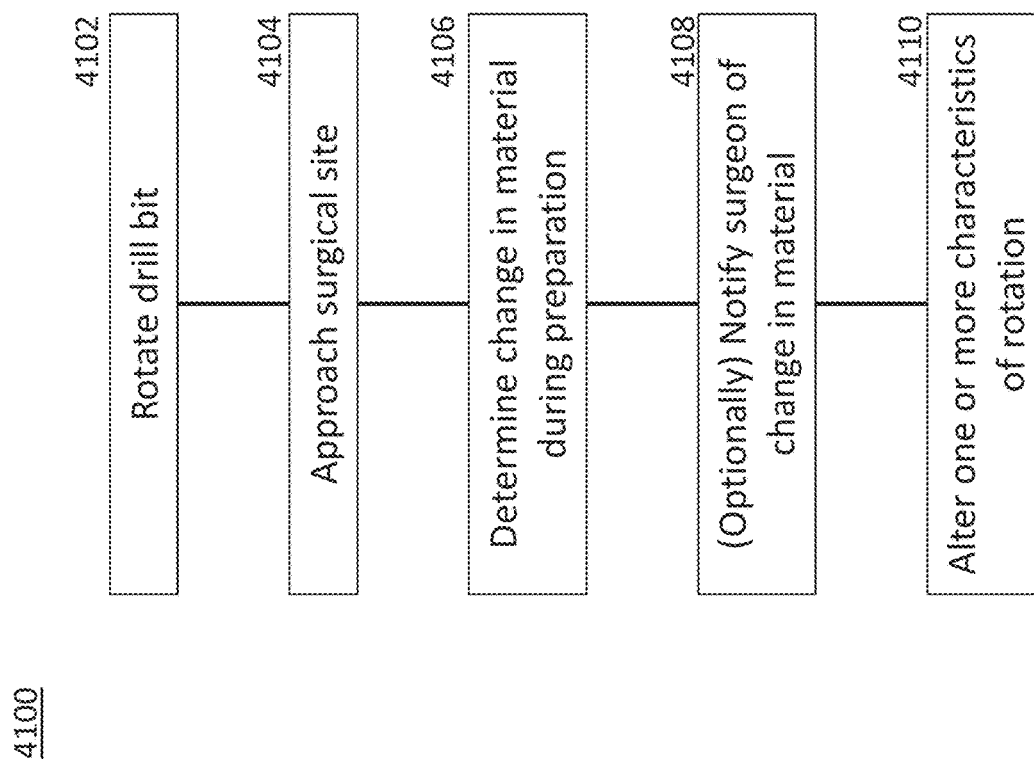
FIG. 41 is a block diagram of an exemplary method for precisely drilling a hole with a robotic surgical system performing surgery.

FIG. 41 is a block diagram of exemplary method 4100 that allows anatomy-guided correction of the drill bit during drilling. For example, the trajectory followed in FIG. 45 may be in situ modified to avoid breaching the pedicle wall by preparing the hole in accordance with method 4100. Starting in step 4102, the drill bit is rotating. In certain embodiments, the drill bit is an anti-skiving drill bit. In some embodiments, the drill bit is a standard medical drill bit. The rotation may be automatically started by a surgeon making an input or selection to a robotic surgical system (e.g., selecting a workflow or procedure from a list of options). The rotation may be caused by a surgeon providing input on the drill itself, for example, by pulling a trigger on the drill to cause rotation of the drill bit.

In step 4104, the rotating drill bit approaches the surgical site. For many procedures, the surgical site is recently exposed bone surface. In some embodiments, the surgical site is approached in a fixed-trajectory mode of motion for the robotic surgical system where only translation along a fixed trajectory (e.g., pre- or intra-operatively selected) is allowed. In this way, unwanted motion that would misalign the hole during preparation is avoided. In some embodiments, the robotic arm of the robotic surgical system is a passive, backdriveable arm such that the surgeon is free to manipulate surgical instruments as desired (e.g., easily modifying the current trajectory). The range of motion of a passive, backdriveable robotic arm (and, in some embodiments, active non-backdriveable robotic arms) may be limited by an operational volume around the surgical site that constrains motion of surgical instruments to within the volume. In some embodiments, movement of the drill bit, for example, along a fixed trajectory, occurs automatically by the robotic surgical system.

In step 4106, a change in material at a terminal point (e.g., a tool center point) (e.g., the tip) of the drill bit is determined. In certain embodiments, the determination is automatically made based on one or more criteria using a processor in the robotic surgical system. In certain embodiments, the change in material is a change from the hard outer layer of a bone to the spongious interior of a bone. The bone may be a vertebra or portion thereof (e.g., a pedicle). The change in material may also be a change from a hard outer layer or a spongious interior of a bone to a cavity, canal, or passage in or through the bone (e.g., indicating that the drill bit has penetrated to a back side of a bone).

The change in material may be determined based on haptic feedback measured, for example, by a force sensor attached to the robotic arm, end effector, surgical instrument, surgical instrument guide, or elsewhere on the robotic surgical system. In this way, different mechanical properties between regions of a bone that provide differing resistive forces to a drill bit are measured in the haptic feedback recorded by the force sensor for use in determining that the change in material has occurred. In some embodiments, a change in material is determined based on having received a substantially constant magnitude of haptic feedback over a certain drilling distance. For example, receiving haptic feedback that corresponds to the hard outer layer of bone over a drilling distance that corresponds approximately to the average thickness of the hard outer layer of a bone may prompt the determination that a change in material has occurred.

The change in material may be based on medical image data or a model of patient anatomy derived therefrom. For example, using a registration of a patient's anatomy to the robotic surgical system, a change in material may be determined from a change in contrast, brightness, and/or color in medical image data and related to the position of the drill bit attached to the robotic surgical system using the registration. In this way, a surgeon can use a navigation system to see that the tip of a drill bit has changed from being in a region of one material to being in a region of another material without necessarily receiving any haptic feedback due to the transition. Registration of a robot to a patient's anatomy allows the position of the tip of a drill bit to be visualized in a navigation system. In some embodiments, medical image data is collected real-time during a procedure and the drill bit is visualized in the display of the data. In some embodiments, a surgeon provides input to a robotic surgical system that indicates a change in material is occurring based on real-time information obtained from a navigation system (e.g., that uses medical image data). For example, the surgeon may observe the position of the drill bit relative to the patient's anatomy in the navigation system and then indicate that the drill bit has entered the spongious interior of a bone.

The change in material may be determined using a position of a terminal point of the drill bit. In some embodiments, the terminal point is determined to be at a position where the material has changed based on a registration and medical image data. In some embodiments, a change in material is determined after a certain translation along an axis (e.g., in a fixed-trajectory mode) of the position of the terminal point. For example, the hard outer layer of bone may be assumed to have a certain thickness with the change in material determined based on a translation equivalent to the certain thickness. An additional margin or threshold distance may be included (e.g., in order to increase safety).

In optional step 4108, the surgeon is notified of the change in material. The notification may be haptic feedback, a graphic, a sound, or a light signal. Haptic feedback may provide large-magnitude resistive forces to the surgeon to indicate a change in material has been determined. In some embodiments, such a notification prohibits the surgeon from continuing the surgical procedure until one or more rotational characteristics of the drill bit are altered (e.g., to be above or below a certain threshold (e.g., a maximum rotational speed)). The sound may be a single or repeated beeping, for example. The light signal may be a single or repeated flashing light of any color. The light signal or sound may emanate from a display used by the surgeon when operating the robotic surgical system. The graphic may be a pop-up image, icon, or text that appears on the display. The tone, volume, or length of the sound; duration, color, or intensity of the light signal; or text, image, or icon of the graphic may indicate to the surgeon not only that a determination of change in material has been made, but further indicate what type of change has been determined (i.e., between which two materials or types of materials) and/or which characteristics of rotation should be altered in response (and, optionally, to what degree). In some embodiments, graphic notifications explicitly indicate to a surgeon to alter characteristics of rotation of the drill bit in response to the change in material.

In step 4110, one or more characteristics of rotation of the drill bit are altered based, at least in part, on the determination of change in material. The one or more characteristics may be altered additionally based at least in part on, for example, the particular bone a hole is being prepared in or the particular surgical procedure being performed on the bone. In certain embodiments, step 4110 occurs automatically upon determination of change in material. In some embodiments, the robotic surgical system guides the surgeon to manually alter the one or more characteristics of rotation. For example, upon determination of the change in material, the maximum speed of rotation may become limited. The one or more characteristics of rotation may include rotational speed, rotational velocity, rotational direction (e.g., clockwise or counterclockwise), and rotational mode (e.g., wherein the rotational mode is either an oscillatory rotation mode or a unidirectional rotation mode). In certain embodiments, rotational speed is altered by decreasing rotational speed (e.g., to about 15 rpm, about 20 rpm, between 10 and 20 rpm, no more than 20 rpm, no more than 40 rpm, no more than 100 rpm, no more than 200 rpm, no more than 50 rpm, at least 100 rpm, between 10 and 100 rpm, between 10 and 50 rpm, between 50 and 100 rpm, between 10 and 200 rpm, or subranges thereof). In certain embodiments, the rotational mode is an oscillatory mode wherein oscillations occur over an arc about an axis of the drill bit (e.g., an arc of about 10 degrees, about 20 degrees, about 30 degrees, about 90 degrees, about 120 degrees, about 180 degrees, about 360 degrees, no more than 30 degrees, no more than 60 degrees, no more than 90 degrees, no more between 20 degrees and 40 degrees, between 10 degrees and 60 degrees, between 10 degrees and 90 degrees, between 45 degrees and 90 degrees, between 90 degrees and 180 degrees, between 180 degrees and 360 degrees, between about 10 degrees and 360 degrees, or subranges thereof).

Figure 47:
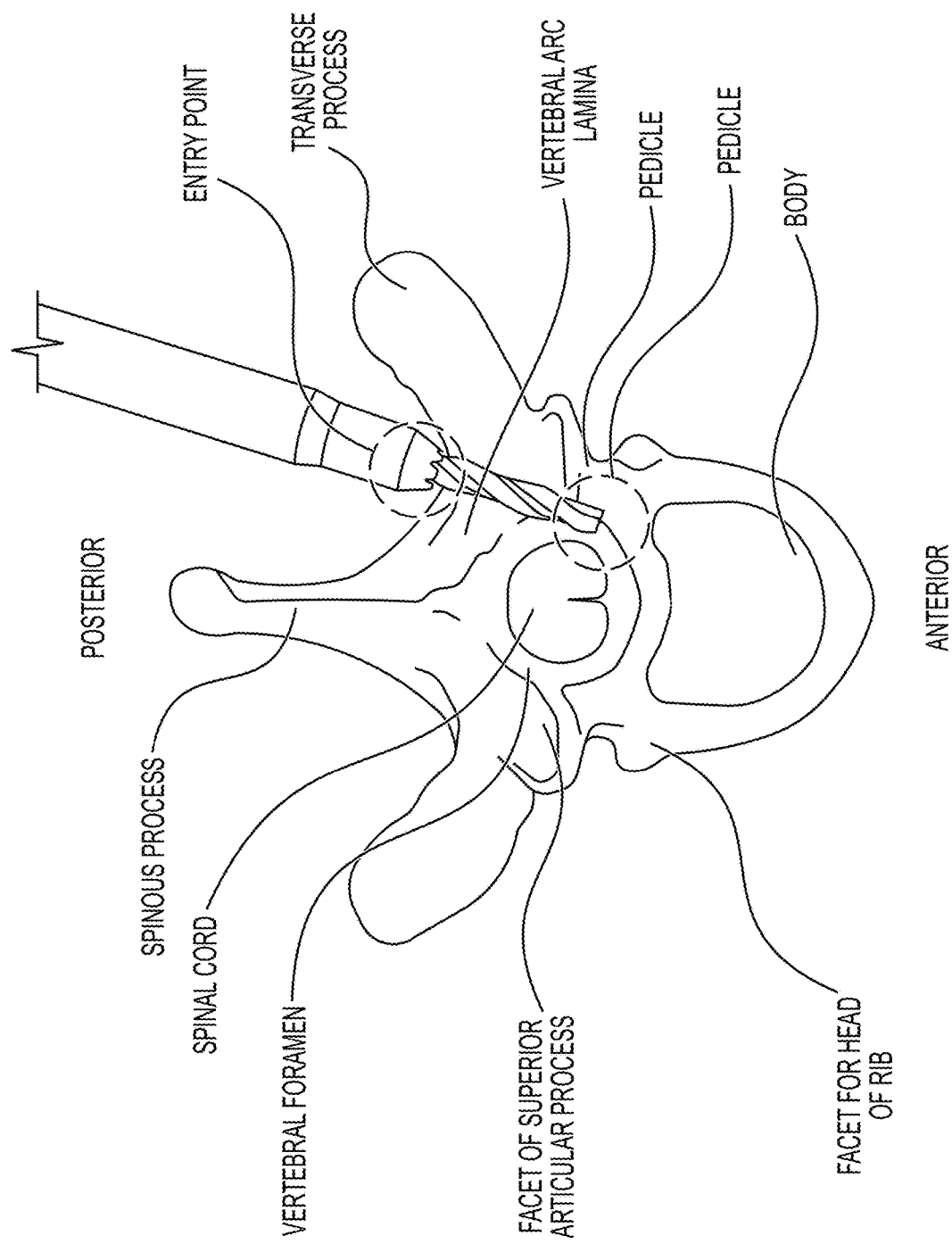
FIG. 47 shows a drilling trajectory correction resulting from an altered characteristic of rotation while drilling the pedicle, according to an illustrative embodiment.
Figure 48:
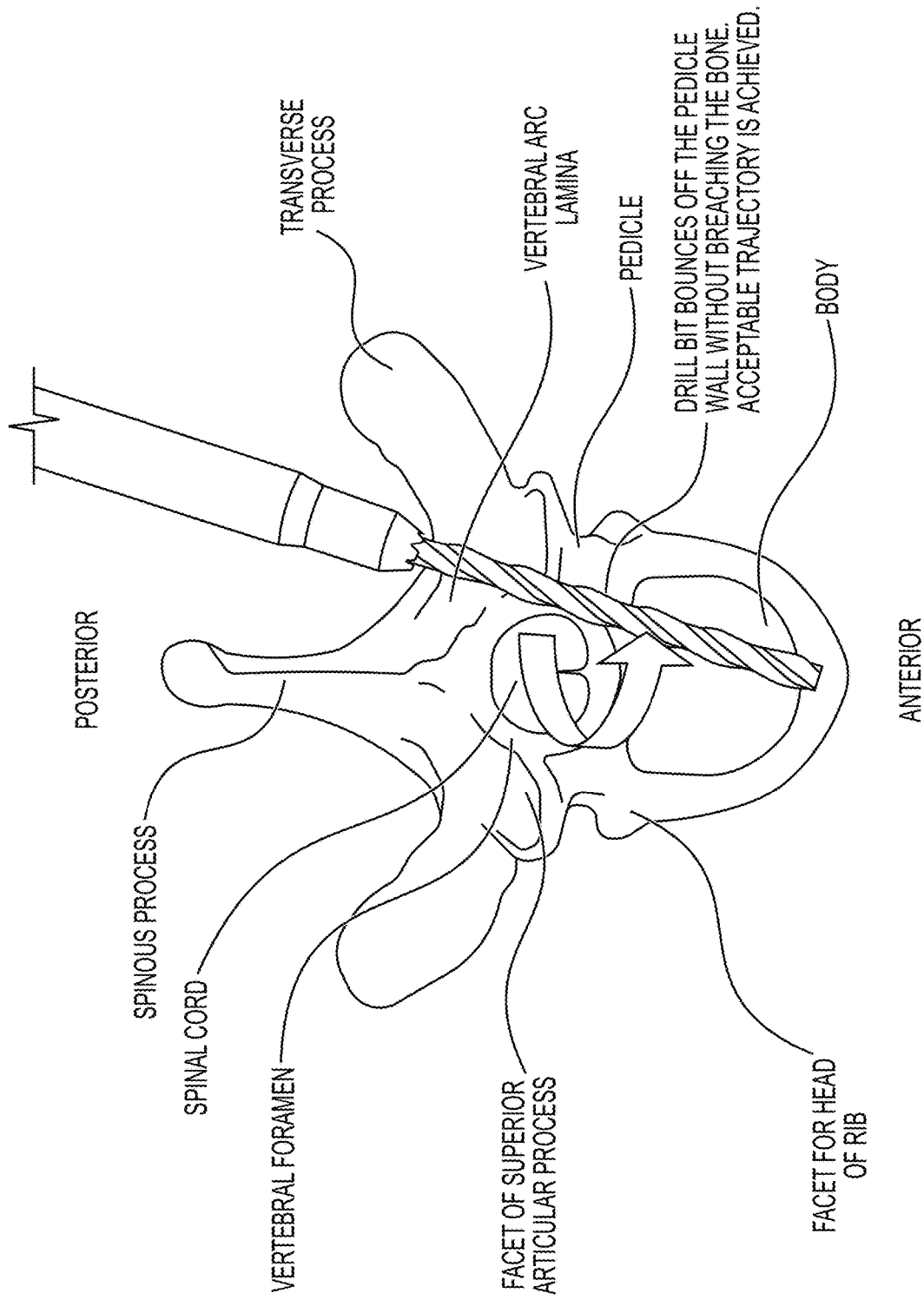
FIG. 48 shows a drilling trajectory correction resulting from an altered characteristic of rotation while drilling the pedicle at a later stage of drilling, according to an illustrative embodiment.

In an exemplary procedure according to method 4100, a robotic surgical system with an anti-skiving drill bit is used. FIGS. 47 and 48 show the trajectory chosen in this exemplary procedure. Starting in step 4102, the drill bit is rotating at high speed to minimize skidding at the vertebra surface as the vertebra is first penetrated. Despite minimal skidding occurring during bone entry, the chosen trajectory will possibly breach pedicle wall. In step 4110, the rotational speed of the drill is automatically reduced to between 10 and 20 rpm once it is determined that the drill bit has entered the spongious interior. Slow rotational speed is sufficient to drill through the spongious interior, but insufficient to drill the hard outer layer of a bone. Similarly, in certain embodiments, oscillatory rotations or counterclockwise rotations can drill through spongious interior but not hard outer layer of bone. As shown in FIG. 48, the inability of the drill bit to penetrate the hard outer layer of bone due to altered characteristics of rotation leads the drill bit to remain inside the pedicle and avoid breaching the pedicle wall (i.e., penetrating the spinal cord). Skidding may occur during while drilling through the spongious interior, but, when used as such, is useful in optimizing the trajectory of the hole being prepared to reduce or eliminate complications for the patient.

Figure 42:
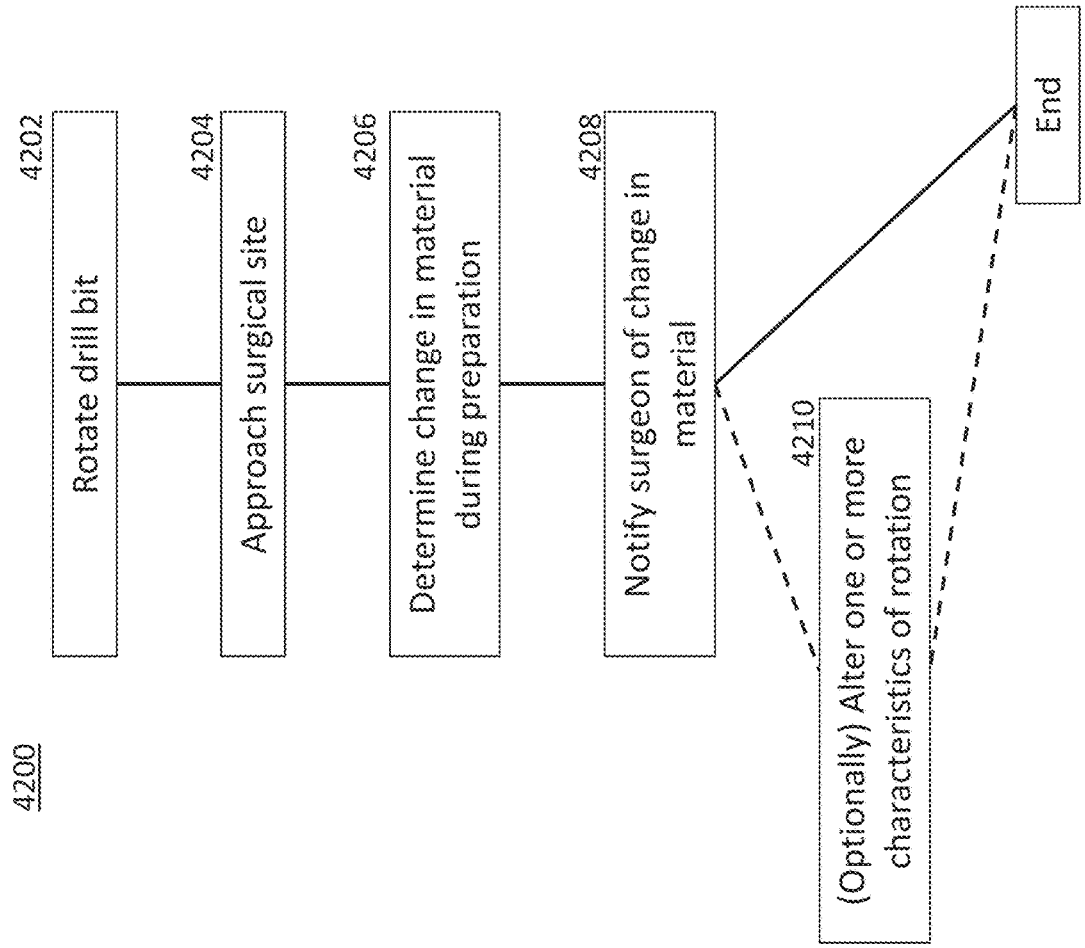
FIG. 42 is a block diagram of an exemplary method for notifying a surgeon of when to alter drilling characteristics with a robotic surgical system, while performing a surgical procedure.

FIG. 42 is a block diagram of exemplary method 4200, wherein a surgeon is notified that a determination of change in material has been made and can, if so desired, alter one or more characteristics of rotation of a drill bit in response to the determination. Steps 4202, 4204, and 4206 proceed similarly to corresponding steps 4102, 4104, and 4104 of exemplary method 4100, respectively. In step 4208, the surgeon is notified of the determination of change in material. The notifications may be any of the notifications discussed above in relation to step 4108. In certain implementations, the method ends once the notification has been made. The surgeon can then choose to heed the information provided by the notification (e.g., to alter certain characteristics of rotation) or disregard it. For example, the surgeon may determine that although a change in material has been determined, the current trajectory does not warrant altering rotational characteristics of the drill bit. In certain implementations, the method proceeds to optional step 4210 where one or more characteristics of rotation are altered (e.g., automatically) after notification as discussed above in relation to step 4110, after which the method ends.

It is understood that methods described herein as related to surgical procedures on the spine or a vertebra thereof are described as such to be exemplary. Many surgical procedures require the preparation of a hole in a bone following a precise trajectory such that they benefit from the use of systems and methods disclosed herein. Other procedures are equally adapted to utilize systems and methods described herein. Other surgeries contemplated for use include, but are not limited to, orthopedic procedures, ENT procedures, and neurosurgical procedures. Such procedures may be performed using an open, percutaneous, or minimally invasive approach.

In view of the structure, functions and apparatus of the systems and methods described here, in some implementations, a system and method for preparing holes in bone with a robotic surgical system are provided. Having described certain implementations of methods and systems for using a robotic surgical system, it will now become apparent to one of skill in the art that other implementations incorporating the concepts of the disclosure may be used. Therefore, the disclosure should not be limited to certain implementations, but rather should be limited only by the spirit and scope of the following claims.

Throughout the description, where apparatus and systems are described as having, including, or comprising specific components, or where processes and methods are described as having, including, or comprising specific steps, it is contemplated that, additionally, there are apparatus, and systems of the disclosed technology that consist essentially of, or consist of, the recited components, and that there are processes and methods according to the disclosed technology that consist essentially of, or consist of, the recited processing steps.

It should be understood that the order of steps or order for performing certain action is immaterial so long as the disclosed technology remains operable. Moreover, two or more steps or actions may be conducted simultaneously.

What is claimed is:

1. A surgical robot system comprising:
a robot having a robot arm and an end effector coupled to the robot arm, the end effector having a guide channel;
a drill including:
a main body;
a guide sleeve coupled to the main body and adapted to be received in the guide channel of the end effector;
a drill bit received in the guide sleeve, wherein the drill bit includes a first drill shaft and a separate second drill shaft spaced from the first drill shaft, wherein the first drill bit shaft and the second drill shaft are formed as separate independent components;
a compliant part disposed around portions of the first drill shaft and the second drill shaft to maintain a physical separation between the first drill shaft and the second drill shaft and to provide compliance between the drill bit and the main body.

2. The surgical robot system of claim 1, wherein the compliant part includes elastomeric material circumferentially surrounding the first and second drill shafts.

3. The surgical robot system of claim 1, wherein the compliant part includes a bellow.

4. The surgical robot system of claim 3, wherein the compliant part includes a metal bellow.

5. The surgical robot system of claim 1, wherein the compliant part includes a universal joint.

6. The surgical robot system of claim 1, wherein the end effector includes an array of navigation markers for position tracking by a navigation system.

7. The surgical robot system of claim 1, wherein the drill includes drill navigation markers attached to the guide sleeve.

8. A surgical robot system comprising:
a robot having a robot arm, an end effector coupled to the robot arm and a processor programmed to control the robot arm and the end effector to place the end effector in a pre-planned trajectory, the processor further configured to detect a change in tissue to be cut, the end effector having a guide channel;
a drill including:
a main body;
a guide sleeve coupled to the main body and adapted to be received in the guide channel of the end effector;
a drill bit received in the guide sleeve, wherein the drill bit includes a first drill shaft and a separate second drill shaft spaced from the first drill shaft, wherein the first drill bit shaft and the second drill shaft are formed as separate independent components;
a compliant part disposed around portions of the first drill shaft and the second drill shaft to maintain a physical separation between the first drill shaft and the second drill shaft and to provide compliance between the drill bit and the main body.

9. The surgical robot system of claim 8, wherein the compliant part includes a flexible sleeve circumferentially surrounding the drill bit.

10. The surgical robot system of claim 9, wherein the compliant part is disposed inside the main body of the drill.

11. The surgical robot system of claim 8, wherein the compliant part includes elastomeric material circumferentially surrounding the first and second drill shafts.

12. The surgical robot system of claim 8, wherein the compliant part includes a bellow.

13. The surgical robot system of claim 12, wherein the compliant part includes a metal bellow.

14. The surgical robot system of claim 8, wherein the compliant part includes a universal joint.

15. The surgical robot system of claim 8, wherein the end effector includes an array of navigation markers for position tracking by a navigation system.

16. The surgical robot system of claim 8, wherein the drill includes drill navigation markers attached to the guide sleeve.

* * * * *